United States Patent
Henig et al.

(10) Patent No.: US 10,045,687 B2
(45) Date of Patent: Aug. 14, 2018

(54) DENTAL IMPLANTS, DEVICES AND METHODS ASSOCIATED WITH DENTAL IMPLANTATION PROCEDURES

(75) Inventors: Itzhak Henig, Ashkelon (IL); Oded Nahlieli, Ashkelon (IL); Shmuel Shmueli, Tel-Aviv (IL); Hagay Jacobsen, Kfar Vradim (IL)

(73) Assignee: SIALO-LITE LTD., Ashkelon (IL)

( * ) Notice: Subject to any disclaimer, the term of this patent is extended or adjusted under 35 U.S.C. 154(b) by 0 days.

(21) Appl. No.: 13/575,259

(22) PCT Filed: Jan. 25, 2011

(86) PCT No.: PCT/IL2011/000083
§ 371 (c)(1),
(2), (4) Date: Jul. 25, 2012

(87) PCT Pub. No.: WO2011/092688
PCT Pub. Date: Aug. 4, 2011

(65) Prior Publication Data
US 2013/0011815 A1    Jan. 10, 2013

Related U.S. Application Data

(63) Continuation of application No. 12/656,341, filed on Jan. 26, 2010, now Pat. No. 8,366,443, and a
(Continued)

(51) Int. Cl.
*A61C 8/00* (2006.01)
*A61B 1/247* (2006.01)
(Continued)

(52) U.S. Cl.
CPC .............. *A61B 1/247* (2013.01); *A61C 1/088* (2013.01); *A61C 8/005* (2013.01); *A61C 8/0018* (2013.01);
(Continued)

(58) Field of Classification Search
CPC ... A61C 8/0006; A61C 8/0039; A61C 8/0092; A61C 8/005; A61C 8/006; A61C 8/0022;
(Continued)

(56) References Cited

U.S. PATENT DOCUMENTS 612,662 A     10/1898   Detwiler
2,857,670 A *  10/1958   Kiernan, Jr. ......... A61C 8/0018
                                                433/175
(Continued)

FOREIGN PATENT DOCUMENTS

DE     44 04 983 A1    9/1994
DE     43 21 785 C1    3/1995
(Continued)

OTHER PUBLICATIONS

International Search Report for corresponding International PCT Application No. PCT/IL2010/000900, dated Mar. 15, 2011, 6 pages.
(Continued)

*Primary Examiner* — Cris L Rodriguez
*Assistant Examiner* — Matthew Saunders
(74) *Attorney, Agent, or Firm* — Tutunjian & Bitetto, P.C.

(57) ABSTRACT

A dental implant is provided. In some embodiments, the dental implant facilitates viewing an outside of a distal end of the dental implant via a proximal opening of the dental implant, and/or facilitates providing bone graft material via selectively closable one or more distal openings. A dental implant installation procedure is also provided in which a distal end of a dental implant is projected into a paranasal sinus cavity or a nasal cavity to displace the respective sinus membrane or nasal cavity membrane from the respective cavity floor, while minimizing risk of damaging the respective membrane. Bone graft material is introduced into the space created between the respective membrane and the
(Continued)

respective cavity floor via a distal portion of the dental implant to form a desired sinus augmentation.

22 Claims, 25 Drawing Sheets

Related U.S. Application Data continuation of application No. PCT/IL2010/000900, filed on Nov. 1, 2010.

(51) Int. Cl.
| | |
|---|---|
| A61C 9/00 | (2006.01) |
| A61B 1/04 | (2006.01) |
| A61C 1/00 | (2006.01) |
| A61C 1/07 | (2006.01) |
| A61C 1/08 | (2006.01) |
| A61C 1/12 | (2006.01) |
| A61C 3/03 | (2006.01) |
| A61C 17/02 | (2006.01) |
| A61C 17/06 | (2006.01) |

(52) U.S. Cl.
CPC .......... *A61C 8/0022* (2013.01); *A61C 8/0075* (2013.01); *A61C 8/0092* (2013.01); *A61C 9/008* (2013.01); *A61B 1/04* (2013.01); *A61C 1/0046* (2013.01); *A61C 1/0061* (2013.01); *A61C 1/07* (2013.01); *A61C 1/082* (2013.01); *A61C 1/12* (2013.01); *A61C 3/03* (2013.01); *A61C 8/006* (2013.01); *A61C 8/0068* (2013.01); *A61C 8/0089* (2013.01); *A61C 17/02* (2013.01); *A61C 17/0208* (2013.01); *A61C 17/04* (2013.01)

(58) Field of Classification Search
CPC ... A61C 8/0069; A61C 8/0089; A61B 17/666; A61B 17/864
USPC ............................... 433/172–176, 180, 201.1
See application file for complete search history.

(56) References Cited

U.S. PATENT DOCUMENTS

| | | | |
|---|---|---|---|
| 3,807,048 A | 4/1974 | Malmin | |
| 4,671,768 A | 6/1987 | Ton | |
| 5,013,242 A * | 5/1991 | Prezmecky | A61C 8/0033 433/173 |
| 5,312,256 A * | 5/1994 | Scortecci | 433/174 |
| 5,439,381 A * | 8/1995 | Cohen | A61C 8/001 433/173 |
| 5,503,558 A * | 4/1996 | Clokie | A61C 8/0018 433/172 |
| 5,503,559 A | 4/1996 | Vari | |
| 5,584,688 A * | 12/1996 | Sakuma et al. | 433/81 |
| 5,662,586 A | 9/1997 | Monroe et al. | |
| 5,711,315 A | 1/1998 | Jerusalmy | |
| 5,800,165 A | 9/1998 | Kirsch et al. | |
| 5,871,484 A * | 2/1999 | Spievack | A61B 17/72 604/285 |
| 5,899,696 A * | 5/1999 | Shimoda | 433/173 |
| 5,915,967 A * | 6/1999 | Clokie | A61C 8/0018 433/173 |
| 5,999,687 A | 12/1999 | Abraham et al. | |
| 6,013,025 A | 1/2000 | Bonne et al. | |
| 6,042,380 A | 3/2000 | De Rowe | |
| 6,093,183 A | 7/2000 | Pavkovich | |
| 6,126,662 A * | 10/2000 | Carmichael et al. | 606/916 |
| 6,162,052 A | 12/2000 | Kokubu | |
| 6,270,342 B1 | 8/2001 | Neuberger et al. | |
| 6,458,120 B1 | 10/2002 | Shen et al. | |
| 6,635,011 B1 | 10/2003 | Ozawa et al. | |
| 6,679,837 B2 | 1/2004 | Daikuzono | |
| 6,799,970 B2 | 10/2004 | Martin et al. | |
| 6,840,770 B2 | 1/2005 | McDevitt | |
| 7,125,253 B2 | 10/2006 | Kitamura et al. | |
| 7,510,397 B2 | 3/2009 | Hochman | |
| 7,771,199 B2 * | 8/2010 | Hochman et al. | 433/215 |
| 7,771,482 B1 * | 8/2010 | Karmon | 623/17.17 |
| 7,776,042 B2 * | 8/2010 | Ainsworth | A61B 17/70 606/249 |
| 7,934,929 B2 | 5/2011 | Better et al. | |
| 8,475,505 B2 * | 7/2013 | Nebosky | A61B 17/7061 606/304 |
| 2002/0102516 A1 | 8/2002 | Srouji et al. | |
| 2002/0177102 A1 | 11/2002 | Martin et al. | |
| 2003/0105469 A1 * | 6/2003 | Karmon | 606/92 |
| 2003/0124486 A1 * | 7/2003 | McDevitt | 433/167 |
| 2004/0073374 A1 | 4/2004 | Lockhart et al. | |
| 2004/0162572 A1 | 8/2004 | Sauer | |
| 2004/0230195 A1 * | 11/2004 | Kaikkonen et al. | 606/72 |
| 2006/0084034 A1 * | 4/2006 | Hochman | 433/173 |
| 2006/0172255 A1 * | 8/2006 | Hochman et al. | 433/144 |
| 2006/0235273 A1 | 10/2006 | Moriyama et al. | |
| 2007/0088203 A1 | 4/2007 | Lau | |
| 2007/0162024 A1 * | 7/2007 | Siemonsmeier | 606/72 |
| 2007/0225695 A1 * | 9/2007 | Mayer et al. | 606/15 |
| 2008/0108011 A1 | 5/2008 | Nahlieli | |
| 2008/0118893 A1 * | 5/2008 | Armellini | A61K 9/0063 433/174 |
| 2008/0119945 A1 * | 5/2008 | Frigg | A61B 17/686 623/23.48 |
| 2008/0161934 A1 | 7/2008 | Yamada | |
| 2008/0213729 A1 * | 9/2008 | Hochman | 433/215 |
| 2008/0215010 A1 | 9/2008 | Silver et al. | |
| 2008/0319466 A1 | 12/2008 | Eder | |
| 2009/0181345 A1 * | 7/2009 | Kfir | 433/172 |
| 2009/0208907 A1 | 8/2009 | Dosta et al. | |
| 2009/0318912 A1 * | 12/2009 | Mayer et al. | 606/14 |
| 2010/0042215 A1 * | 2/2010 | Stalcup | A61B 17/68 623/16.11 |
| 2010/0081111 A1 * | 4/2010 | Better et al. | 433/174 |
| 2010/0081112 A1 | 4/2010 | Better et al. | |
| 2010/0221681 A1 * | 9/2010 | Hochman | 433/173 |
| 2010/0255446 A1 * | 10/2010 | Better et al. | 433/174 |
| 2011/0039232 A1 | 2/2011 | Yu | |
| 2011/0143313 A1 * | 6/2011 | Tsai | A61C 8/0006 433/141 |

FOREIGN PATENT DOCUMENTS

| | | |
|---|---|---|
| DE | 10 2008 016 082 A1 | 10/2008 |
| EP | 0 830 852 A1 | 3/1998 |
| EP | 1 195 146 A1 | 4/2002 |
| JP | 7-222752 A | 8/1995 |
| JP | 2003290253 | 10/2003 |
| KR | 20090002375 | 3/2009 |
| RU | 2 199 976 C2 | 3/2003 |
| WO | 2005/055817 A1 | 6/2005 |
| WO | 2007/005614 A2 | 1/2007 |
| WO | 2009/024107 A1 | 2/2009 |

OTHER PUBLICATIONS

International Search Report for corresponding International PCT Application No. PCT/IL2011/000083, dated Jun. 17, 2011, four pages.
https://www.youtube.com/watch?v=uGPYrq83r2E, iRaise Sinus Lift Implant animation, published Jan. 31, 2012.

* cited by examiner

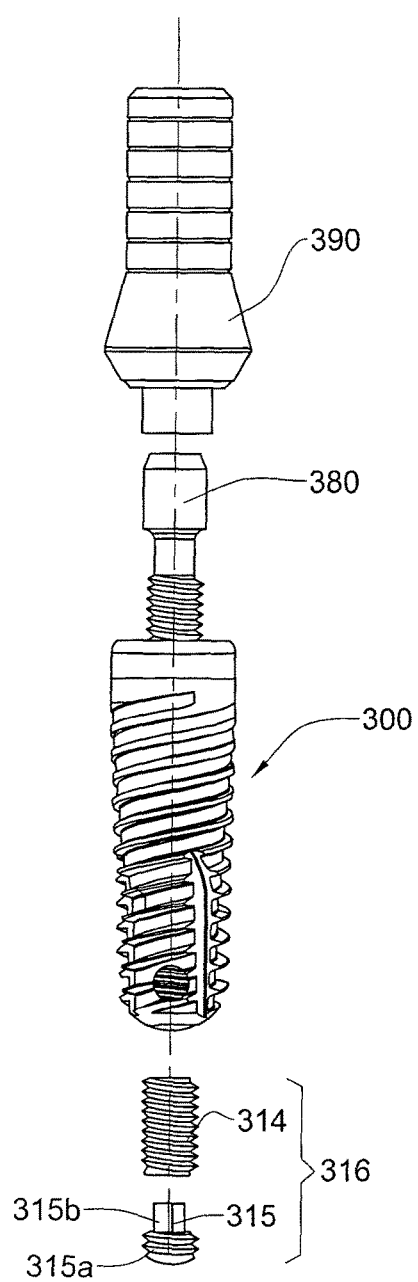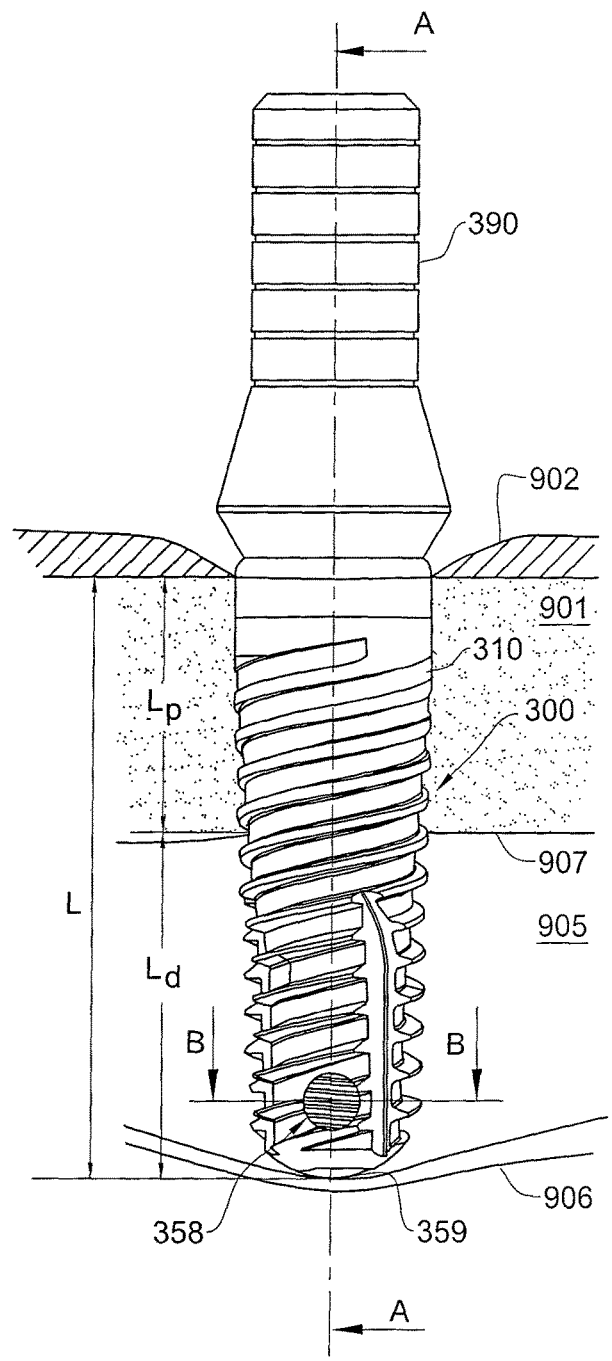
FIG. 7
FIG. 8

SECTION B-B

SECTION A-A

SECTION B'-B'

SECTION A'-A'

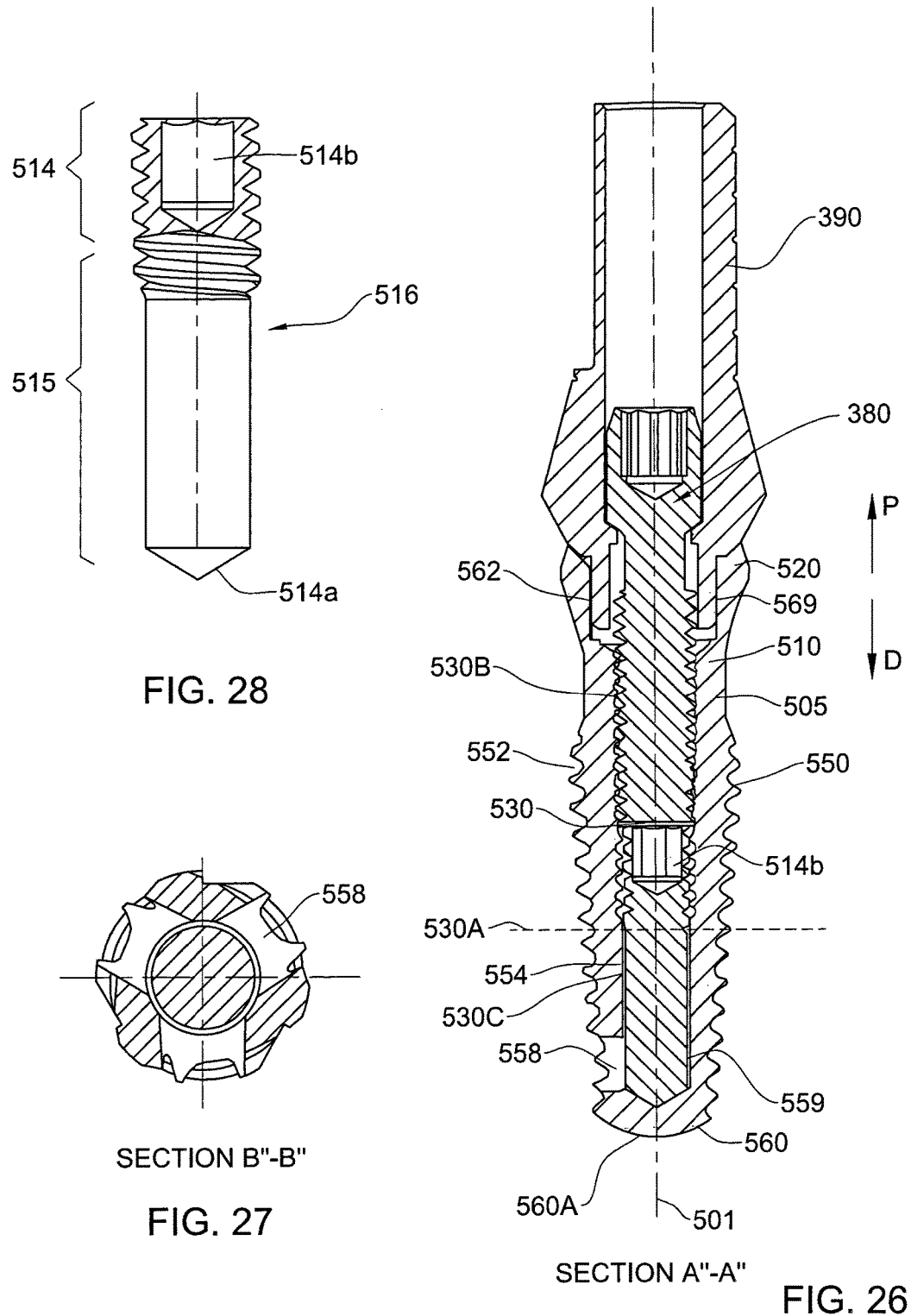

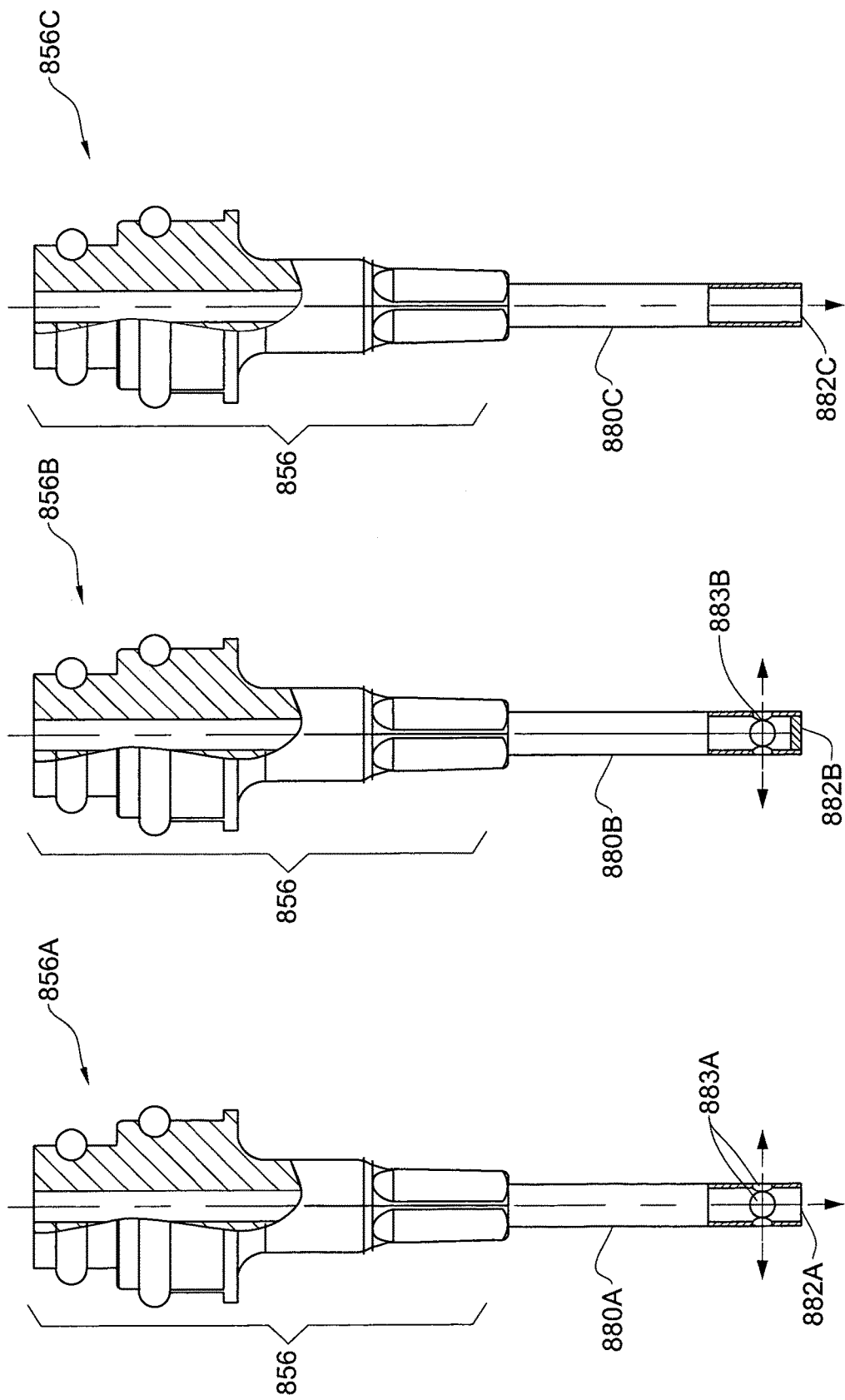

DENTAL IMPLANTS, DEVICES AND METHODS ASSOCIATED WITH DENTAL IMPLANTATION PROCEDURES

This is a National Phase Application filed under 35 U.S.C. § 371 as a national stage of PCT/IL2011/000083, filed on Jan. 25, 2011, an application claiming the benefit under 35 U.S.C. § 119 of U.S. patent application Ser. No. 12/656,341, filed on Jan. 26, 2010, an application claiming the benefit under 35 U.S.C. § 119 of International Application No. PCT/IL2010/000900, filed on Nov. 1, 2010 the content of each of which is hereby incorporated by reference in their entirety.

FIELD OF THE INVENTION

This invention relates to dental implants, devices, systems and methods for use in procedures associated with the intra-oral cavity, in particular with respect to dental implant procedures in general, and specially to sinus augmentation procedures and to nasal augmentation procedures.

BACKGROUND OF THE INVENTION

Conventional dental implant procedures for the upper jaw or maxilla sometimes requires a sinus augmentation procedure to be first implemented, so as to provide sufficient bone to anchor the implant. A commonly used sinus augmentation procedure is performed from inside the intraoral cavity. In what is known as the lateral approach, a lateral incision is made into the gum and gum tissue is pulled back, and an opening is cut in the exposed lateral boney wall of the sinus. The sinus is covered by a thin membrane, which is lifted away to create a space into which allogenic, autogenous, or synthetic bone graft material is inserted via the opening. However, cutting through the boney wall and lifting the membrane can lead to tearing or puncturing of the membrane if not done carefully, and this requires the membrane to be immediately repaired, postponing the sinus augmentation procedure until healing of the membrane is complete. Once the bone graft material has been is integrated in the maxilla, which can normally take between 6 and 12 months, the dental implant can be installed, followed by the dental prosthesis.

Another method sometimes used when there is a minimum of 5 mm involves inserting the bone graft material from the crest of the bone during implant placement, and is known as the crestal approach. The normal implant hole is drilled until about 1 mm before the sinus, and then another tool is used for taping the remaining shell of bone towards the sinus. The tapped shell displaces the membrane into the sinus, making room for the graft material which is then inserted via the implant hole. The implant is then installed into the prepared bone, allowing the graft material to become integrated while anchoring the implant.

By way of general background, US 2009/208907 is directed to a group of dental implants used for two-stage implantation into the alveolar bone.

U.S. Pat. No. 6,840,770 (US 2003/124486) discloses systems and methods for a dental implant system suitable for an endosteal implant into a jawbone. The systems and methods make use of a tapered, expandable polymer sheath insertable into a jawbone, a tapered implant insertable into the sheath and causing expansion of the sheath upon insertion, and an abutment adapted to be coupled to the implant and permitting the attachment of a dental prosthesis.

U.S. Pat. No. 7,510,397 discloses a method and apparatus for providing implants in the upper jaws of a person. A sleeve is inserted through the alveolar ridge to the maxillary sinus. The sleeve is used to initiate separation of the subantral membrane and this is followed by hydrodissection using fluid pressure to form a cavity, with the sleeve remaining in place. A filler, such as a bone growth stimulant is injected through the sleeve into the cavity.

U.S. Pat. No. 6,799,970 (US 2002/177102) discloses a dental implant for anchoring in a bone structure comprising a head intended to support a dental prosthesis and a threaded root of cylindrical substance, in which the threaded root has an internal cavity and a lateral orifice through which this internal cavity opens out on the external lateral face of the root. The axial position of this orifice is such that when the implant is in position, this orifice opens out on a medullary zone of the bone structure.

U.S. Pat. No. 6,042,380 discloses an expandable dental implant which can immediately receive functional loading to support a dental prosthesis upon insertion into the patient's mouth. The expandable implant is constructed as an inflatable balloon.

DE 4321785 discloses a dental implant having a balloon which can be inserted, in particular, in tooth sockets, jaw cavities or artificially created bone cavities, can be filled via a closable filling opening with gas, liquid and/or solid filler materials, can be attached to the jaw or tooth in the region of its filling opening and is provided with an outer layer which can grow on in the bone cavity to be filled.

U.S. Pat. No. 4,671,768 discloses an implant comprising an anchoring part having one or more fixing means as well as a prosthesis part adapted to fix a dental prosthesis, which implant is provided with a cavity extending from the prosthesis part into the anchoring part, the wall of the anchoring part is perforated at one or more spots and the prosthesis part is provided with a removable closing means for the cavity; when the implant is implanted the cavity of the implant may contain a medicine for protecting the implant against pathogenic bacteria etc.

Further by way of general background, WO 2009/024107 discloses a modular endoscope system in which a plurality of connecting pieces, tools and cannulas are assigned to a single lens and are each selected according to the use thereof. The connecting pieces and the cannulas are said to be designed preferably for single use so that only the lens must be decontaminated.

SUMMARY OF THE INVENTION

According to an aspect of the invention, there is provided a dental implant comprising an implant body having a proximal portion configured for enabling a prosthesis to be fixed thereto, the prosthesis comprising a prosthesis mounting arrangement configured for fixing the prosthesis to the implant, said proximal portion having at least one proximal opening, and a distal portion having a distal end and at least one distal opening at or near said distal end, said distal portion configured for being directly implanted with respect to one of the maxilla and mandible, the implant body further comprising at least one internal passageway wherein fluid communication is provided between said at least one proximal opening and at least a first portion of an outside of said distal end via said at least one distal opening and said internal passageway, and further comprising a sealing arrangement different from said prosthesis mounting arrangement and configured for selectively and reversibly closing said fluid communication independently of the prosthesis being fixed or not fixed with respect to the dental implant.

By the sealing arrangement being configured for selectively and reversibly closing said fluid communication independently of the prosthesis being fixed or not fixed with respect to the dental implant, is meant that the aforesaid closing of said fluid communication by the sealing arrangement is independent of whether the prosthesis or any part thereof, for example the prosthesis mounting arrangement, is fixed or not fixed with respect to the dental implant.

For example, the mounting arrangement of the prosthesis may be integral with the prosthesis, or alternatively may comprise an abutment (possibly with an abutment screw) or other interface structure that is used for supporting and retaining the prosthesis on the implant. It is to be noted that said sealing arrangement is also different from any such prosthesis mounting arrangement in the from of an abutment, abutment screw or interface structure, and is configured for selectively and reversibly closing said fluid communication independently of the prosthesis (i.e., or the mounting arrangement thereof) being fixed or unfixed with respect to the dental implant.

The dental implant according to this aspect of the invention and as defined above can comprise one or more of the following features in any desired combination or permutation:

- A. The sealing arrangement can comprise a plug member having a plug distal portion and a plug proximal portion, said plug member being configured for being removably internally accommodated within said passageway in a sealing position to form a seal therewith and to thereby close fluid communication between a passageway distal portion of said passageway including said at least one distal opening, and a passageway proximal portion of said passageway including said proximal opening.
- B. Additionally or alternatively to feature A, at least part of said passageway distal portion is unthreaded and faces a corresponding unthreaded part of said plug distal portion when said plug member is in said sealing position.
- C. Additionally or alternatively to features A to B, at least part of said passageway proximal portion is threaded and cooperates with a correspondingly threaded part of said plug proximal portion at least when said plug member is in said sealing position. For example, said part of said passageway proximal portion extends up to said proximal opening. Optionally, at least one of said unthreaded part of said passageway distal portion and said unthreaded part of said plug distal portion comprises a cylindrical surface, and/or at least one of said unthreaded part of said passageway distal portion and said unthreaded part of said plug distal portion comprises a frusto-conical surface. Optionally, at least one of said unthreaded part of said passageway distal portion sealingly abuts said unthreaded part of said plug distal portion when said plug member is in said sealing position.
- D. Additionally or alternatively to features A to C, said sealing arrangement is configured for selectively and reversibly closing said fluid communication independently of said proximal opening being open or closed.
- E. Additionally or alternatively to features A to D, said distal portion comprises an external screw thread arrangement for directly engaging with tissues of one of the maxilla and mandible for enabling the dental implant to be directly implanted with respect thereto.
- F. Additionally or alternatively to features A to E, said dental implant is further configured to provide a direct line-of-sight (LOS) between said proximal opening and a second portion of said outside distal of said distal end via said passageway, at least in the absence of said sealing arrangement.
- G. Additionally or alternatively to features A to F, said at least one distal opening and said at least one passageway are configured for enabling suitable bone graft material to be inserted therethrough.
- H. Additionally or alternatively to features A to G, said distal end is devoid of sharp or cutting elements.
- I. Additionally or alternatively to features A to H, said distal end comprises a blunt abutment portion.
- J. Additionally or alternatively to features A to I, said sealing arrangement is proximally removable via said proximal opening.
- K. Additionally or alternatively to features A to J, at least one said distal opening is an axial distal opening provided at said distal end, and wherein said axial distal opening, said proximal opening and said passageway are aligned with a longitudinal axis of the dental implant to provide a direct line-of-sight (LOS) between. said axial distal opening and said proximal opening.
- L. Additionally or alternatively to features A to K, said implant is further configured for preventing said plug member from being removed distally from said passageway. Optionally, said passageway comprises a mechanical stop axially cooperating with said plug member for preventing removal of said plug member distally via said distal end.
- M. Additionally or alternatively to features A to I, said at least one distal opening comprises at least one lateral distal opening proximally displaced from said distal end and laterally disposed with respect to said passageway.
- N. Additionally or alternatively to features J to L, said at least one distal opening comprises at least one lateral distal opening proximally displaced from said distal end and laterally disposed with respect to said passageway. Optionally, said plug member is further configured for being removably accommodated within said passageway at a distal position therein such that all of said lateral distal openings are closed thereby from said proximal opening to thereby prevent fluid communication between said proximal opening and said outside via said distal openings; alternatively, said plug member is configured for being removably accommodated within said passageway at a first distal position therein such that said axial distal opening is closed thereby to prevent fluid communication between said proximal opening and said outside via said axial distal opening, and wherein said sealing arrangement further comprises an additional plug member, different from said plug member, and configured for being removably accommodated within said passageway at a second distal position therein such that said lateral distal openings are closed thereby to prevent fluid communication between said proximal opening and said outside via said lateral distal openings.
- O. Additionally or alternatively to features A to I, said distal end is closed and transparent, wherein said proximal opening and said passageway are aligned with a longitudinal axis of the dental implant, and wherein said at least one distal opening comprises at least one lateral distal opening proximally displaced from said distal end and laterally disposed with respect to said longitudinal axis.
P. Additionally or alternatively to features A to O, said plug member is transparent or comprises a transparent window.
Q. Additionally or alternatively to features A to P, said implant body is formed as a unitary item.
R. Additionally or alternatively to features A to Q, said distal end is configured for projecting into a sinus cavity and for directly displacing at least a majority of the corresponding sinus membrane during installation of the dental implant in the maxilla to thereby a create a space between said sinus membrane and a corresponding sinus floor corresponding to a desired sinus augmentation, while providing fluid communication between said at least one distal opening and at least one of said sinus portion and said space.
S. Additionally or alternatively to features A to R, said sealing arrangement is configured for selectively and reversibly closing said at least one distal opening by sealing off a passageway distal portion of said passageway including said at least one said distal opening, from a passageway proximal portion of said passageway. Optionally, said sealing arrangement is configured for maintaining fluid communication between an outside of said implant and said passageway distal portion via said at least one distal opening while concurrently sealing off said passageway distal portion from said passageway proximal portion. Additionally or alternatively, said passageway proximal portion is configured for anchoring therein the dental prosthesis when fixed or mounted to said implant.
T. Additionally or alternatively to features A to S, said sealing arrangement is configured for selectively and reversibly closing said at least one distal opening concurrently with said proximal opening being open.
U. Additionally or alternatively to features A to T, said implant body is made from metallic medically compatible materials and/or from non-metallic medically compatible materials. For example, said metallic medically compatible materials can include titanium and/or stainless steel. For example, said non-metallic medically compatible materials include at least one of material MP-1 developed by NASA, and/or suitable plastics and/or suitable polymers, in particular medical plastics and/or medical grade polymers.
V. Additionally or alternatively to features A to U, said sealing arrangement is made from metallic medically compatible materials and/or from non-metallic medically compatible materials. For example, said metallic medically compatible materials include at least one of titanium and stainless steel. For example, said non-metallic medically compatible materials include at least one of material MP-1 developed by NASA, and/or polyamide, and/or the material PEEK (as marketed by Victrex), and/or other suitable plastics and/or other suitable polymers, in particular medical plastics and/or medical grade polymers.

According to another aspect of the invention, there is also provided a dental implant having an implant body having a proximal portion configured for enabling a prosthesis to be fixed or mounted thereto and having at least one proximal opening, and a distal portion having a distal end and at least one distal opening at or near said distal end, said distal portion configured for being directly implanted with respect to one of the maxilla and mandible, the implant body further comprising at least one internal passageway wherein fluid communication is provided between said at least one proximal opening and at least a first portion of an outside of said distal end via at least one distal opening and said internal passageway, and further comprising a sealing arrangement configured for selectively and reversibly closing said fluid communication independently of said proximal opening being open or closed. In other words, the implant body itself is configured for anchoring a prosthesis to the maxilla or mandible.

The dental implant according to this aspect of the invention and as defined above can comprise one or more of the following features in any desired combination or permutation:

(i) The dental implant as defined above, wherein said dental implant is further configured to provide a direct line-of-sight (LOS) between said proximal opening and a second portion of said outside distal of said distal end via said passageway, at least in the absence of said sealing arrangement. In some embodiments, the first portion of the outside is the same as the second portion of the outside, while in other embodiments, the first portion of the outside is different from the second portion of the outside.

(ii) The dental implant as defined above and/or in combination with feature (i), wherein said at least one distal opening and said at least one passageway are configured for enabling suitable bone graft material to be inserted therethrough. This can facilitate forming a sinus augmentation while the dental implant is installed in the maxilla, for example.

(iii) The dental implant as defined above and/or in combination with any one of features (i) and (ii), wherein said distal end is devoid of sharp or cutting elements. For example, where such sharp or cutting edges could otherwise damage the sinus membrane if in contact therewith.

(iv) The dental implant as defined above and/or in combination with any one of features (i) to (iii), wherein said distal end comprises a blunt abutment portion. For example, the blunt abutment portion can be configured for abutting contact with said sinus membrane.

(v) The dental implant as defined above and/or in combination with any one of features (i) to (iv), wherein said sealing arrangement is proximally removable via said proximal opening.

(vi) The dental implant as defined above and/or in combination with any one of features (i) to (v), wherein at least one said distal opening is an axial distal opening provided at said distal end, and wherein said axial distal opening, said proximal opening and said passageway are aligned with a longitudinal axis of the dental implant to provide a direct line-of-sight (LOS) between. said axial distal opening and said proximal opening.

(vii) The dental implant as defined above and/or in combination with any one of features (i) to (vi), wherein said sealing arrangement comprises a first plug member having a first plug distal end and a first plug proximal end, said first plug member being configured for being removably accommodated within said passageway to form a seal therewith and close fluid communication between a passageway distal portion including said at least one distal opening, and a passageway proximal portion including said proximal opening. Optionally, said first plug distal end is at or in close proximity to said distal end and said implant is further configured for preventing said first plug member from being removed distally from said passageway. For example, said distal end comprises a mechanical stop for preventing displacement of said first plug member distally beyond said distal end.

(viii) The dental implant as defined above and/or in combination with any one of features (i) to (vi), wherein said at least one distal opening comprises at least one lateral distal opening proximally displaced from said distal end and laterally disposed with respect to said passageway.

(ix) The dental implant as defined above and/or in combination with feature (vii), wherein said at least one distal opening comprises at least one lateral distal opening proximally displaced from said distal end and laterally disposed with respect to said passageway.

(x) The dental implant as defined in feature (ix), wherein said first plug member is further configured for being removably accommodated within said passageway at a distal position therein such that all of said lateral distal openings are closed thereby from said proximal opening to prevent fluid communication between said proximal opening and said outside via said distal openings.

(xi) The dental implant as defined in feature (ix), wherein said first plug member is configured for being removably accommodated within said passageway at a first distal position therein such that said axial distal opening is closed thereby to prevent fluid communication between said proximal opening and said outside via said axial distal opening, and wherein said sealing arrangement further comprises a second plug member, different from said first plug member, and configured for being removably accommodated within said passageway at a second distal position therein such that said lateral distal openings are closed thereby to prevent fluid communication between said proximal opening and said outside via said lateral distal openings.

(xii) The dental implant as defined above and/or in combination with any one of features (i) to (v), wherein said distal end is transparent, wherein said proximal opening and said passageway are aligned with a longitudinal axis of the dental implant, and wherein said at least one distal opening comprises at least one lateral distal opening proximally displaced from said distal end and laterally disposed with respect to said passage.

(xiii) The dental implant as defined in feature (xii), wherein said sealing arrangement further comprises a first plug member configured for being removably accommodated within said passageway at a distal position therein such that said at least one lateral distal opening is closed with respect to said proximal opening thereby to prevent fluid communication between said proximal opening and said outside via said lateral distal openings.

(xiv) The dental implant as defined in any one of features (vii) to (xiii), wherein said first plug member is transparent or comprises a transparent window.

(xv) The dental implant as defined above and/or in combination with any one of features (i) to (xiv), wherein said implant body is formed as a unitary item.

(xvi) The dental implant as defined above and/or in combination with any one of features (i) to (xv), wherein said distal end is configured for projecting into a sinus cavity and for directly displacing at least a majority of the corresponding sinus membrane during installation of the dental implant in the maxilla to thereby a create a space between said sinus membrane and a corresponding sinus floor corresponding to a desired sinus augmentation, while providing fluid communication between said at least one distal opening and at least one of said sinus portion and said space.

(xvii) The dental implant as defined above and/or in combination with any one of features (i) to (xvi), wherein said distal portion comprises an external screwthread structure for affixing said distal portion in the maxilla or mandible.

(xviii) The dental implant as defined above and/or in combination with any one of features (i) to (xviii), wherein said sealing arrangement is configured for selectively and reversibly closing said at least one distal opening by sealing off a passageway distal portion of said passageway including said at least one said distal opening, from a passageway proximal portion of said passageway.

(xix) The dental implant as defined in feature (xviii), wherein said sealing arrangement is configured for maintaining fluid communication between an outside of said implant and said passageway distal portion via said at least one distal opening while concurrently sealing off said passageway distal portion from said passageway proximal portion.

(xx) The dental implant as defined in feature (xviii) or feature (xix), wherein said passageway proximal portion is configured for anchoring therein a dental prosthesis fixed or mounted to said implant.

(xxi) The dental implant as defined above and/or in combination with any one of features (i) to (xx), wherein said sealing arrangement is configured for selectively and reversibly closing said at least one distal opening concurrently with said proximal opening being open.

It is to be noted that a feature of at least some embodiments of the invention is that the respective implant facilitates introduction of medication or any other suitable materials into the respective jaw where the implant is implanted, even long after the implantation procedure has been completed. For this purpose, the respective dental prosthesis (and abutment) is removed from the implanted implant. Then, the sealing arrangement is removed to re-open fluid communication between the oral cavity via the proximal opening (that is now open) and the inside of the respective jaw via the distal opening(s) via the internal passageway. A syringe or other suitable delivery system can be used for delivering the required material into the inside of the respective jaw via the passageway, and subsequently the passageway can again be sealed using the sealing system, followed by re-mounting of the dental prosthesis (and abutment). This minimizes or eliminates risk of damage to the implant or to the implantation site, reduces or minimizes risk or discomfort to the patient, and provides for a fast and effective procedure for delivering the required materials to the implantation site. Similarly, this procedure can be instead used for taking a biopsy or other sample of the patient's tissues close to the implantation site via the passageway, and sealing the same afterwards.

According to another aspect of the invention, there is provided a dental implant comprising an implant body having a proximal portion configured for enabling a prosthesis to be fixed or mounted thereto and having at least one proximal opening, and a distal portion having a distal end, said distal portion configured for being directly implanted with respect to the maxilla or mandible, the implant body further comprising at least one internal passageway, wherein said dental implant is further configured to provide a direct line-of-sight (LOS) between said proximal opening and an outside distal of said distal end via said passageway, and wherein said distal end is transparent.

The dental implant according to this aspect of the invention and as defined above can comprise one or more of the following features in any desired combination or permutation:

(I) Optionally, said proximal opening and said passageway can be aligned with a longitudinal axis of the dental implant.

(II) Additionally or alternatively, said at least one distal opening can comprise at least one lateral distal openings proximally displaced from said distal end and laterally disposed with respect to said passage.

(III) Additionally or alternatively, said distal end can be open, and comprises a plug member configured for selectively and reversibly closing said distal end independently of said proximal opening being open or closed, wherein said plug member is transparent or comprises a transparent window.

According to another aspect of the invention, there is provided a method for implanting a dental implant in a maxilla of a dental patient, the maxilla having a paranasal sinus cavity lined with a sinus membrane, the method comprising:

(a) providing the implant, the implant comprising a proximal portion configured for enabling a prosthesis to be fixed or mounted thereto and having at least one proximal opening, and a distal portion having a distal end and at least one distal opening at or in proximity to said distal end, said distal portion configured for being implanted with respect to the maxilla, and further comprising at least one internal passageway providing fluid communication between said at least one proximal opening and said at least one distal opening;

(b) forming a channel through the alveolar ridge of the maxilla, extending from an outside of the maxilla to the sinus floor of the maxilla;

(c) installing the dental implant in the maxilla by inserting the implant via said channel, and concurrently creating a first space between the sinus floor and the sinus membrane, wherein at least a majority of said first space is formed by the distal displacement of said sinus membrane responsive to said distal end being incrementally projected in a direction towards the sinus cavity until the implant is substantially fully seated in its required final position with respect to the alveolar ridge, and wherein fluid communication between the outside of the maxilla and said first space is provided via said at least one passageway and said at least one distal opening; and (d) providing via at least one internal passageway and said at least one distal opening suitable bone graft material to said first space to form a sinus augmentation.

Alternatively, step (c) comprises installing the dental implant in the maxilla by inserting the implant via said channel, and concurrently creating a first space between the sinus floor and the sinus membrane by displacing said sinus membrane from said sinus floor, wherein at least a majority of said sinus displacement is responsive to said distal end being incrementally projected in a direction towards the sinus cavity in abutment with said sinus membrane, and wherein fluid communication between the outside of the maxilla and said first space is provided via said at least one passageway and said at least one distal opening.

The method can further comprise the step of allowing the dental implant to be anchored in situ in said sinus augmentation.

In at least some embodiments, said distal end can comprise a blunt abutment portion that is in abutting contact with said sinus membrane at least during a majority of the displacement of said sinus membrane.

In at least some embodiments, in step (d) sufficient said bone graft material is provided to further displace said sinus membrane wherein to augment said first space with a second space that is at least partially filled with said bone graft material, wherein said sinus augmentation also includes said at least partially filled second space.

In at least some embodiments, the method further comprises the step of sealing said at least one internal passage.

In at least some embodiments, the method further comprises the step of mounting a suitable prosthesis to said implant.

In at least some embodiments, step (b) comprises:
(b1) forming a window in the gingival of the maxilla;
(b2) using a working end of a first tool, removing material from the bone of the alveolar ridge of the maxilla to form said channel extending from said window to said sinus floor, while monitoring said material removal process via a suitable image acquisition system.

Typically, in step (a), said window is formed on a crest portion of the gum.

Optionally, said first tool and said image acquisition unit are included in a suitable device, wherein said image acquisition unit and said tool working end are positioned in the device such said tool working end is in the field of view of said image acquisition unit at least during operation of the first tool. Further optionally, said device is hand-manipulated by the user at least during part of step (b2). Further optionally, step (d) comprises injecting said bone graft material using a second tool included in said device; said second tool can optionally be provided in the form of a syringe having a respective second tool working end in the form of a delivery hose having a distal opening, and wherein said second tool is used for injecting said bone graft material into said first space via said needle opening, and wherein said injection process is monitored in real time via said image acquisition system.

In at least some embodiments, said at least one internal passageway provides a direct line of sight between said at least one proximal opening and said at least one distal opening. The method can further comprise monitoring in real time said displacement of the sinus membrane using an image acquisition system, wherein a part of the sinus membrane in abutment with or in proximity to said distal end is in the field of view of said image acquisition system. In at least some embodiments, the at least one said distal opening is at said distal end and said part of the sinus membrane in abutment with or in proximity to said distal end is in the field of view of said image acquisition unit via said distal opening at said distal end. In at least some embodiments, said distal end is transparent and said part of the sinus membrane in abutment with or in proximity to said distal end is in the field of view of said image acquisition unit via said transparent distal end.

In at least some embodiments, the method further comprises monitoring a color of said part of the sinus membrane and halting the displacement of said sinus membrane when said color is considered to have blanched.

The method can optionally further comprise sealing said at least one passage.

The method according to this aspect of the invention can be extended to a number of implants concurrently implanted in the maxilla with respect to a common sinus cavity. According to such an embodiment, there is provided a method for implanting at least two dental implants in a maxilla of a dental patient, the maxilla having a paranasal sinus cavity lined with a sinus membrane, the method comprising:

(AA) providing the at least two implants, each said implant comprising a proximal portion configured for enabling a prosthesis to be fixed or mounted thereto and having at least one proximal opening, and wherein at least one said implant comprises a distal portion having a distal end and at least one distal opening at or in proximity to said distal end, said distal portion configured for being implanted with respect to the maxilla and further comprising at least one internal passageway providing fluid communication between said at least one proximal opening and said at least one distal opening;

(BB) for each said implant, forming a respective channel through the alveolar ridge of the maxilla, extending from an outside of the maxilla to the sinus floor of the maxilla;

(CC) installing the dental implants in the maxilla by inserting each implant via the respective said channel, and concurrently creating a first space between the sinus floor and the sinus membrane by displacing said sinus membrane from said sinus floor, wherein at least a majority of said sinus displacement is responsive to each said distal end being incrementally projected in a direction towards the sinus cavity in abutment with said sinus membrane, and wherein fluid communication between the outside of the maxilla and said first space is provided via said at least one passageway and said at least one distal opening for each said dental implant; and (DD) providing via at least one internal passageway and said at least one distal opening suitable bone graft material to said first space to form a sinus augmentation.

Alternatively, step (CC) comprises installing the dental implant in the maxilla by inserting the implant via said channel, and concurrently creating a first space between the sinus floor and the sinus membrane, wherein at least a majority of said first space is formed by the distal displacement of said sinus membrane responsive to said distal end being incrementally projected in a direction towards the sinus cavity until the implant is substantially fully seated in its required final position with respect to the alveolar ridge, and wherein fluid communication between the outside of the maxilla and said first space is provided via said at least one passageway and said at least one distal opening.

Optionally, each implant can comprise a passageway to the distal end thereof, so that suitable bone graft material can be provided via each implant to the space.

The above methods and variations thereof can be applied, mutatis mutandis, to implanting one or more dental implants with respect to a nasal cavity lined with a membrane, rather than the aforesaid paranasal sinus cavity lined with a sinus membrane.

According to other embodiments of the invention, there is provided a dental implant installation procedure wherein a distal end of a dental implant is projected into one of the paranasal sinus cavity and the nasal cavity to thereby directly displace the respective sinus membrane or nasal cavity membrane from the respective cavity floor and thereby form a space between the respective membrane and the respective cavity floor, while minimizing risk of damaging the respective membrane, and introducing bone graft material into said space via a distal portion of the dental implant to form a sinus augmentation. The implant abuttingly contacts and displaces the respective membrane until the implant is fully seated in the bone, after which said bone graft material is introduced into said space.

According to this aspect of the invention, there is also provided a method for implanting a dental implant in a mandible of a dental patient:

(a) providing the implant, the implant comprising a proximal portion configured for enabling a prosthesis to be fixed or mounted thereto and having at least one proximal opening, and a distal portion having a distal end, said distal portion configured for being implanted with respect to the mandible, and further comprising at least one internal passageway providing at least optical communication between said at least one proximal opening and said distal end, wherein said distal end is configured for enabling a distal outside of said distal end to be observed via the distal end;

(b) forming a channel through a portion of the depth of the mandible, extending from an outside of the mandible;

(c) installing the dental implant in the mandible by inserting the implant via said channel, and concurrently monitoring said implant installation via said distal end.

According to another aspect of the invention, there is provided a dental implant for use in a maxilla, comprising a proximal portion configured for enabling a prosthesis to be fixed or mounted thereto and having at least one proximal opening, and a distal portion having a distal end and at least one distal opening at or in proximity to said distal end, said distal portion configured for being implanted with respect to the maxilla, and further comprising at least one internal passageway providing fluid communication between said at least one proximal opening and said at least one distal opening, wherein said distal end is configured for projecting into a sinus cavity and for directly displacing at least a majority of the corresponding sinus membrane during installation of the dental implant in the maxilla to thereby a create a space between said sinus membrane and a corresponding sinus floor corresponding to a required sinus augmentation, while providing fluid communication between said at least one distal opening and at least one of said sinus portion and said space.

The said at least one distal opening and said at least one passageway can be configured for enabling suitable bone graft material to be inserted therethrough to form said sinus augmentation while the dental implant is installed in the maxilla.

The distal end is devoid of sharp or cutting elements that could otherwise damage the sinus membrane if in contact therewith.

Optionally, said distal end is transparent, wherein said proximal opening and said passageway are aligned with a longitudinal axis of the dental implant, and wherein said distal portion comprises one or a plurality of said distal openings proximally displaced from said distal end and laterally disposed with respect to said passage.

The proximal opening and said passageway can be aligned with a longitudinal axis of the dental implant, and said distal portion can further comprise one or a plurality of additional said distal openings proximally displaced from said distal end and laterally disposed with respect to said passage.

The distal end can comprise a blunt abutment portion configured for abutting contact with said sinus membrane.

The dental implant can further comprise a plug member for selectively sealing said passage.

The distal portion can comprise an external screw thread structure for affixing said distal portion in the alveolar bone of the maxilla.

According to this aspect of the invention, there is also provided a dental implant for use in a mandible, comprising a proximal portion configured for enabling a prosthesis to be mounted thereto and having at least one proximal opening, and a distal portion having a distal end, said distal portion configured for being implanted with respect to the mandible, and further comprising at least one internal passageway providing at least optical communication between said at least one proximal opening and said distal end, wherein said distal end is configured for enabling a distal outside of said distal end to be observed via the distal end to at least allow monitoring of said implant installation via said distal end. One or more distal openings can be provided, and thus the passageway can also be used to provide bone graft material, medication or any other suitable material, as can be desired, to the mandible via the distal openings.

According to an aspect of the invention there is provided a dental implant for facilitating viewing an outside of a distal end thereof via a proximal opening thereof, and/or for providing bone graft material via selectively closable one or more distal openings. A dental implant installation procedure is also provided in which a distal end of a dental implant is projected into a paranasal sinus cavity or a nasal cavity to thereby displace the respective sinus membrane or nasal cavity membrane from the respective cavity floor, while minimizing risk of damaging the respective membrane. Bone graft material is introduced into the space thereby created between the respective membrane and the respective cavity floor via a distal portion of the dental implant to thereby form a desired sinus augmentation.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1a illustrates one mode of operation of the tip of the embodiment of FIG. 1.

FIG. 5(a) schematically illustrates a cross-section of a patient's maxilla; FIG. 5(b) schematically illustrates a channel formed in the maxilla of FIG. 5(a); FIG. 5(c) schematically illustrates a dental implant installed in the maxilla of FIG. 5(b); FIG. 5(d) schematically illustrates the dental implant of FIG. 5(c) fully inserted into the maxilla to create a space; FIG. 5(e) schematically illustrates bone graft material being introduced in the space of FIG. 5(d); FIG. 5(f) schematically illustrates a prosthesis mounted to the dental implant of FIG. 5(e).

FIG. 6(a) schematically illustrates a cross-section of a patient's maxilla; FIG. 6(b) schematically illustrates two dental implants fully installed in the maxilla of FIG. 6(a) to create a space; FIG. 6(c) schematically illustrates bone graft material being introduced in the space of FIG. 6(b); FIG. 6(d) schematically illustrates prostheses mounted to each of the dental implants of FIG. 6(c).

FIG. 7 illustrates in exploded side view, a dental implant according to a third embodiment of the invention.

FIG. 8 illustrates, in side view, a dental implant according to the embodiment of FIG. 7.

in FIG. 14(a), the tool is being used to manipulate the distal plug of the embodiment of FIG. 12; in FIG. 14(b), the tool is being used to manipulate the proximal plug of the embodiment of FIG. 7.

FIG. 26 illustrates, in transverse cross-sectional view, a dental implant according to the embodiment of FIG. 25 along section A"-A".

FIG. 27 illustrates, in cross-sectional view, a dental implant according to the embodiment of FIG. 25 along section B"-B".

FIG. 28 illustrates in isometric view an alternative embodiment of the plug of the embodiment of FIG. 24.

FIG. 31 illustrates in partially sectioned side view a modification of the embodiment of FIG. 30.

FIG. 32 illustrates in partially sectioned side view another modification of the embodiment of FIG. 30.

FIG. 33 illustrates in partially sectioned side view another modification of the embodiment of FIG. 30.

DETAILED DESCRIPTION OF EMBODIMENTS

Herein the term "distal" (D) herein refers to a direction generally away from the user of the device (i.e., the person installing the implant on the dental patient), while the term "proximal" (P) refers to a direction opposed to distal, that is, a direction generally towards the user of the device. Additionally or alternatively, the distal direction (D) herein refers to a general direction from the intra-oral cavity towards the inside of the maxilla (or towards the inside of the mandible, depending on the specific case) of the dental patient, while the proximal direction (P) is in a direction opposed to the distal direction.

Figure 1:
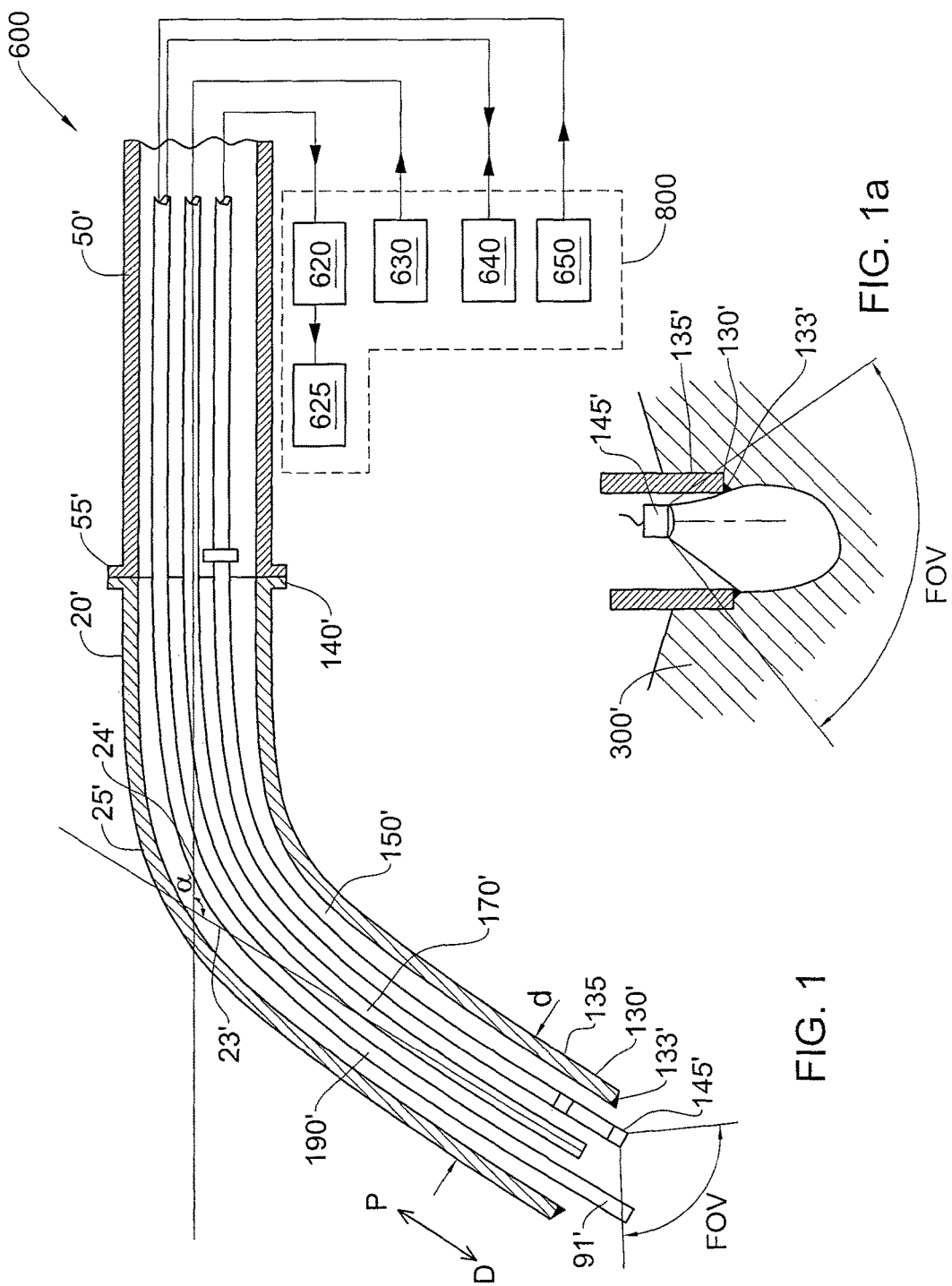
FIG. 1 illustrates, in transverse cross-sectional view, a device according to an embodiment of the invention.

Referring to FIG. 1 and FIG. 1a, an embodiment of a device, generally designated 600, comprises handpiece 50' and a probe member 20' axially mounted thereto and connected to the handpiece 50' via a Luer lock, bayonet fit or any other suitable connection 55'.

The device 600 is configured for carrying out a variety of procedures, including dental procedures, and in particular dental implant procedures and sinus augmentation procedures, as will become clearer herein.

The probe member 20' has an elbow 25' to define angle α between the central axis 23' of the probe at the distal end 130' and the central axis 24' at the proximal end 140', which is co-axial with the longitudinal axis of the handpiece 50'. The probe member 20' has a central passageway 150' between the open distal end 130' and the open proximal end 140'. Passageway 150' extends through handpiece 50' and collectively functions as: (a) a treatment channel for accommodating one or more tools; (b) as an illumination channel for accommodating an illumination arrangement for illuminating the area being worked on by such tool or tools; and (c) as a light collection channel for acquiring images of this area. The device 600 thus further comprises an image acquisition unit 145', which in this embodiment can comprise a CCD or the like, accommodated at or near the distal end of the distal portion 135' of the probe member 20', and operatively connected, for example via cables, to a suitable image acquisition system 620, which can also be configured for displaying images thereby acquired via a suitable image analysis and display unit 625. In at least some such embodiments, the CCD can be disposable together with at least the probe member 20' after use of the device 600 with a patient.

The image acquisition unit 145' comprises a field of view (FOV), and the device 600 is configured such that at least during operation of the device, the working end 91' of a particular tool 190' (that is accommodated in the passageway 150') and that projects distally from the distal end of the distal portion 135', is in this field of view. The field of view of the image acquisition unit 145' in this embodiment is about 120°, and this can be achieved, form example, by providing a suitable 120° convex lens at the distal end of the distal portion 135' in optical communication with the image acquisition unit 145'. In alternative variations of this embodiment, the image acquisition unit 145' can have a different field of view, for example greater than about 90°, for example 180°, or indeed much narrower FOV, for example 60°, or 50°, or 40°, or 30°, or 20° or 10°.

A suitable illumination arrangement 170' can be provided via the passageway 150', and comprises a light guide which for example can be in the form of a plurality of optical fibers accommodated within the probe member 20', having a proximal end configured for optical coupling to a suitable light source system 630, and a distal end via which illuminating light from the light source is transmitted to the tissue being worked on during operation of said device. Thus, the light guide can comprise a multi-fiber wave guide, having, by way of non-limiting example, a diameter of between about 300 micron to about 350 micron accommodating about 3000 optical fibers or more.

Any suitably shaped tool can be inserted into the central passageway 150' such that a distal working end 91' of the tool can be projected into the tissue being worked on via the distal end 130'. Such a tool can comprise, for example, a suitable dental file or reamer, which can be made from nickel titanium or stainless steel for example.

Other tools which can be used via the central passageway 150', can include, by way of non-limiting example, a laser energy delivery system, such as a laser cutting tool, a grasping tool such as micro tongs or a magnetized grasping tool, inter alia, wherein the working portion of the tool projects distally from the distal end of the device at least during operation of the device.

Alternatively, such a tool can be a powered tool, for example a dental drill or reamer, and can comprise, for example, diamond drills or tungsten drills, configured for drilling into bone such as in the maxilla, for example. The working portion 91' of the tool, i.e. the portion of the tool that interacts with the dental tissues, projects distally away from the distal end of the distal end 130'.

Alternatively, the tool can comprise a syringe 640 having a syringe needle of suitable dimensions and flexibility that can be inserted into the central passageway 150' and optionally extend therethrough such that the working portion, i.e., the tip of the syringe needle comprising the syringe outlet, projects from the distal end 130', and enables a desired agent to be delivered to the area being worked on (and/or for fluids to be sucked therefrom) via the syringe at least during operation of the device. Such an agent can comprise, by way of non-limiting example, bone graft material, irrigating solutions, antibiotics, liquid filler, liquid sealant, and so on, inter alia.

As already mentioned, the tool can comprise, for example, a dental laser tool, and such tools are well known in the art. For example, a suitable laser light guide, such as for example one or a plurality of suitable optical fibers, can be passed through the central passageway 150' to the distal end 130', and the proximal end of the optical fiber(s) is optically coupled to a suitable laser radiation generator 650, for example an Erbium laser light source, via suitable optical couplers. Alternatively, the laser tool can comprise a hollow wave guide, coupled to the laser source, and sealed at the distal end thereof by a sapphire tip, which is shaped to direct the laser radiation in the required direction to the area to be treated, for example axially or at an angle to axis 23', where the distal end of the hollow wave guide is wedge-shaped at a suitable wedge angle. Such a hollow wave guide can be, by way of example, of diameter about 100 micron to about 160 micron.

In another example, the tool can be a suitable ultrasonic tool or an RHF cutting tool. Ultrasonic cutting tools are known in the art and can comprise, for example, a piezo electric or electromagnetic source for providing the high energy vibrations required for operation of the tool. Some examples of such ultrasonic cutting tools can include: the Enac device, produced by Osada (Japan); the Satalec device, produced by Aceteon Group, (France); the EMS ultrasonic device, produced by EMS (Switzerland); the Varios 750 device, by NSK (Japan); the Miniendo II device produced by Sybron Dental (USA). RHF cutting tools are also known, for example diathermic devices (monopolar, bipolar, RHF) and can be used for cutting through dental soft tissues. By way of non limiting example, such a device can include the Erbotom 80 device, produced by ERBE (Germany).

Furthermore, additional tools including an irrigation and/or suction catheter can be provided via the passageway 150'.

In this embodiment, the distal end 130' is also optionally configured for use as a cutting or boring tool. For this purpose, a distal edge 133' projects beyond the distal end 130' of the probe, and the distal edge 133' can be sharp, serrated, or abrasive, and this feature of the device 600 is used by manually manipulating the device 600 to provide a material removal action with this edge in contact with a tissue surface, for example. Operation of this tool can be monitored in real time via the image acquisition unit 145' and system 620, which keeps the distal edge 133', i.e., the working end of the tool, in the field of view thereof by retracting the image acquisition unit 145' into the passageway until the distal edge 133' comes into view (FIG. 1a). The probe member 20', or at least the distal portion 135', can be made from a transparent material which further aids in monitoring the operation of the edge 133' with respect to tissue 300' that is being worked on by the tool.

In alternative variations of this embodiment, the distal edge 133' defines the distal end of the probe, and the working end of the tool is within the field of view of the image acquisition unit 145' by retracting the image acquisition unit 145' into the passageway until the distal edge 133' is within the FOV and comes into view. Alternatively, no retraction can be needed, and the image acquisition unit is provided with a very wide field of view, for example 180°.

Image data collected by the imaging system 620 can be communicated to image analysis and display unit 625, for example a computer, for analysis and display. The imaging system 620 can provide discrete images of the said internal surfaces as required, and/or can provide a sequence of such images in real time providing a video stream that can be viewed by the user of the device (typically a dental surgeon) and/or any other observer. Optionally, such images can also be recorded in a memory or any suitable recording device.

The device 600 can be fully disposable, i.e., can be made from materials that render the device disposable after use with one patient or that permit such disposability from an economic perspective, for example. Alternatively the probe member or at least the distal portion thereof are disposable, and are releasably connected to the hand piece 50' or the remainder of the probe member, respectively, in a suitable manner. Alternatively, the device, or the probe member, or at least the distal portion thereof, can be provided with a suitable sheath (not shown) for protecting the device from contamination during use, and the sheath is disposed of after use with a patient.

Alternatively, the device 600 can be sterilizable, for example by autoclaving, and components thereof sensitive to such sterilization are removable therefrom prior to any such operation.

According to a first aspect of the invention, there is provided a dental implant which while being particularly useful for implantation in the maxilla of a patient can also be particularly useful for implantation in the mandible of a patient.

Figure 2:
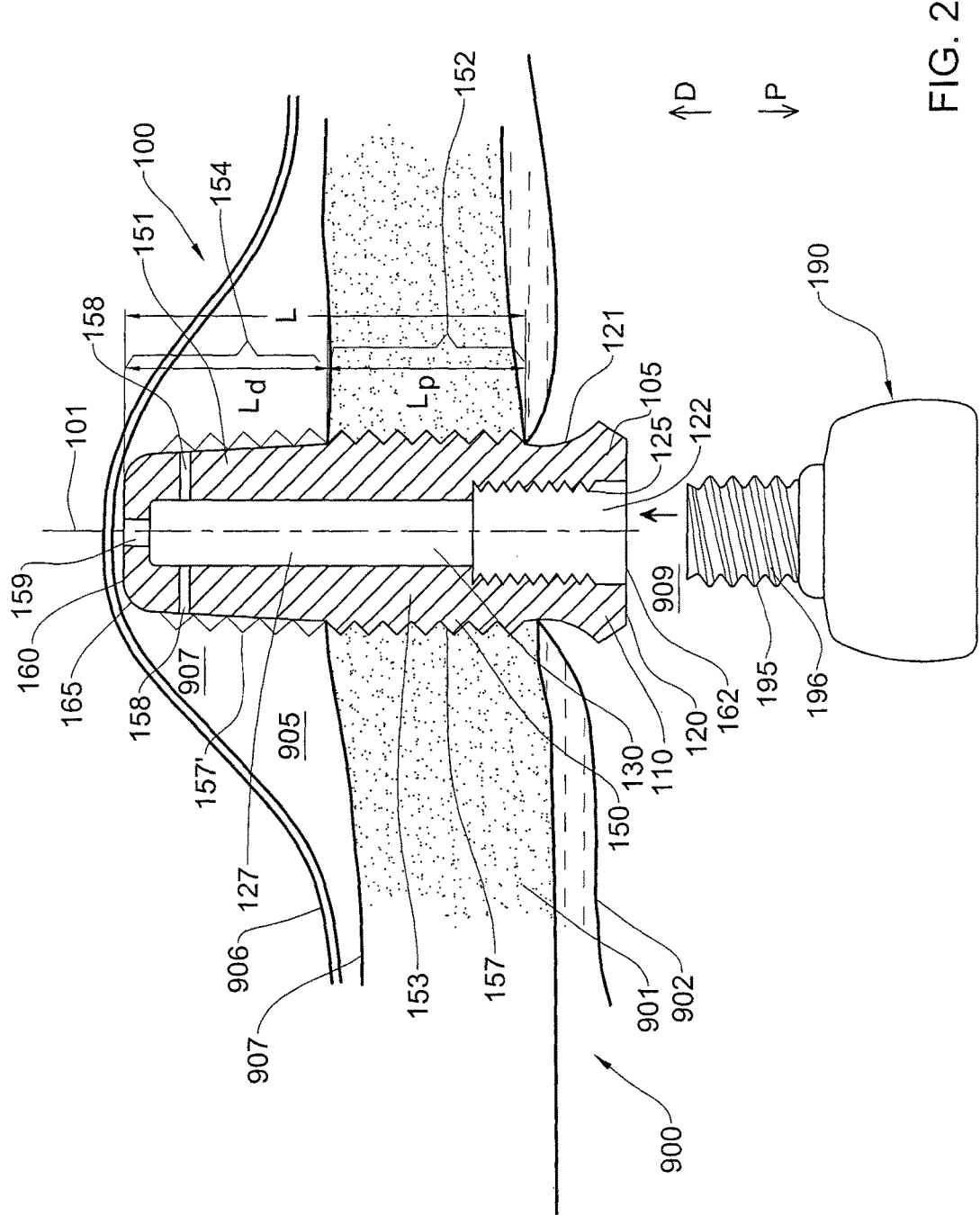
FIG. 2 illustrates, in transverse cross-sectional view, a dental implant according to a first embodiment of the invention.

Referring to FIG. 2, a first embodiment of a dental implant according to this aspect of the invention, generally designated with the numeral 100, is in the form of a generally tubular body 105, comprising a proximal portion 110 having a proximal end 120, a distal portion 150 having a distal end 160, and a generally rectilinear lumen or passageway 130 longitudinally extending through the proximal portion 110 and the distal portion 150.

The proximal portion 110 is configured for enabling a prosthesis 190 having a prosthesis mounting arrangement 196 to be fixed or mounted (fixed and mounted being used interchangeably herein) to the implant 100, and thus comprises a head 121 that is configured for mounting therein the particular prosthesis 190 using any suitable prosthesis engagement arrangement. For example, such a prosthesis engagement arrangement can comprise an internal bore 122 comprising internal threads 125 that are configured to be engaged with the external threads 195 of the prosthesis mounting arrangement 196, which projects distally from the distal end of the prosthesis 190. It is evident to the skilled practitioner that other and different prosthesis engagement arrangements can be provided in the proximal portion 110 according to the specific configuration of the prosthesis mounting arrangement 196.

The distal portion 150 is configured for being implanted in the maxilla 900 of a patient, and comprises a proximal part 152 and a distal part 154. The distal portion 150 has a dimension L along the longitudinal axis 101 of the implant 100 of sufficient magnitude, such that in the implanted position of the implant 100, the distal part 154 of the distal portion 150, including the distal end 160, projects through the alveolar ridge 901 and away from the sinus floor 907 in the direction towards the sinus cavity 910, while the proximal part 152 is anchored in the bone of the alveolar ridge 901 of the maxilla 900. In the aforesaid "implanted position", the implant 100 is at its maximal desired distal position with respect to the maxilla, illustrated in FIG. 2, so that the proximal portion 110 is at the desired permanent position with respect to the maxilla 900 to receive the prosthesis 190.

The proximal part 152 is thus configured for being engaged and secured to the alveolar ridge 901, and in this embodiment comprises a cylindrical body portion 153 having self-tapping external threads 157 having a cylindrical outer profile and configured for cutting into the alveolar bone and securing the dental implant 100 with respect thereto. In alternative variations of this embodiment, the body portion 153 can instead be non-cylindrical, for example frustoconical or any other suitable shape, and/or the external threads 157 can instead be non-tapping, and/or the external threads can have a non-cylindrical outer profile, for example frustoconical or any other suitable shape. In any case, the external threads 157 can have any suitable cross-sectional profile, as is known in the art to secure the proximal part 152 in the alveolar bone.

Thus, the longitudinal length $L_p$ of the proximal part is correlated and generally corresponds to the depth of the alveolar ridge 901, up to the sinus cavity 905, and for example, this longitudinal length $L_p$ can be between about 2 mm and about 8 mm.

The distal part 154 has a longitudinal length $L_d$ that projects into the sinus cavity 906, and represents the minimum depth of the sinus augmentation that is formed by means of the dental implant 100, as will become clearer below.

Thus dimension L is the sum of longitudinal length $L_p$ and longitudinal length $L_d$. Distal part 154 is, in this embodiment, generally tubular, having a generally cylindrical outer form. In alternative variations of this embodiment, the distal part 154 can instead be non-cylindrical, for example frustoconical or any other suitable shape. Optionally, external threads 157 continue on the distal part 154, as shown in phantom lines 157' in FIG. 2.

Figure 3:
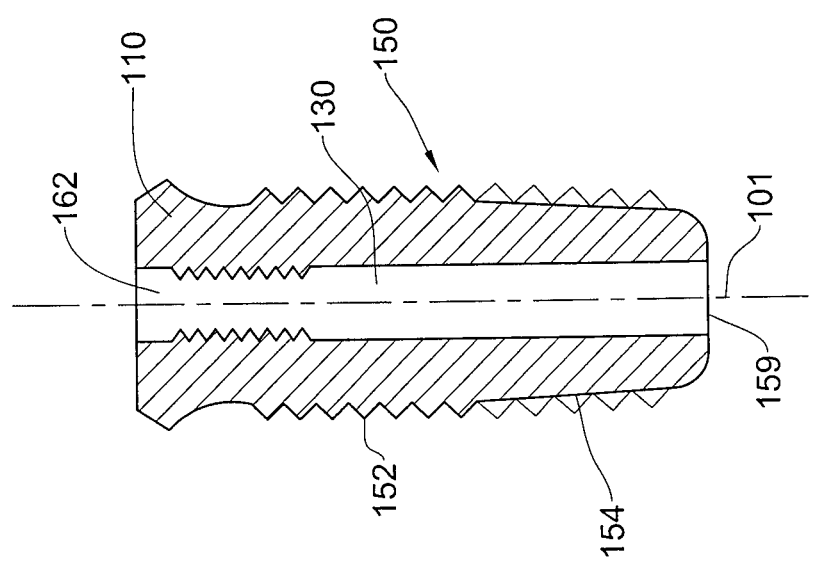
FIG. 3 illustrates, in transverse cross-sectional view, a dental implant according to a variation of the embodiment of FIG. 2.

Distal part 154 comprises a plurality of distal openings 158, 159 providing fluid communication between the passageway 130 and an outside 907 of the distal part 154. One or a number of lateral distal openings 158, for example 2, 3, 4 or more openings, are provided around a periphery of the distal part 154 and are generally lateral-facing, though one or more such openings 158 can optionally have an axis through the respective opening that be inclined at least with respect to the longitudinal axis 101, and are located on the cylindrical wall 151 of the distal part 154, for example close to but proximal to the distal end 160. A single axial distal opening 159 is provided at distal end 160, aligned with the axis 101, though in alternative variations of this embodiment a plurality of such openings can be provided at distal end, and one or none such openings can be aligned with axis 101. The dental implant 100 also comprises a proximal opening 162, which provides fluid communication between the passageway 130 and an outside 909 of the proximal portion 110. In this embodiment, the well 122 forms a proximal part of the passageway 130, and is thus aligned with the axis 101, and a distal part 127 of the passageway 130, also aligned with the axis 101, has a smaller internal diameter than well 122. Thus, proximal opening 162 and distal openings 158, 159 provide fluid communication between an outside of proximal portion 110 and an outside of the distal part 154 via well 122 and distal part 127, i.e., passageway 130. As illustrated in FIG. 3, in an alternative variation of the first embodiment, the lateral distal openings 158 are omitted, and part 154 only comprises an axial distal opening 159 at distal end 160.

Furthermore, in the embodiments of FIG. 2 and FIG. 3, there is a direct line-of-sight (LOS) between the proximal opening 162 and distal opening 159 along axis 101. In at least some alternative variations of the embodiments of FIGS. 2 and 3, in which a plurality of distal openings can be provided at the distal end 160, there is a direct line-of-sight (LOS) between the proximal opening 162 and one or each one of a portion of, or indeed all of, such distal openings. In these or other alternative variations of the embodiments of FIGS. 2 and 3, a plurality of separate passageways can be provided in the body of dental implant, each providing fluid communication between outside 909 and outside 907, via one or more openings 158 and/or 159, and via common proximal opening 162, or via one of a plurality of proximal openings provided at or near the proximal end 160 or via one of a plurality of proximal openings provided into well 122.

In at least some alternative variations of the embodiments of FIGS. 2 and 3, the distal end, and/or a section of the distal part 154 close to the distal end 160 can be formed as a mesh or net, wherein the openings of the mesh or net constitute said distal openings.

Distal end 160 has a blunt form, and is devoid of any sharp, serrated or otherwise cutting surfaces, edges, protrusions or other surface features that are otherwise configured for cutting, slicing or puncturing tissue, especially tissue such as the sinus membrane 906 of the maxilla 900. In the illustrated embodiment, the distal end 160 has a relatively flat surface, with a beveled edge 165, though in alternative variations of the first embodiment the distal end can be convexly curved or have any other suitable shape that minimizes risk of damage to the sinus membrane when in contact with the distal end 160 and when raised thereby.

The dental implant 100 according to the first embodiment and of at least some alternative variations thereof can be formed as a unitary piece or from several components suitably joined together, and made from one or more suitable and biocompatible materials, for example metallic medically compatible materials such as for example titanium and/or stainless steel, and/or for example non-metallic medically compatible materials such as for example material MP-1 developed by NASA and/or other suitable plastics and/or other suitable polymers, or example.

The implant 100 can optionally be configured for sealingly closing the passageway 130, for example by means of a sealing fit between the prosthesis 190 (or a temporary abutment that is engaged to the implant 100 during the healing process).

In alternative variations of this embodiment (and in other embodiments, for example as will be disclosed in greater detail hereinbelow), the passageway 130, or at least the distal part 127 thereof (i.e. the distal openings thereof), can be sealed independently of the prosthesis 190 (or temporary abutment) or of the prosthesis mounting arrangement 196, i.e., the distal openings can be closed independently of the proximal opening being open (no prosthesis installed) or closed (prosthesis installed), i.e., independently of the prosthesis being mounted or unmounted (i.e., fixed or not fixed) with respect to the dental implant, thereby closing fluid communication between the outside 907 and the outside 909, preventing ingress of contaminants to the maxilla (or mandible in respective embodiments) from the intra oral cavity 915, and preventing egress of bone tissue, bone graft material, etc from the maxilla implantation site. Thus, referring to FIG. 2(a), in one such variation of this embodiment a plug 106 (different from prosthesis mounting arrangement 196) is provided that is selectively and sealingly engageable with the distal part 127 of central passageway 130 via complementary screw threads 111, 112 respectively. Plug 106 can comprise a slit 113 that aids the user in manipulating the plug 106 (for example by using a suitable screwdriver) to selectively insert the same into the distal part 127, and thereafter rotate the plug 106 to engage the same therein. Thus, it is readily apparent that plug 106 can be selectively and reversibly operated to close fluid communication via the passageway between the proximal opening and the distal openings, independently of the proximal opening itself being open or closed, or independently of the prosthesis being mounted or unmounted (i.e., fixed or not fixed) with respect to the dental implant. It is also to be noted that plug 106 can be removed proximally from the passageway 130 via the proximal opening.

Figure 2A:
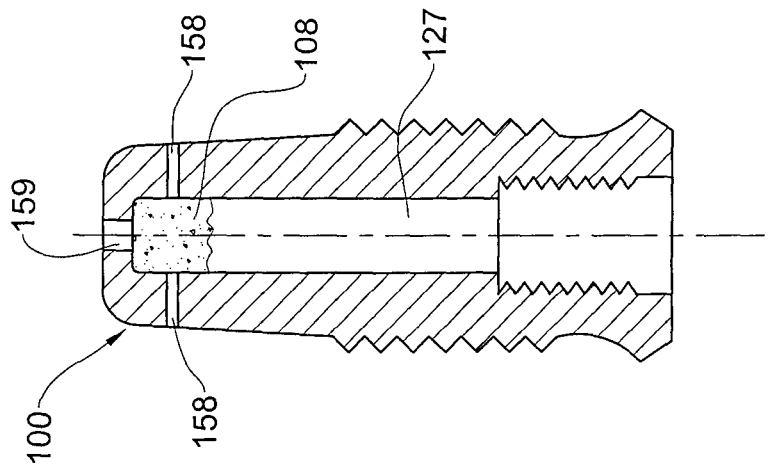
FIGS. 2(a), 2(b) and 2(c) illustrate alternative sealing arrangements for the embodiment of FIG. 2.
Figure 2B:
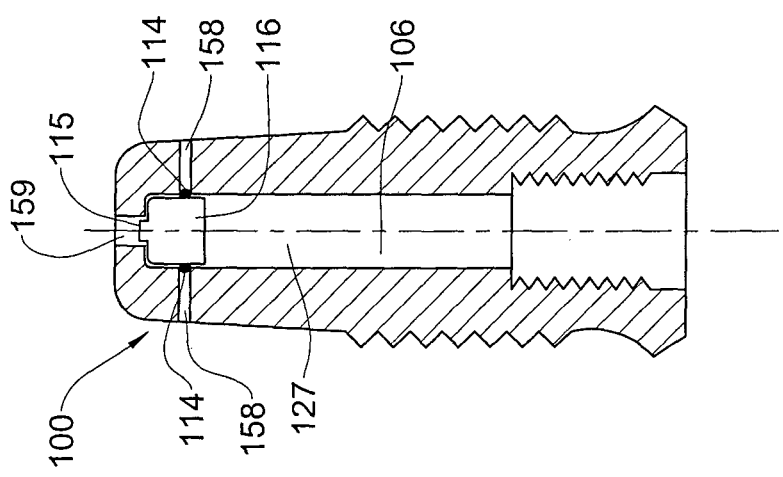

Alternatively, and referring to FIG. 2(b), in another variation of this embodiment a plug 107—again, different from prosthesis mounting arrangement 196—is provided that is selectively and sealingly engageable with the distal end of distal part 127 of central passageway 130. Plug 107 comprises a plurality of projections 114 and 115 resiliently formed on or mounted to the outer cylindrical surface and distal end, respectively, of the plug body 116. The projections 114 and 115 are configured for being inwardly deflected as the plug 107 is moved distally in the distal part 127 and spring back and are at least partially accommodated in corresponding distal openings 158, 159, respectively when the plug 107 reaches the distal end of the distal part 127, thereby sealing the distal openings 158, 159 and distal part 127.

Figure 2C:
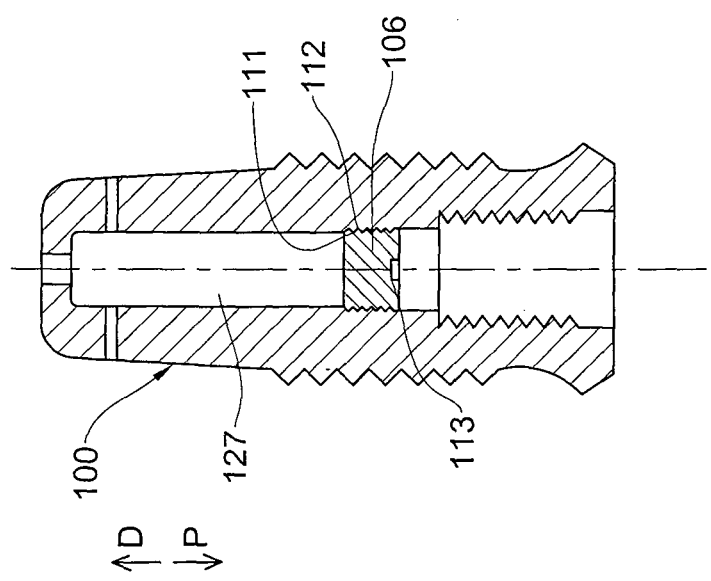

Alternatively, and referring to FIG. 2(c), in another variation of this embodiment a plug 108 is formed in situ by selectively injecting a suitable sealing material, such as for example dental glue, to thereby sealingly plug the distal end of distal part 127 of central passageway 130, either proximal to the distal openings 158, 159 or including distal openings 158, 159.

Figure 4:
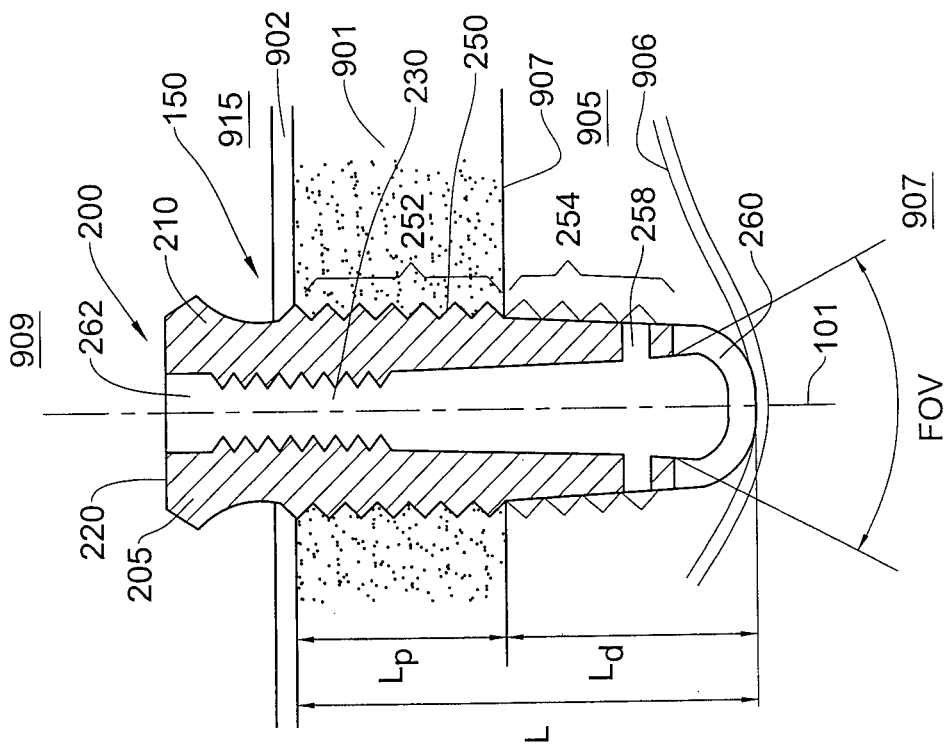
FIG. 4 illustrates, in transverse cross-sectional view, a dental implant according to a second embodiment of the invention.

A second embodiment of the dental implant according to this aspect of the invention, generally designated with the reference numeral 200, is illustrated in FIG. 4 and comprises all the elements and features of the first embodiment of FIG. 2 and at least some alternative variations thereof, though with some differences as will become clearer herein. Thus, implant 200 is also in the form of a generally tubular body 205, comprising a proximal portion 210 having a proximal end 220 and opening 262, a distal portion 250 comprising a proximal part 252 and a distal part 254, and having a distal end 260 and one or more distal openings 258, and a lumen or passageway 230 longitudinally extending through the proximal portion 210 and the distal portion 250, respectively corresponding to tubular body 105, proximal portion 110, proximal end 120, opening 162, distal portion 150, proximal part 152, distal part 154, distal end 160, distal openings 158, and passageway 130 of the first embodiment, mutatis mutandis.

However, in the second embodiment, there is no axial distal opening at the distal end 260 corresponding to axial distal opening 159 of the first embodiment, and thus, proximal opening 262 and lateral distal openings 258 provide fluid communication between an outside of proximal portion 210 and an outside of the distal part 254 via passageway 230.

In the second embodiment, at least the closed distal end 260 is made from a transparent material, that is also biocompatible, such as for example glass or a suitable transparent polymer, or any other suitable material—for example a sapphire stone-thereby providing a direct line-of-sight (LOS) from the proximal opening 262 and through the distal end 260 along axis 101. The remainder of the implant 200 can be made from an alternative material, for example metallic medically compatible materials such as for example titanium and/or stainless steel, and/or for example non-metallic medically compatible materials such as for example material MP-1 developed by NASA and/or other suitable plastics and/or other suitable polymers, for example.

In the second embodiment, the distal end 260 also has a blunt form, and is devoid of any sharp, serrated and/or otherwise cutting surfaces, edges, protrusions and/or other surface features that are configured for cutting, slicing and/or puncturing tissue, especially tissue such as the sinus membrane 906 of the maxilla 900, similarly to the distal end 160 of the first embodiment of the implant 100, mutatis mutandis. In the second embodiment illustrated in FIG. 4, the distal end 260 has a convex surface, for example a hemispherical surface, and thus acts an optical lens increasing the field of view (FOV) when observing the outside of the distal end 260 from inside the passageway 230. The curvature of the distal end 260 can be chosen to be such as to provide any desired FOV, for example the distal end can be fully hemispherical, thereby providing a FOV similar to that of a fish-eye lens with a FOV of about 180°. In alternative variations of this embodiment, the distal end can be configured for providing a FOV of about 120°, or 90°, or 50°, or any other desired FOV. In alternative variations of the second embodiment the distal end 260 can have a relatively flat surface, with a beveled peripheral edge, or have any other suitable shape.

The direct line of sight between the proximal end of the implant and the environment distal of the distal end provided by the implant according to the first aspect of the invention, for example at least some of the disclosed embodiments thereof, can also be useful in other dental procedures, such as for example when installing such an implant in the mandibular jaw in which the risks of damaging the inferior alveolar nerve in the mandibular canal are minimized by virtue of enabling the dental surgeon to view the implantation area via the implant.

As with the first embodiment, mutatis mutandis, the implant 200 can optionally be configured for sealingly closing the passageway 230, for example by means of a sealing fit between the respective prosthesis 190 (or a temporary abutment that is engaged to the implant 200 during the healing process), or independently thereof, thereby closing fluid communication between the outside 907 and the outside 909, preventing ingress of contaminants to the maxilla (or mandible, in respective embodiments) from the intra oral cavity 915, and preventing egress of bone tissue, bone graft material, etc from the maxilla implantation site. Thus, suitable plugs, for example similar to plugs 106, 107, 108 disclosed for the first embodiment can also be used for the embodiment of FIG. 4, mutatis mutandis, with the required changes to enable compatibility therewith. For example, a variation of the plug 107 can be used with implant 200 by removing projection 115. Thus, it is readily apparent that at least plug 106 can be selectively and reversibly operated to close fluid communication via the passageway between the proximal opening and the distal openings, in the embodiment of FIG. 4, independently of the proximal opening being open or closed, or independently of the prosthesis (including the respective prosthesis mounting arrangement) being mounted or unmounted (i.e., fixed or not fixed) with respect to the dental implant. It is also to be noted that plug 106 can be removed proximally from the passageway 230 via the proximal opening.

A third embodiment of the dental implant according to the first aspect of the invention, generally designated with the reference numeral 300, is illustrated in FIGS. 7 to 10, and comprises all the elements and features of the first embodiment and at least some alternative variations thereof, in particular the embodiment illustrated in FIG. 2(b), mutatis mutandis, though with some differences as will become clearer herein. Thus, implant 300 is also in the form of a generally tubular body 305, comprising a proximal portion 310 having a proximal end 320 and opening 362, a distal portion 350 comprising a proximal part 352 and a distal part 354, and having a distal end 360 and three lateral distal openings 358 (though in alternative variations this embodiment can comprise one, two or more than three lateral distal openings) and axial distal opening 359 at the distal end 360, and a lumen or passageway 330 longitudinally extending through the proximal portion 310 and the distal portion 350, respectively corresponding to tubular body 105, proximal portion 110, proximal end 120, opening 162, distal portion 150, proximal part 152, distal part 154, distal end 160, lateral distal openings 158 and axial distal opening 159, and passageway 130 of the first embodiment, mutatis mutandis.

The passageway 330 is internally threaded throughout its length to distal end 360.

In this embodiment, the lateral distal openings 358 are generally cylindrical, having their respective axes substantially orthogonal to, and lying on planes that are aligned with and intersect, the longitudinal axis 301 of the implant 300. In alternative variations of this embodiment (or indeed of the first or second embodiments), the lateral distal openings can have their respective axes at an angle other than 90° to longitudinal axis 301, for example inclined at an acute angle thereto in the distal direction (the respective lateral distal openings being designated 358b in FIG. 9(b)), or for example inclined at an acute angle thereto in the proximal direction (the respective lateral distal openings being designated 358a in FIG. 9(a)). The inclined lateral distal openings 358a and/or 358b can have their respective axes lying on planes that are aligned with and intersect, the longitudinal axis 301 of the implant 300, or alternatively, these axes can lie on respective planes that are parallel to but do not intersect longitudinal axis 301.

The implant 300 further comprises a plug system 316 configured for selectively controlling fluid communication between an outside of proximal portion 310 and an outside of the distal part 354 through passageway 330, via proximal opening 362 and via lateral distal openings 358 and/or axial distal opening 359. In particular, the plug system 316 is configured for selectively and reversibly closing the distal openings independently of the proximal opening being open or closed, or independently of the prosthesis (including its prosthesis mounting arrangement) being mounted or unmounted (i.e., fixed or not fixed) with respect to the dental implant.

Figure 11C:
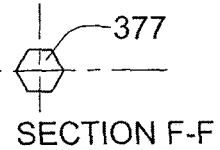
FIG. 11(c) illustrates in cross-sectional view the embodiment of FIG. 11(a) taken along section F-F.
Figure 11A:
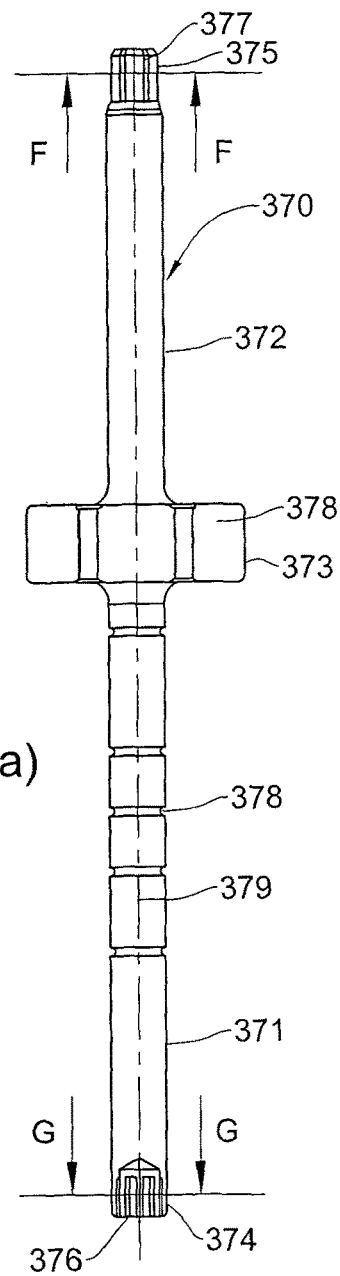
FIG. 11(a) illustrates in side view a first embodiment of a tool, particularly useful for use with the embodiment of FIG. 7.
Figure 11B:
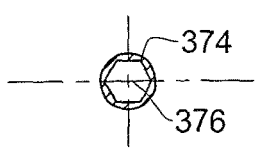
FIG. 11(b) illustrates in cross-sectional view the embodiment of FIG. 11(a) taken along section G-G.

In this embodiment, plug system 316 comprises a distal plug 315 and a proximal plug 314, and, referring in particular to FIGS. 11(a) to 11(c), a tool 370 can be advantageously used to facilitate selectively inserting and removing the distal plug 315 and the proximal plug 314 from the implant body 305.

Tool 370 is formed as a unitary article and comprises a first drive shaft portion 371 co-axially joined to second drive shaft portion 372 via finger actuating portion 373. A first, free end 374 at the end of first drive shaft portion 371, comprises an inwardly extending well 376 having a hexagonal cross-section. A second, free end 375 at the end of second drive shaft portion 372, comprises an outwardly extending projection 377 having a hexagonal cross-section. First drive shaft portion 371 and second first drive shaft portion 372 have external diameters substantially smaller than the inside diameter of passageway 330, while finger actuating portion 373 has an enlarged diameter and has a roughened cylindrical or polygonal outer surface 378 to facilitate being gripped by fingers and allow the tool 370 to be turned about its longitudinal axis 379. The first drive shaft portion 371, comprises a ribbed scale 378 that provides a visual guidance to the user of the penetration of the first drive shaft portion 371 into the passageway 330 when the tool 370 is used with implant 300, or indeed with at least some alternative variations thereof.

Distal plug 315 is primarily configured for selectively sealing axial distal opening 359 while allowing fluid communication from an outside of the implant 300 to the passageway 330 via lateral distal openings 358, but can also be used for selectively sealing both axial distal opening 359 and lateral distal openings 358 with respect to a proximal portion of the passageway 330 including proximal opening 362.

Figure 9:
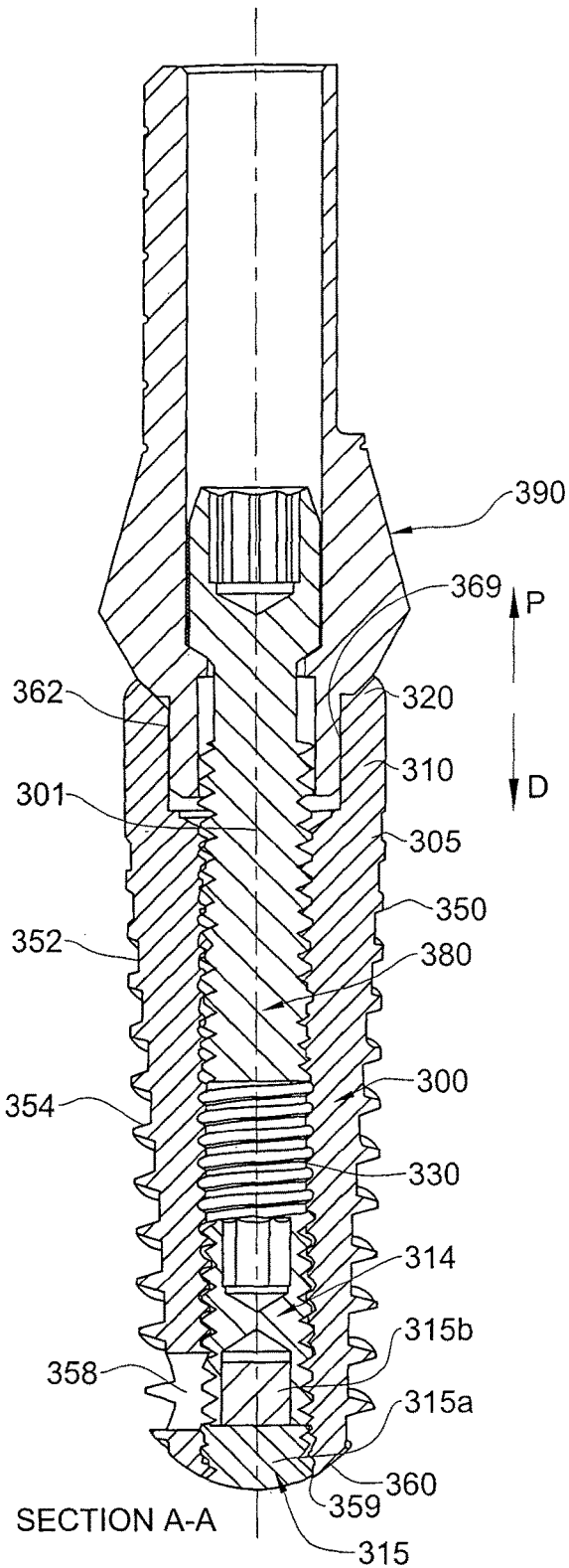
FIG. 9 illustrates, in transverse cross-sectional view, a dental implant according to the embodiment of FIG. 8 along section A-A.
Figure 9A:
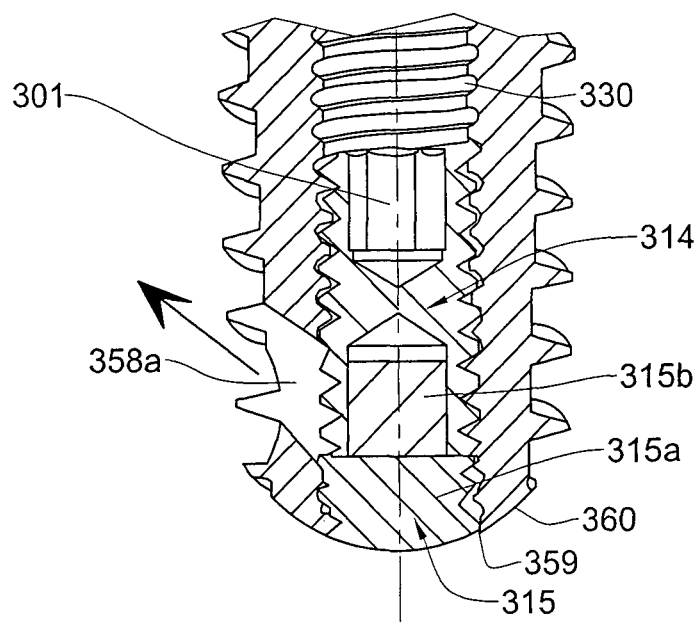
FIG. 9(a) illustrate in partial cross-sectional view, an alternative variation of the embodiment of FIG. 8.
Figure 9B:
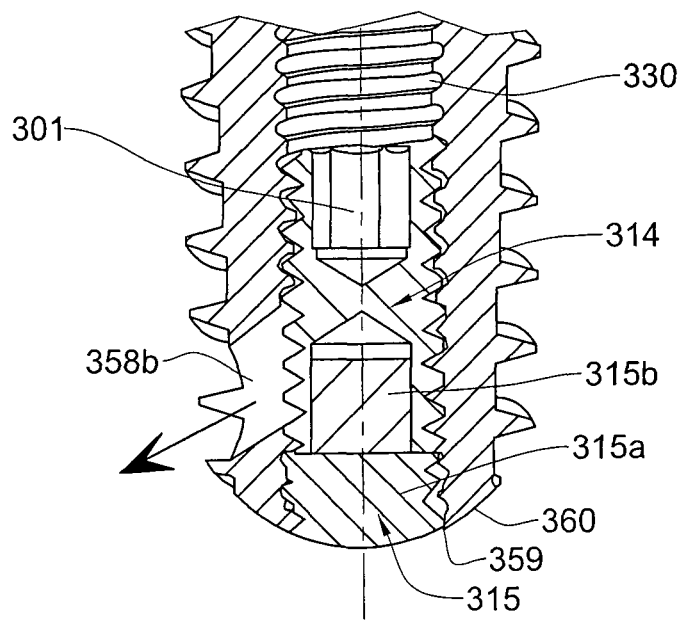
FIG. 9(b) illustrate in partial cross-sectional view, another alternative variation of the embodiment of FIG. 8.

Distal plug 315 comprises a generally cylindrical distal sealing portion 315a that is externally threaded with threads that are complementary to, and effectively form a seal with, the internal threads of internally threaded passageway 330. The distal plug 315 thus can be inserted into and removed from the passageway 330 via the proximal opening 362, and further comprises an integral driving portion 315b, in this embodiment in the form of a proximally extending projection of hexagonal cross-section, to enable the distal plug 315 to be screwed into and out of the passageway 330 using a suitable tool, for example end 374 of plug insertion tool 370, illustrated in FIGS. 11(a) to 11(c). The axial thickness of the distal sealing portion 315a is such as not to interfere with the fluid communication through the lateral distal openings 358, when the distal plug 315 is in its distal sealing position at the distal end of passageway 330, as illustrated in FIG. 9, though in the absence of the proximal plug 314. This, of itself, allows for fluid communication between the passageway 330 and the outside of the distal part 354 via lateral distal openings 358, while the axial distal opening 359 can remain closed on account of the distal plug 315.

It is to be noted that the distal plug 315 itself can also be used for effectively sealing the lateral distal openings 358, by placing at least a proximal part of the distal sealing portion 315a of the distal plug 315 proximally to the lateral distal openings 358, and thus can be used for this function as well.

Proximal plug 314 is primarily configured for selectively sealing lateral distal openings 358, when the proximal plug 314 is in its distal sealing position, and comprises a sealing body 314a that is externally threaded with threads that are complementary to, and effectively form a seal with, the internal threads of internally threaded passageway 330. The proximal plug 314 thus can be inserted into and removed from the passageway 330 via the proximal opening 362, and further comprises an integral driving portion 314b, in this embodiment in the form of a proximally facing well of hexagonal cross-section, to enable the proximal plug 314 to be screwed into and out of the passageway 330 using a suitable tool, for example end 375 of plug insertion tool 370, illustrated in FIGS. 11(a) to 11(c). The distal end of proximal plug 314 also comprises a well 314c that is configured to accommodate driving portion 315b of the distal plug 315 when this is in its distal sealing position at the distal end of passageway 330, and the proximal plug 314 is in its distal sealing position near the distal end of passageway 330, and in abutment with the distal plug 315. The well 314c has an internal diameter greater than the maximum cross-sectional width of the driving portion 315b, and thus can be helically moved into its sealing position without fouling with the driving portion 315b. The axial thickness of the sealing body 314a is such as to block fluid communication through the lateral distal openings 358, at least when the distal plug 315 is in its distal sealing position at the distal end of passageway 330, and the proximal plug 314 is in abutment therewith, as illustrated in FIG. 9. It is to be noted that the proximal plug 314 itself also automatically effectively seals the axial distal opening 359, and thus can be used for this function as well even in the absence of the distal plug 315.

In this embodiment, at the distal end of passageway 330, a mechanical stop (not shown) is provided, in the form of an annular bead, which prevents the distal plug 315, or indeed the proximal plug 314, from exiting the passageway 330, in a distal direction. This is a safety feature that prevents the user from accidentally over-screwing the distal plug 315, and indeed from accidentally over-screwing the proximal plug 314, in a distal direction when the implant is implanted, and avoids otherwise possibly ejecting the respective distal plug 315 or the respective proximal plug 315 into the body distally of the implant. In alternative variations of this embodiment, the mechanical stop can be omitted.

The passageway 330 is further configured to receive and lock therein a locking nut 380 that locks the respective abutment 390 to the proximal portion 320. A suitable prosthesis can be suitable affixed to the abutment 390.

The dental implant 300 comprises a hexagonally shaped well 369 at the proximal end 362, configured for mounting therein the prosthesis via abutment 390.

Figure 12:
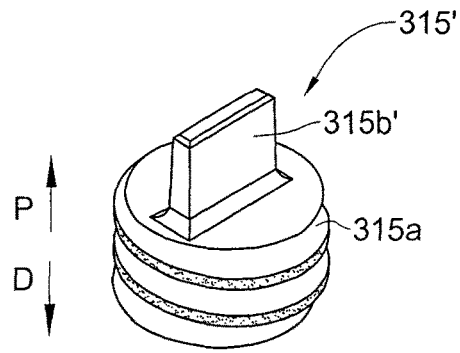
FIG. 12 illustrates in isometric view an alternative embodiment of the distal plug of the embodiment of FIG. 7.
Figure 10:
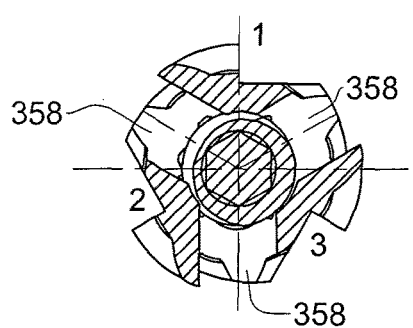
FIG. 10 illustrates, in cross-sectional view, a dental implant according to the embodiment of FIG. 8 along section B-B.
Figure 13:
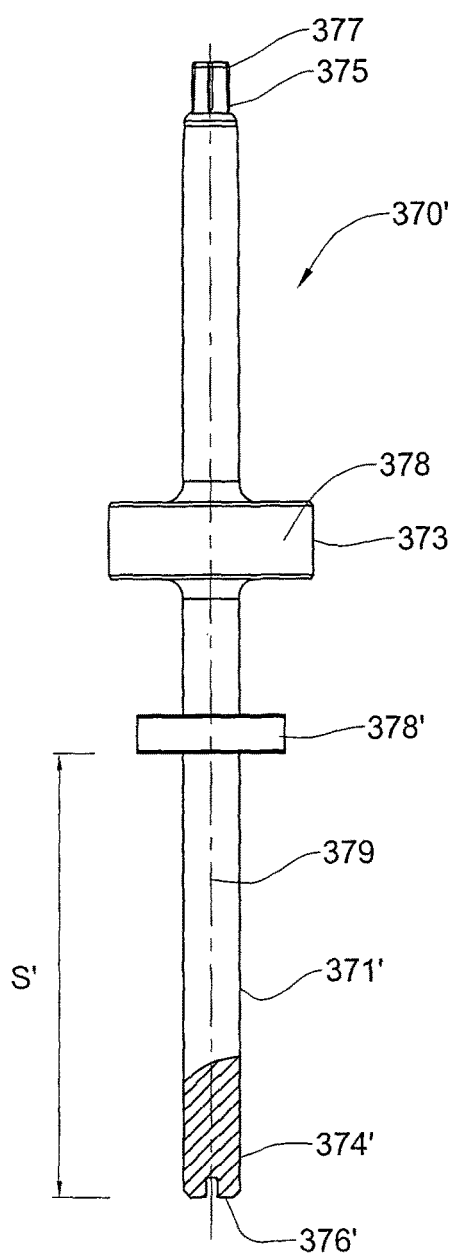
FIG. 13 illustrates in side view another embodiment of a tool, particularly useful for use with a variation of the embodiment of FIG. 7 incorporating the embodiment of FIG. 12.

Referring to FIG. 12, in an alternative variation of the embodiment of FIGS. 7 to 10, the distal plug, herein designated 315', is modified wherein the respective driving portion 315b' is, in this embodiment, in the form of a proximally extending flat tab, rather than in the form of a projection of hexagonal cross-section. As will become clearer below, this has the effect of minimizing obstruction of the lateral distal openings 358 by the driving portion 315b' when the distal plug 315' is in its distal sealing position at the distal end of passageway 330, relative to the distal plug 315 of the embodiment of FIG. 7. Manipulation and insertion of this modified distal plug 315' can be facilitated by means of a modified tool 370', illustrated in FIG. 13, which is substantially identical to tool 370 as disclosed above, mutatis mutandis, with some differences, as follows. In tool 370', the respective free end 374', at the end of respective first drive shaft portion 371', comprises a diametrical slot 376', rather than the inwardly extending well 376 with hexagonal cross-section of tool 370, to engage the tab-shaped respective driving portion 315b'. Furthermore, the ribbed scale 378 of the tool 370 is omitted in tool 370' (though optionally it can be retained), and a mechanical stop 378' is provided on the respective first drive shaft portion 371', at a distance S' from the end 374' that is correlated to the spacing between the distal plug 315' and the proximal end of the implant 300 when the distal plug 315' is in its distal sealing position at the distal end of passageway 330. The mechanical stop 378 thus acts as a safety feature, and prevents the distal plug 315' and the proximal end of the implant 300 when the distal plug 315' from being screwed further into the passageway 330 past its distal sealing position at the distal end of passageway 330 or all the way ejected out of the distal end 360, by abutting against the proximal end of the implant 300 and preventing further distal movement of the tool 370' into the implant 300. Optionally, the tool 370 of FIGS. 11(a) to 11(c) can also comprise a mechanical stop on its respective first shaft portion 371, similar to mechanical stop 378' that is provided on the respective first drive shaft portion 371' of tool 370', mutatis mutandis.

The dental implant 300 can be formed as a unitary piece or from several components suitably joined together, and made from one or more suitable and biocompatible materials, for example metallic medically compatible materials such as for example titanium and/or stainless steel, and/or for example non-metallic medically compatible materials such as for example material MP-1 developed by NASA, and/or other suitable plastics and/or polymers, for example.

The distal plug 315 (and/or 315') and the proximal plug 314 can likewise each be made from one or more suitable and biocompatible materials, for example metallic medically compatible materials such as for example titanium and/or stainless steel, and/or for example non-metallic medically compatible materials such as for example material MP-1 developed by NASA, and/or the polymer marketed under "PEEK" by Victrex, Polyamide, and/or other suitable plastics and/or polymers, for example. For example, such polyamide, plastics and/or polymers may have one or more of the following characteristics:

Vicat softening temperature B/50—DIN EN ISO 306—of between about −40° C. to about +180° C.;
Tensile modulus—DIN EN ISO 527—about 1700 N/mm$^2$;
Flexural modulus—DIN EN ISO 178—about 1240 N/mm$^2$;
Tensile strength—DIN EN ISO 527—about 45 N/mm$^2$;
Hardness—DIN 53505—75—SHORE D;
Density about 0.9 g/cm$^3$.

Alternatively, at least the distal plug 315 (and/or 315') can be made from, or comprises a window made from, a suitable transparent material, that is also biocompatible, such as for example glass or a suitable transparent polymer, and/or any suitable material—for example a sapphire stone—thereby providing a direct line-of-sight (LOS) from the proximal opening 362 and through the distal end 360 along axis 301 when the when the distal plug 315 (or 315') is in its distal sealing position at the distal end of passageway 330. Thus, the distal portion 350 is configured for being implanted in the maxilla 900 of a patient, and comprises proximal part 352 and distal part 354. The distal portion 350 has a dimension L along the longitudinal axis 301 of the implant 300 of sufficient magnitude, such that in the implanted position of the implant 300, the distal part 354 of the distal portion 350, including the distal end 360, projects through the alveolar ridge 901 and away from the sinus floor 907 in the direction towards the sinus cavity 910, while the proximal part 352 is anchored in the bone of the alveolar ridge 901 of the maxilla 900. In the aforesaid "implanted position", the implant 300 is at its maximal desired distal position with respect to the maxilla, illustrated in FIG. 8, so that the proximal portion 310 is at the desired permanent position with respect to the maxilla 900 to receive the abutment 390 and prosthesis.

Thus, the longitudinal length $L_p$ of the proximal part 310 is correlated and generally corresponds to the depth of the alveolar ridge 901, up to the sinus cavity 905, and for example, this longitudinal length $L_p$ can be between about 2 mm and about 8 mm. The distal part 354 has a longitudinal length $L_d$ that projects into the sinus cavity 906, and represents the minimum depth of the sinus augmentation that is formed by means of the dental implant 300.

Furthermore, in the dental implant 300, there is a direct line-of-sight (LOS) between the proximal opening 362 and distal opening 359 along axis 301 when the respective distal plug 315 (or 315') is removed.

The direct line of sight between the proximal end of the implant and the environment distal of the distal end provided by the implant according to the first aspect of the invention, for example the disclosed embodiments thereof, can also be useful in other dental procedures, such as for example when installing such an implant in the mandibular jaw in which the risks of damaging the inferior alveolar nerve in the mandibular canal are minimized by virtue of enabling the dental surgeon to view the implantation area via the implant. In the case of the implant 300 according to the third embodiment, this implant (as well as alternative variations thereof) can provide the surgeon with the choice of selectively viewing the implantation area when desired by removing the respective distal plug 315 (or 315'), even in the midst of an implantation procedure, and to replace the respective distal plug 315 (or 315') whenever the surgeon considers that further advance of the implant 300 is to be accomplished with a closed distal end or when the implant 300 is fully installed.

It is to be noted that any one of the proximal plug 314, or distal plug 315, or distal plug 315' can be used on its own for effectively sealing off a passageway distal portion (that includes the lateral distal openings 358 and the axial distal opening 359) of passageway 330 from a passageway proximal portion, allowing the locking nut 380 that locks the respective abutment 390 (and thus the dental prosthesis) to the proximal portion 320 of the implant 300. Furthermore, it is also to be noted that by sealing off said passageway 330 at a position proximal to the lateral distal openings 358 and/or axial openings 359, it is possible to maintain fluid communication between an outside of the implant, in particular outside of the distal portion 350, and said passageway distal portion via the respective distal opening while concurrently sealing off the passageway distal portion from the passageway proximal portion. A feature of this is that, on the one hand, the passageway proximal portion is sealed off from the inner part of the maxilla (or mandible in respective embodiments), while on the other hand, boney tissues, including bone graft material (in respective embodiments) can promote anchoring of the implant into the respective jaw.

It is also to be noted that any one of the proximal plug 314, or distal plug 315, or distal plug 315' can be used on its own to provide a sealing arrangement that is configured for selectively and reversibly closing at least one distal opening concurrently with the proximal opening of the implant 300 being open.

It is also to be noted that each one of the proximal plug 314, or distal plug 315, or distal plug 315' can be removed proximally from the passageway 330 via the proximal opening.

A fourth embodiment of the dental implant according to this aspect of the invention, generally designated with the reference numeral 400, is illustrated in FIGS. 17 to 21, and comprises the elements and features of at least the third embodiment and at least some alternative variations thereof, in particular the embodiment illustrated in FIGS. 7 to 10, mutatis mutandis, though with some differences as will become clearer herein. Thus, implant 400 is also in the form of a generally tubular body 405, comprising a proximal portion 410 having a proximal end 420 and opening 462, a distal portion 450 comprising a proximal part 452 and a distal part 454, and having a distal end 460 and three lateral distal openings 458 (though in alternative variations this embodiment can comprise one, two or more than three lateral distal openings) and axial distal opening 459 at the distal end 460, and a lumen or passageway 430 longitudinally extending through the proximal portion 410 and the distal portion 450, respectively corresponding to tubular body 305, proximal portion 310, proximal end 320, opening 362, distal portion 350, proximal part 352, distal part 354, distal end 360, lateral distal openings 358 and axial distal opening 359, and passageway 330 of the third embodiment, mutatis mutandis.

In the fourth embodiment, a proximal portion 430B of the passageway 430 is internally threaded for part of its length extending from opening 462 up to an intermediate interface 430A, and a distal portion 430C of the passageway 430 is unthreaded from interface 430A to distal end 460. In this embodiment, distal lumen portion 430C is substantially cylindrical, i.e., of uniform diameter along its length.

In this embodiment, the lateral distal openings 458 are generally cylindrical, having their respective axes substantially orthogonal to, and lying on planes that are aligned with, and intersect, the longitudinal axis 401 of the implant 400. In alternative variations of this embodiment, the lateral distal openings can have their respective axes at an angle other than 90° to longitudinal axis 401, for example inclined at an acute angle thereto in the distal direction, or for example inclined at an acute angle thereto in the proximal direction, for example as disclosed with respect to the third embodiment and FIGS. 9(*a*), 9(*b*), mutatis mutandis. Such inclined lateral distal openings can have their respective axes lying on planes that are aligned with and intersect, the longitudinal axis 401 of the implant 400, or alternatively, these axes can lie on respective planes that are parallel to but do not intersect longitudinal axis 401.

The implant 400 further comprises a plug system configured for selectively controlling fluid communication between an outside of proximal portion 410 and an outside of the distal part 454 through passageway 430, via proximal opening 462 and via lateral distal openings 458 and axial distal opening 459. In particular, the plug system is configured for selectively and reversibly closing the distal openings independently of the proximal opening being open or closed, or independently of the prosthesis being mounted or unmounted (i.e., fixed or not fixed) with respect to the dental implant.

Figure 23:
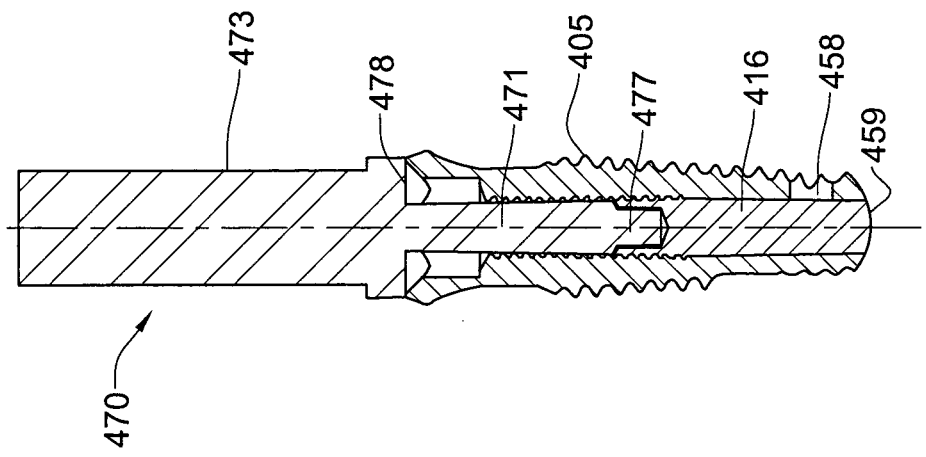
FIG. 23 illustrates in cross-sectional side view the tool embodiment of FIG. 22 engaged with the embodiment of FIG. 17.
Figure 22:
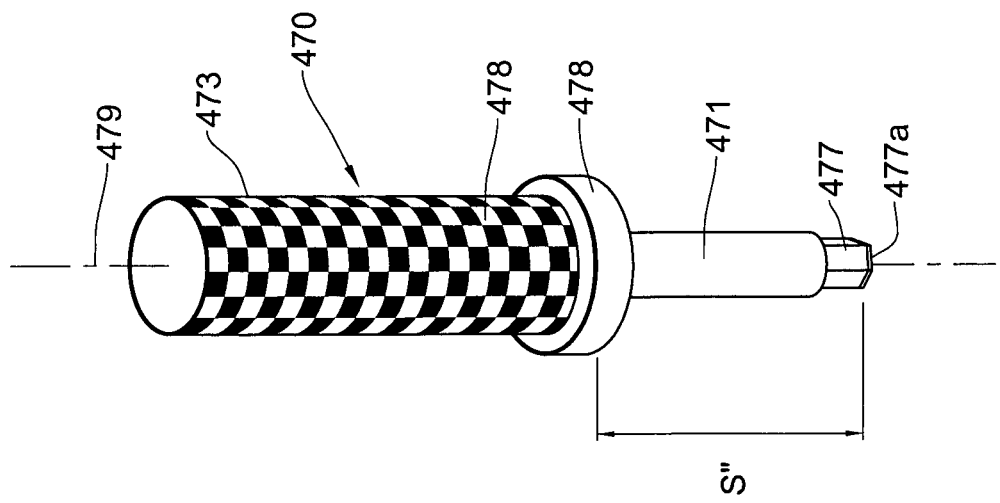
FIG. 22 illustrates in side view an embodiment of a tool, particularly useful for use with the embodiment of FIG. 17 or 24.
Figure 24:
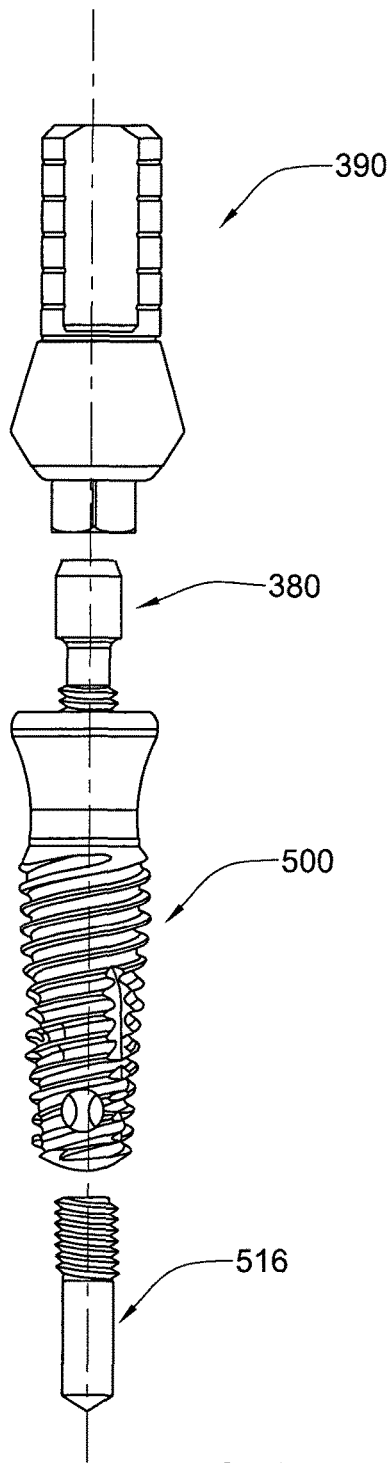
FIG. 24 illustrates in exploded side view, a dental implant according to a fifth embodiment of the invention.
Figure 25:
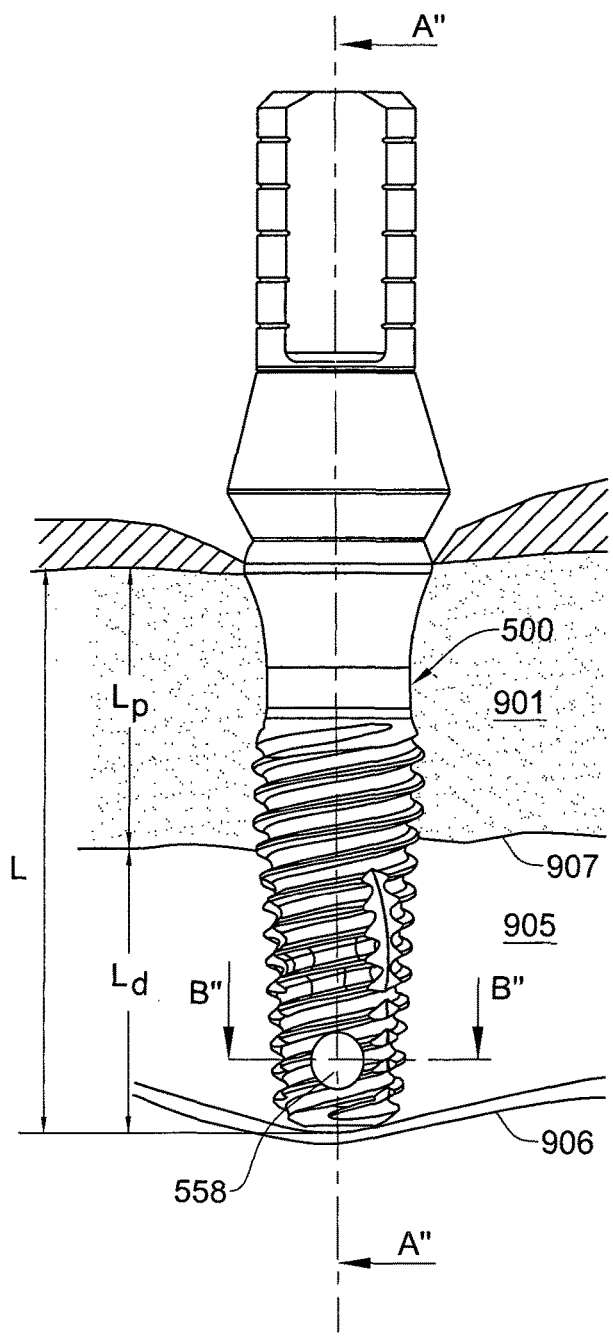
FIG. 25 illustrates, in side view, a dental implant according to the embodiment of FIG. 24.

In this embodiment, plug system comprises a single plug 416 (different from the prosthesis mounting arrangement), and, referring in particular to FIGS. 22 and 23, a tool 470 can be advantageously used to facilitate selectively inserting and removing the plug 416 from the implant body 405.

Tool 470 can be formed as a unitary article, for example, and comprises a drive shaft portion 471 co-axially joined to handle portion 473. A free end 474 at the end of drive shaft portion 471 comprises an outwardly extending projection 477 having a hexagonal cross-section. The drive shaft portion 471 has an external diameter substantially smaller than the inside diameter of passageway 430, in particular threaded portion 430B, while handle portion 473 has an enlarged diameter and has an outer surface 478 that is finely knurled, or otherwise roughened cylindrical (or alternatively can comprise a polygonal outer surface) to facilitate being gripped by fingers of a user and to allow the tool 470 to be turned about its longitudinal axis 479. A mechanical stop 478 is provided on the drive shaft portion 471, at a distance S" from the distal end 477a of the tool 470.

The plug 416 is configured for selectively and concurrently sealing axial distal opening 459 and lateral distal openings 458, with respect to a proximal portion of the passageway 430 (in particular, of the threaded portion 430B) including proximal opening 462.

Plug 416 comprises a generally cylindrical distal portion 415 that is externally unthreaded, having an external surface that is complementary to, and can form a seal with, the unthreaded portion 430C of passageway 430. The plug 416 also comprises a proximal sealing body 414 that is externally threaded with threads that are complementary to, and effectively form a seal with, the internal threads of internally threaded portion 430B of passageway 430. The plug 416 further comprises a distal plug end 414a.

The plug 416 can be inserted into and removed from the passageway 430 via the proximal opening 462, and further comprises an integral driving portion 414b, in this embodiment in the form of a proximally facing well of hexagonal cross-section, to enable the plug 416 to be screwed into and out of the passageway 430 using a suitable tool, for example end 477 of tool 470, illustrated in FIGS. 22 and 23. N alternative variations of this embodiment, the plug can be otherwise configured for being easily and selectively inserted and removed from the implant 400.

In its distal sealing position in the passageway 430, the distal portion 415 seals against the unthreaded portion 430C of passageway 430, and/or the proximal sealing body 414 seals against the distal part of threaded portion 430B of passageway 430, thereby blocking fluid communication through the lateral distal openings 458 and axial distal opening 459, wherein the plug distal end 414a is axially aligned with distal end 459.

In an alternative variations of this embodiment, unthreaded portion 430C is frusto conical, for example tapering uniformly to a smaller diameter at the distal end 459 than at just distal to the interface 430A, and the distal portion 415 of plug 416 is complementarily frusto conical, having a cross-section tapering uniformly from just distal of proximal sealing body 414 to a smaller diameter at the plug distal end 414a, or alternatively tapering in the opposite direction. Such configurations for the unthreaded portion 430C and the distal portion 415 enhance sealing therebetween as the plug 416 is advanced distally to its sealing position and the two frusto conical surfaces abut with, or otherwise contact, one another.

In yet another alternative variation of this embodiment, unthreaded portion 430C is frusto conical, for example tapering uniformly to a smaller diameter at the distal end 459 than at just distal to the interface 430A, while the distal portion 415 of plug 416 is cylindrical, having a uniform cross-section. In yet another alternative variation of this embodiment, unthreaded portion 430C is substantially cylindrical, with a uniform cross-section, while the distal portion 415 of plug 416 is substantially frusto conical, having a cross-section tapering uniformly from just distal of proximal sealing body 414 to a smaller diameter at the plug distal end 414a. Such configurations for the unthreaded portion 430C and the distal portion 415 enhance sealing therebetween as the plug 416 is advanced distally to its sealing position and the two facing surfaces abut with, or otherwise contact, one another.

The distance S" is correlated to the spacing between the well 414b of plug 416 and the proximal end of the implant 400 when the plug 416 is in its distal sealing position. The mechanical stop 478 thus acts as a safety feature, and prevents the plug 416 from being screwed further into the passageway 430 past its distal sealing position with respect to passageway 430 or all the way ejected out of the distal end 460, by abutting against the proximal end of the implant 400 and preventing further distal movement of the tool 470 into the implant 400.

Furthermore, in this embodiment, the threaded portion 430B is of larger internal diameter than the unthreaded portion 430C. Thus, the interface 430A acts as a mechanical stop which automatically prevents the plug 416 from exiting the passageway 430, in a distal direction, even when the plug is inserting when not using tool 470. This is a safety feature that prevents the user from accidentally over-screwing the plug 416 in a distal direction when the implant is implanted, and avoids otherwise possibly ejecting the respective plug 416 into the body distally of the implant. In alternative variations of this embodiment, the mechanical stop feature can be omitted—for example the threaded portion 430B can of the same or smaller internal diameter than the unthreaded portion 430C.

In a similar manner to the third embodiment, mutatis mutandis, the passageway 430, in particular a proximal portion thereof, in particular part of the threaded portion 430B, is further configured to receive and lock therein a locking nut 380 that locks the respective abutment 390 to the proximal portion 420, and a suitable prosthesis can be suitable affixed to the abutment 390, The dental implant 400 comprises a hexagonally shaped well 469 at the proximal end 462, configured for mounting therein the prosthesis via abutment 390.

In a similar manner to the third embodiment, mutatis mutandis, the dental implant 400 can be formed as a unitary piece or from several components suitably joined together, and made from one or more suitable and biocompatible materials, for example metallic medically compatible materials such as for example titanium and/or stainless steel, and/or for example non-metallic medically compatible materials such as for example material MP-1 developed by NASA and/or other suitable plastics and/or polymers, for example. The plug 416 can likewise be made from one or more suitable and biocompatible materials, for example metallic medically compatible materials such as for example titanium and/or stainless steel, and/or for example non-metallic medically compatible materials such as for example material MP-1 developed by NASA, and/or the polymer marketed under "PEEK" by Victrex, Polyamide, and/or other suitable plastics and/or other suitable polymers, for example. For example, such polyamide, plastics and/or polymers may have one or more of the following characteristics:

Vicat softening temperature B/50—DIN EN ISO 306—of between about −40° C. to about +180° C.;

Tensile modulus—DIN EN ISO 527—about 1700 N/mm$^2$;

Flexural modulus—DIN EN ISO 178—about 1240 N/mm$^2$;

Tensile strength—DIN EN ISO 527—about 45 N/mm$^2$;

Hardness—DIN 53505—75—SHORE D;

Density about 0.9 g/cm$^3$.

Alternatively, at least the plug 416 be made from, or comprises a window made from, a suitable transparent material, that is also biocompatible, such as for example glass and/or a suitable transparent polymer, and/or any suitable material—for example a sapphire stone—thereby providing a direct line-of-sight (LOS) from the proximal opening 462 and through the distal end 460 along axis 401 when the when the plug 416 is in its distal sealing position with respect to passageway 430.

Thus, the distal portion 450 is configured for being implanted in the maxilla 900 of a patient, and comprises proximal part 452 and distal part 454. The distal portion 450 has a dimension L along the longitudinal axis 401 of the implant 400 of sufficient magnitude, such that in the implanted position of the implant 400, the distal part 454 of the distal portion 450, including the distal end 460, projects through the alveolar ridge 901 and away from the sinus floor 907 in the direction towards the sinus cavity 910, while the proximal part 452 is anchored in the bone of the alveolar ridge 901 of the maxilla 900. In the aforesaid "implanted position", the implant 400 is at its maximal desired distal position with respect to the maxilla, illustrated in FIG. 18, so that the proximal portion 410 is at the desired permanent position with respect to the maxilla 900 to receive the abutment 390 and prosthesis.

Thus, the longitudinal length $L_p$ of the proximal part 410 is correlated and generally corresponds to the depth of the alveolar ridge 901, up to the sinus cavity 905, and for example, this longitudinal length $L_p$ can be between about 2 mm and about 8 mm. The distal part 454 has a longitudinal length $L_d$ that projects into the sinus cavity 906, and represents the minimum depth of the sinus augmentation that is formed by means of the dental implant 400.

Furthermore, in the dental implant 400, there is a direct line-of-sight (LOS) between the proximal opening 462 and distal opening 459 along axis 401 when the respective plug 416 is removed.

The direct line of sight between the proximal end of the implant and the environment distal of the distal end provided by the implant according to this aspect of the invention, for example the disclosed embodiments thereof, can also be useful in other dental procedures, such as for example when installing such an implant in the mandibular jaw in which the risks of damaging the inferior alveolar nerve in the mandibular canal are minimized by virtue of enabling the dental surgeon to view the implantation area via the implant. In the case of the implant 400 according to the fourth embodiment, the implant (as well as alternative variations thereof) can provide the surgeon with the choice of selectively viewing the implantation area when desired by removing the plug even in the midst of an implantation procedure, and to replace the plug whenever the surgeon considers that further advance of the implant 400 is to be accomplished with a closed distal end or when the implant 400 is fully installed.

It is to be that it is possible to seal off said passageway 430 at a position proximal to the lateral distal openings 458 and/or axial openings 459. For example, the plug 416 can be screwed in partially into the passageway 430, so that the plug end 414a is proximal of the distal openings 458 (this requires the locking nut 380 to be correspondingly shorter). Alternatively, the distal portion 415 can be shorter than in the embodiment illustrated in FIG. 19, such that when the proximal sealing body 414 is at is most distal position at the interface 430A, the plug end 414a is proximal of the distal openings 458. Alternatively, the interface 430A is provided at a more proximal position in the passageway 430 so that when proximal sealing body 414 is at is most distal position at the interface 430A, the plug end 414a is proximal of the distal openings 458.

In any case, by sealing off said passageway 430 at a position proximal to the lateral distal openings 458 and/or axial openings 459, it is possible to maintain fluid communication between an outside of the implant, in particular outside of the distal portion 450, and said passageway distal portion via the respective distal opening while concurrently sealing off the passageway distal portion from the passageway proximal portion. A feature of this is that, on the one hand, the passageway proximal portion is sealed off from the inner part of the maxilla (or mandible in respective embodiments), while on the other hand, boney tissues, including bone graft material (in respective embodiments) can promote anchoring of the implant into the respective jaw.

It is also to be noted that plug 416 provides a sealing arrangement that is configured for selectively and reversibly closing at least one distal opening concurrently with the proximal opening of the implant 400 being open.

It is also to be noted that the plug 416 can be removed proximally from the passageway 430 via the proximal opening.

A fifth embodiment of the dental implant according to this aspect of the invention, generally designated with the reference numeral 500, is illustrated in FIGS. 24 to 28, and comprises the elements and features of at least the fourth embodiment and at least some alternative variations thereof, in particular the embodiment illustrated in FIGS. 17 to 21, as well as some of the features of the third embodiment and at least some alternative variations thereof, in particular the embodiment illustrated in FIGS. 7 to 10, mutatis mutandis, though with some differences as will become clearer herein. Thus, implant 500 is also in the form of a generally tubular body 505, comprising a proximal portion 510 having a proximal end 520 and opening 562, a distal portion 550 comprising a proximal part 552 and a distal part 554, and having a distal end 560 and three lateral distal openings 558 (though in alternative variations this embodiment can comprise one, two or more than three lateral distal openings), distal end 560, and a lumen or passageway 530 longitudinally extending through the proximal portion 510 and the distal portion 550, respectively corresponding to tubular body 405, proximal portion 410, proximal end 420, opening 462, distal portion 450, proximal part 452, distal part 454, distal end 460, lateral distal openings 458, passageway 430 of the fourth embodiment, mutatis mutandis. A proximal portion 530B of the passageway 530 is internally threaded extending from opening 562 up to an intermediate interface 530A, and a distal portion 530C of the passageway 530 is unthreaded from interface 530A to distal end 560. In this embodiment, distal lumen portion 530C is substantially cylindrical, i.e., of uniform diameter along its length.

However, in contrast to at least the third or fourth embodiment, the implant 500 does not have an axial distal opening at the distal end 560 corresponding to axial distal opening 359 or 459, and thus the distal end 560 is permanently closed via distal end wall 560A. In this manner, the fifth embodiment is structurally and functionally similar in some ways to the third embodiment, mutatis mutandis, when the respective distal plug 315 or 315' is in its distal sealing position with respect to the implant 300 at the distal end of passageway 330.

Furthermore, in this embodiment, the threaded portion 530B is of larger internal diameter than the unthreaded portion 530C. In alternative variations of this embodiment, the mechanical stop feature can be omitted—for example the threaded portion 530B can of the same or smaller internal diameter than the unthreaded portion 530C.

The lateral distal openings 548 are as disclosed for the third or fourth embodiments and alternative variations thereof, mutatis mutandis.

The implant 500 further comprises a plug system configured for selectively controlling fluid communication between an outside of proximal portion 510 and an outside of the distal part 554 through passageway 530, via proximal opening 562 and via lateral distal openings 558, and in particular, the plug system is configured for selectively and reversibly closing the distal openings independently of the proximal opening being open or closed, or independently of the prosthesis (including any prosthesis mounting arrangement) being mounted or unmounted (i.e., fixed or not fixed) with respect to the dental implant.

In the fifth embodiment, plug system comprises a single plug 516 (different from the prosthesis mounting arrangement), which is similar to plug 416 of the fourth embodiment, mutatis mutandis, with the main difference that plug 516 is shorter and only closes the respective lateral distal openings 558 when installed in its distal sealing position. Furthermore, tool 470 can also be advantageously used to facilitate selectively inserting and removing the plug 516 from the implant body 505.

Thus, the plug 516 is configured for selectively sealing lateral distal openings 558, with respect to a proximal portion of the passageway 530 (in particular of the threaded portion 530B) including proximal opening 562.

Plug 516 comprises a generally cylindrical distal portion 515 that is externally unthreaded, having an external surface that is complementary to, and can form a seal with, the unthreaded portion 530C of passageway 530. The plug 516 also comprises a proximal sealing body 514 that is externally threaded with threads that are complementary to, and effectively form a seal with, the internal threads of internally threaded portion 530B of passageway 530. The plug 416 further comprises a distal plug end 514a that abuts against or is proximal to the inside of distal end wall 560A.

Figure 29:
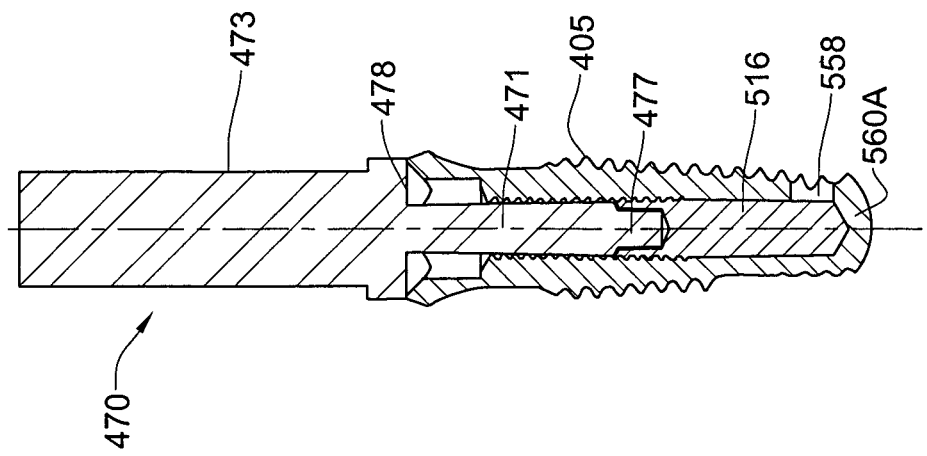
FIG. 29 illustrates in cross-sectional side view the tool embodiment of FIG. 22 engaged with the embodiment of FIG. 24.

The plug 516 can be inserted into and removed from the passageway 530 via the proximal opening 562, and further comprises an integral driving portion 514b, in this embodiment in the form of a proximally facing well of hexagonal cross-section, to enable the plug 516 to be screwed into and out of the passageway 530 using a suitable tool, for example end 477 of tool 470, illustrated in FIGS. 22 and 29.

In its distal sealing position in the passageway 530, the distal portion 515 seals against the unthreaded portion 530C of passageway 530, and/or the proximal sealing body 514 seals against the distal part of threaded portion 530B of passageway 530, thereby blocking fluid communication through the lateral distal openings 558.

In an alternative variation of this embodiment, unthreaded portion 530C is frusto conical, for example tapering uniformly to a smaller diameter at the distal end 559 than at just distal to the interface 530A, and the distal portion 515 of plug 516 is complementarily frusto conical, having a cross-section tapering uniformly from just distal of proximal sealing body 514 to a smaller diameter at the plug distal end 514a, or alternatively tapering in the opposite direction. Such configurations for the unthreaded portion 530C and the distal portion 515 enhances sealing therebetween as the plug 516 is advanced distally to its sealing position and the two frusto conical surfaces abut with, or otherwise contact, one another.

In yet another alternative variation of this embodiment, unthreaded portion 530C is frusto conical, tapering uniformly to a smaller diameter at the distal end 559 than at just distal to the interface 530A, while the distal portion 515 of plug 516 is cylindrical, having a uniform cross-section. In yet another alternative variation of this embodiment, unthreaded portion 530C is substantially cylindrical, with a uniform cross-section, while the distal portion 515 of plug 516 is substantially frusto conical, having a cross-section tapering uniformly from just distal of proximal sealing body 514 to a smaller diameter at the plug distal end 514a. Such configurations for the unthreaded portion 530C and the distal portion 515 enhances sealing therebetween as the plug 516 is advanced distally to its sealing position and the two facing surfaces abut with, or otherwise contact, one another.

The distance S" is also correlated to the spacing between the well 514b of plug 516 and the proximal end of the implant 500 when the plug 516 is in its distal sealing position.

In a similar manner to the third or fourth embodiments, mutatis mutandis, the passageway 530, in particular the threaded portion 530B, is further configured to receive and lock therein a locking nut 380 that locks the respective abutment 390 to the proximal portion 420, and a suitable prosthesis can be suitable affixed to the abutment 390.

The dental implant 500 comprises a hexagonally shaped well 569 at the proximal end 562, configured for mounting therein the prosthesis via abutment 390.

In a similar manner to the third or fourth embodiments, mutatis mutandis, the dental implant 500 can be formed as a unitary piece or from several components suitably joined together, and made from one or more suitable and biocompatible materials, for example metallic medically compatible materials such as for example titanium and/or stainless steel, and/or for example non-metallic medically compatible materials such as for example material MP-1 developed by NASA and/or other suitable plastics and/or other suitable polymers, for example. The plug 516 can likewise be made from one or more suitable and biocompatible materials, for example metallic medically compatible materials such as for example titanium and/or stainless steel, and/or for example non-metallic medically compatible materials such as for example material MP-1 developed by NASA, and/or the polymer marketed under "PEEK" by Victrex, and/or Polyamide, and/or other suitable plastics and/or other suitable polymers, for example. For example, such polyamide, plastics and/or polymers may have one or more of the following characteristics:

Vicat softening temperature B/50—DIN EN ISO 306—of between about −40° C. to about +180° C.;
Tensile modulus—DIN EN ISO 527—about 1700 N/mm$^2$;
Flexural modulus—DIN EN ISO 178—about 1240 N/mm$^2$;
Tensile strength—DIN EN ISO 527—about 45 N/mm$^2$;
Hardness—DIN 53505—75—SHORE D;
Density about 0.9 g/cm$^3$.

Thus, the distal portion 550 is configured for being implanted in the maxilla 900 of a patient, and comprises proximal part 552 and distal part 554. The distal portion 550 has a dimension L along the longitudinal axis 501 of the implant 500 of sufficient magnitude, such that in the implanted position of the implant 500, the distal part 554 of the distal portion 550, including the distal end 560, projects through the alveolar ridge 901 and away from the sinus floor 907 in the direction towards the sinus cavity 910, while the proximal part 552 is anchored in the bone of the alveolar ridge 901 of the maxilla 900. In the aforesaid "implanted position", the implant 500 is at its maximal desired distal position with respect to the maxilla, illustrated in FIG. 25, so that the proximal portion 510 is at the desired permanent position with respect to the maxilla 900 to receive the abutment 390 and prosthesis.

Thus, the longitudinal length $L_p$ of the proximal part 510 is correlated and generally corresponds to the depth of the alveolar ridge 901, up to the sinus cavity 905, and for example, this longitudinal length $L_p$ can be between about 2 mm and about 8 mm. The distal part 554 has a longitudinal length $L_d$ that projects into the sinus cavity 906, and represents the minimum depth of the sinus augmentation that is formed by means of the dental implant 400.

It is to be that it is possible to seal off said passageway 530 at a position proximal to the lateral distal openings 558. For example, the plug 516 can be screwed in partially into the passageway 530, so that the plug end 414*a* is proximal of the lateral distal openings 558 (this requires the locking nut 380 to be correspondingly shorter). Alternatively, the distal portion 515 can be shorter than in the embodiment illustrated in FIG. 26, such that when the proximal sealing body 514 is at is most distal position at the interface 530A, the plug end 514*a* is proximal of the lateral distal openings 558. Alternatively, the interface 530A is provided at a more proximal position in the passageway 530 so that when proximal sealing body 514 is at is most distal position at the interface 530A, the plug end 514*a* is proximal of the distal openings 558.

In any case, by sealing off said passageway 530 at a position proximal to the lateral distal openings 558, it is possible to maintain fluid communication between an outside of the implant, in particular outside of the distal portion 550, and said passageway distal portion via the respective distal opening while concurrently sealing off the passageway distal portion from the passageway proximal portion. A feature of this is that, on the one hand, the passageway proximal portion is sealed off from the inner part of the maxilla (or mandible in respective embodiments), while on the other hand, boney tissues, including bone graft material (in respective embodiments) can promote anchoring of the implant into the respective jaw.

It is also to be noted that plug 516 provides a sealing arrangement that is configured for selectively and reversibly closing at least one distal opening concurrently with the proximal opening of the implant 500 being open.

It is also to be noted that the plug 516 can be removed proximally from the passageway 530 via the proximal opening.

According to a second aspect of the invention, there is provided a procedure for installing a dental implant in the maxilla of a patient, and FIGS. 5(*a*) to 5(*f*) illustrate a first embodiment of such a dental implant installation procedure, which also includes a concurrent sinus augmentation procedure, according to the second aspect of the invention.

Referring first to FIG. 5(*a*), a cross-section of a patient's maxilla 900 includes a maxillary sinus 910 having a sinus membrane 906, which is also interchangeably referred to as the membrane, the subantral membrane or the Schneiderian membrane. By way of illustrative, non-limiting example, two existing teeth 931, 932 are shown, one on either side of the implantation site 950 where it is desired to install a dental implant, and where the thickness of the bony wall of the alveolar ridge 901 at the crest of the maxilla is initially insufficient for anchoring the dental implant. Of course, in particular applications of the implant installation procedure of the invention, one or both such adjacent teeth may be missing. In any case, this boney wall thickness may be the original thickness of the alveolar ridge when a real tooth existed at the implantation site 950, or the original bone thickness may have been reduced due to bone having been resorbed, as is often the case after teeth are removed from the maxilla.

Referring to FIG. 5(*b*), the first step in the dental implant installation procedure comprises cutting a window 972 in the crest or occlusal-facing gum tissue 902 where the implant is to be installed, and the gum tissue may be removed or pulled back. This window 972 is cut using the device 600 (optionally in conjunction with one or more of systems 620, 625, 630, 640, 650, collectively referred to as system 800—see FIG. 1) of the invention according to the first aspect of the present invention, for example. Alternatively, any suitable traditional tool can be used for creating the window, for example a scalpel.

Then, and also referring to the device 600 illustrated in FIG. 1, the distal portion 130' of the device 600 is brought into proximity with the crest 962 and a suitable tool having a working end 91', such as a dental drill or laser, for example, is provided via central passageway 150'. The tool removes, by drilling, ablation, or any other suitable bone and tissue material removal process, a bone section of the alveolar ridge 901 to create a channel 965. The material removal operation is under constant monitoring by the surgeon operating the device 600, via the image acquisition unit 145' and the image acquisition system 620 and display 625, while the area being cut and monitored is illuminated via illumination arrangement 170'. Bone tissue is removed until the sinus membrane 906 is exposed, and this point in the procedure is identified in a relatively easy manner since the area being operated on by the working end 91' of tool is in the field of view of the image acquisition unit 145' and thus in constant visual observation by the surgeon via the imaging system, which can provide the surgeon with a magnified video image in real time of this area.

Alternatively, the channel 965 can be created using conventional tools and procedure, for example as follows. An X-ray of the maxilla is first taken to determine the depth of the alveolar ridge 901, and a conventional tool such as for example a laser or mechanical drill is used to create a bore that is essentially a proximal part of the channel 965, to a depth about 1 mm less than aforesaid predetermined depth. A second tool is then used to knock out the remaining bone at the distal end of this bore, to thereby complete the channel 965 this second tool can also be a conventional tool used for this purpose, or alternatively device 600 can be used, suitably equipped with a tool that can carry out the tapping function. Alternatively, device 600 is used with a laser or drill tool to remove the remaining bone at the distal end of this bore under monitoring via the image acquisition unit 145'.

In the next step, illustrated in FIG. 5(*c*), a dental implant according to the first aspect of the invention is installed in the maxilla 900 via the channel 965. In this figure, and by way of example, the dental implant 100 of FIG. 2 (or alternative variations thereof) is partially inserted into channel 965 in the distal direction until the distal end 160 abuttingly contacts the sinus membrane 906. Concurrent with at least a latter part of this insertion process, device 600, in particular the via the image acquisition unit 145' and the image acquisition system 620 and display 625, are used for monitoring the insertion process. The image acquisition unit 145' is aligned with the axis 101 of the implant 100 such that the distal opening 159 is in the field of view of the image acquisition unit 145', enabling the user to visually see the area distal of the opening 159 via display 625. Optionally, the image acquisition unit 145' can be inserted into the passageway 130 close to the distal opening 159 in embodiments where the image acquisition unit 145' can be accommodated in the passageway 130; otherwise, the image acquisition unit 145' can be used for obtaining images from outside of the proximal end 160 of the implant.

Thus, it is readily apparent to the user when contact is made between the distal end 160 and the sinus membrane 906. Thereafter, the dental implant 100 is further inserted distally into the maxilla in an incremental manner, and as the distal end projects distally further and further into the maxilla 900, the distal end 160 pushes against the sinus membrane 906 and gently and directly lifts mechanically the sinus membrane 906 from the maxillary sinus floor 907, and thereby distally displaces the sinus membrane 906 to create space 905.

At least a majority of the displacement of the sinus membrane 906, at least in the vicinity of the distal end 160, is carried out concurrent with and responsive to the distal end 160 being incrementally projected into the sinus cavity, and this progress can be continuously monitored using device 600, thus minimizing risk of damage to the sinus membrane 906. For example, as the sinus membrane 906 is displaced, it may become stretched at some point, and concurrently undergoes a blanching as blood drains from the membrane's blood vessels. This blanching can be observed by means of the device 600, in particular the image acquisition unit 145', as a change in color of the membrane seen via opening 159 from a reddish color to a whitish colour, and provides an indication of the stress that is being applied to the sinus membrane 906. Thus, the user can stop the implant insertion procedure if it becomes apparent via the blanching that the sinus is stretched and that further stretching may cause the membrane to rupture. In such a case, the implant can be replaced with another implant having a shorter distal part 154 which will not require such stretching of the membrane.

However, to avoid the need for replacing the dental implant in the first place, a probe having a blunt distal end can be inserted into the channel 965 prior to installation of the implant. The probe can be in the form of a tool that is provided via the central passageway 130' of the device 600 and is controllably projected past the distal end 133' of the device 600 such as to displace the membrane 906 in a similar manner to that anticipated for the implant 100, while being monitored via the image acquisition unit 145'. When the sinus membrane becomes blanched, the corresponding projection of the probe distal end into the sinus cavity is recorded, and this provides at least a rough estimate for the dimension $L_d$ of the distal part 154. Thereafter, a suitable implant 100 having this dimension $L_d$ for the distal part 154 is used for the rest of the procedure.

Thus, any potential damage to the sinus membrane 906 can be easily spotted by the user during the procedure via the image acquisition unit 145' and imaging system, since at least a part of the sinus membrane 906 is in the field of view of the image acquisition unit. In such circumstances the insertion of the implant can be interrupted, and the implant removed so that the sinus membrane can be repaired. At this point, or earlier, if there is detected a rupture, tear or other damage to the sinus membrane, this can be repaired by overlaying a collagen membrane over the damaged sinus membrane, for example. This repair can also be carried out using the device 600, wherein the collagen membrane is manipulated into place over the damaged area via a suitable tool provided via the device 600, while monitoring the repair procedure via the image acquisition unit 145'. Thereafter, the implant can again be inserted into the maxilla.

Figure 5A:
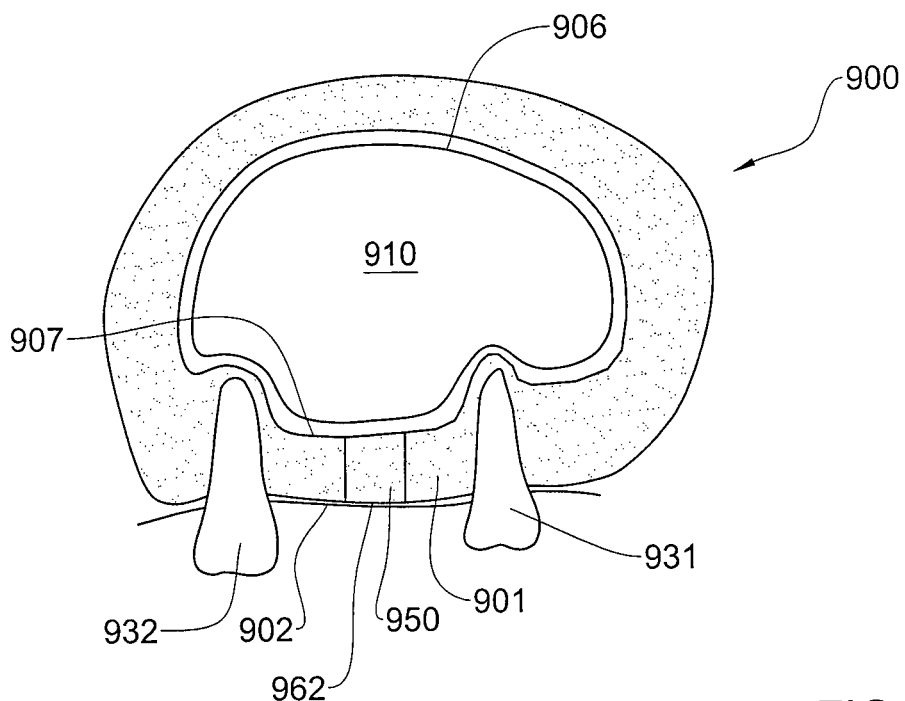
FIGS. 5(a) to 5(f) illustrate a dental implant installation procedure according to a first embodiment of the invention.
Figure 5B:
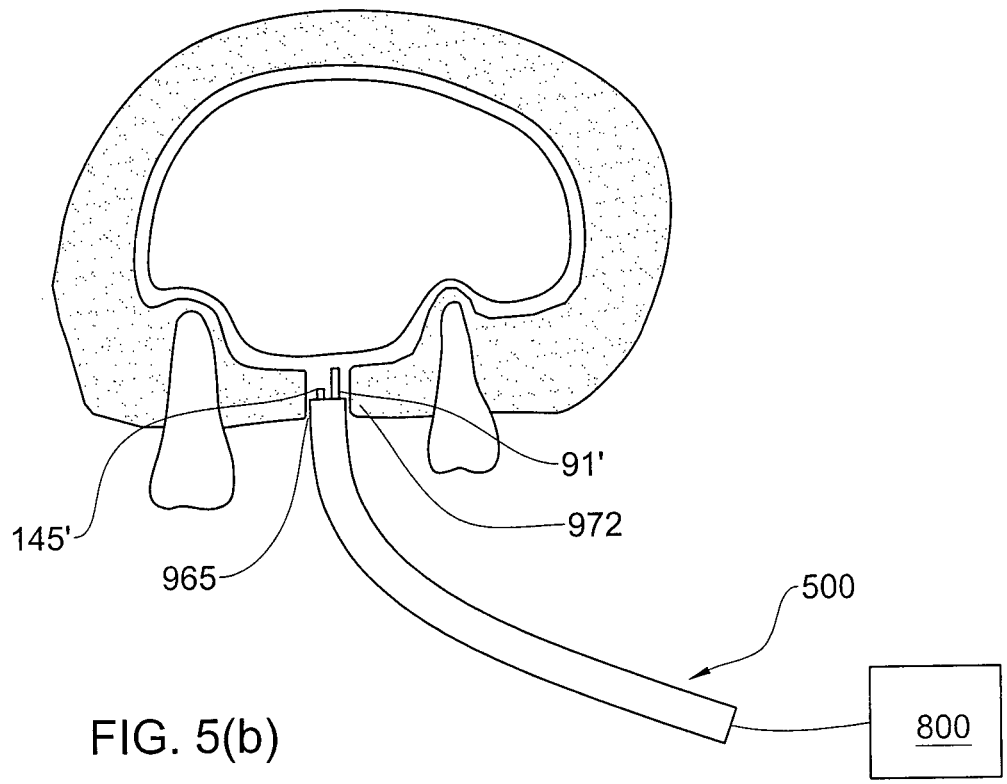
Figure 5C:
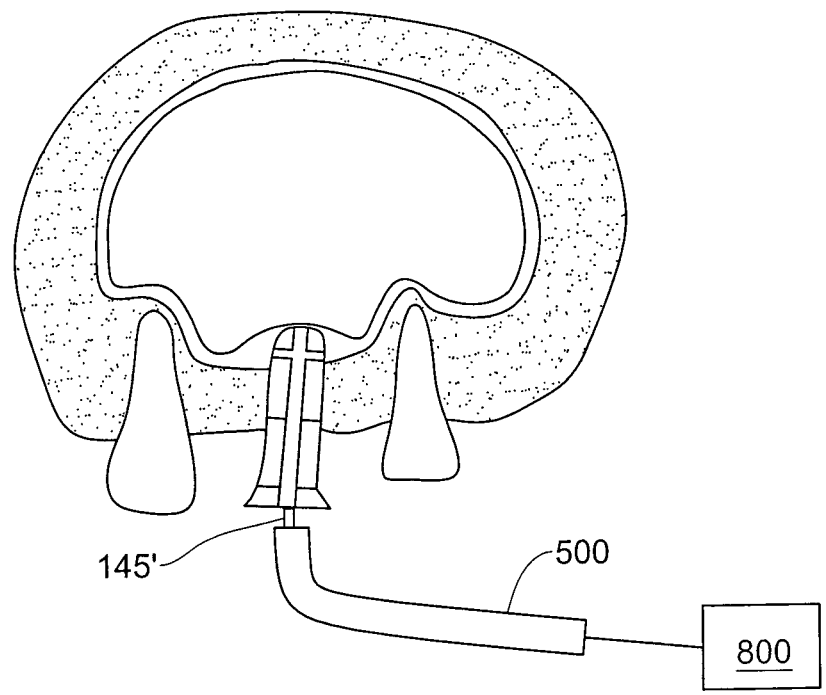
Figure 5D:
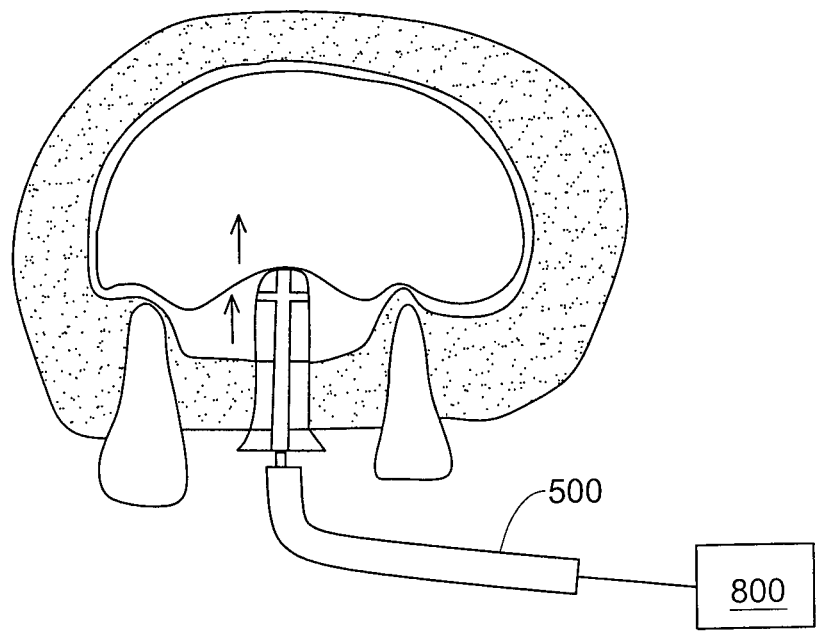

Otherwise, and referring to FIG. 5(d), the implant 100 is fully inserted into the maxilla 900 so that the proximal portion 110 is in the desired position, seated on the gingiva 902 of the maxilla 900 (see also FIG. 2). Thus, the distal part 254 projects a distance $L_d$ into the sinus cavity, similarly and concurrently displacing a corresponding portion of the sinus membrane 906.

Figure 5E:
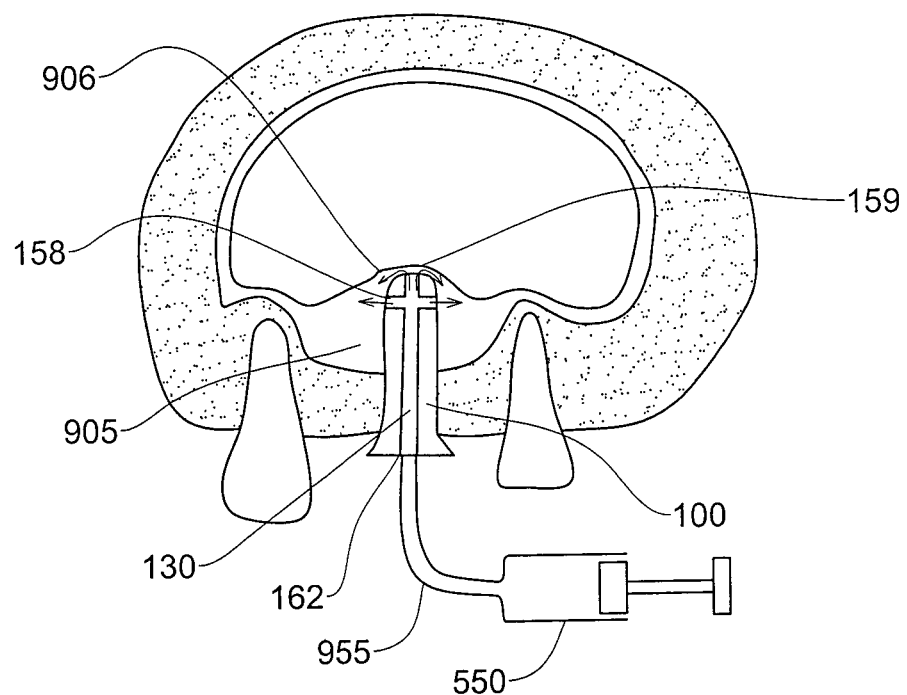

In the next step, illustrated in FIG. 5(e), a suitable bone graft material is introduced in the space 905, and this can be done in a variety of ways.

In one example, bone graft material in the form of BMP or other liquid bone substitute material is injected directly into the space 905 via a suitable syringe 650, in which the syringe needle in the form of delivery hose 955 (which can be flexible) is coupled to the opening 162 of the implant 100, via the fluid communication provided by passageway 130 and openings 158, 159.

Alternatively, the device 600 can be used for delivering the bone graft material into space 905. In this case, the device 600 is coupled with a syringe, in which a flexible syringe delivery needle or hose is accommodated in the central passageway 150' of the device, and the delivery end of the needle or hose projects distally from distal end of the device 600 and is coupled to the passageway 130. In such a case, the injection process can optionally be monitored via the image acquisition unit 145'.

Alternatively, the suitable bone graft material can be introduced in the space 905 incrementally, as the implant 100 is being introduced distally into the maxilla and after the implant has reached a distal position wherein the distal openings 158, 159 are just projecting distally past the alveolar ridge 901 and away from the sinus floor 907. As the distal end projects distally further and further into the maxilla 900, the distal end 160 pushes against the sinus membrane 906 and gently and directly lifts mechanically the sinus membrane 906 from the maxillary sinus floor 907, the suitable bone graft material is concurrently introduced into the space 905 being created by distal displacement of the sinus membrane 906. At the end of the process of providing bone graft material, the passageway 130 can optionally be left open, or alternatively can be sealed in a number of ways. For example, a temporary abutment can be engaged to the dental implant in a similar manner to that intended for the prosthesis 190, thereby closing the opening 162. Alternatively, a suitable plug, or a sealing material such as for example a dental adhesive or filler can be inserted in the passageway 130 via opening 162 to seal the passageway 130, for example as illustrated in FIG. 2(a), 2(b) or 2(c).

Figure 5F:
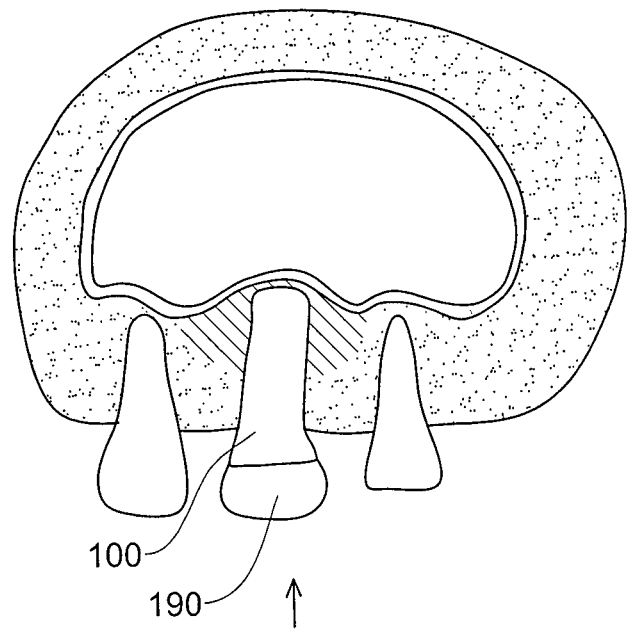

The bone graft material that is delivered to the space 906 forms a sinus augmentation, with the dental implant in situ, and the dental implant is anchored in place. Residual bone graft material left in the passageway 130 and openings 158, 159 further enhance the anchoring of the implant, wherein the sinus augmentation is allowed to heal and for the material in the space 905, passageway 130 and openings 158, 159 to become fully integrated with the boney tissues of the maxilla. After the healing process, the abutment can be removed if one was mounted to the implant, and a suitable prosthesis 190 is mounted to the implant, as illustrated in FIG. 5(f).

The implant installation procedure of FIGS. 5(a) to 5(f) can be applied to the implant embodiment of FIG. 3 in substantially the same manner as disclosed above for implant 100 and FIGS. 5(a) to 5(f), mutatis mutandis, with the difference that delivery of bone graft material is via axial distal opening 159 only.

The implant installation procedure of FIGS. 5(a) to 5(f) can be applied to the implant embodiment of FIG. 4 (or alternative variations thereof) in substantially the same manner as disclosed above for implant 100 and FIGS. 5(a) to 5(f), mutatis mutandis, with two main differences. One difference is that delivery of bone graft material is via lateral distal openings 258 only, either at the end of insertion of the implant 200, or, as the implant 200 is being inserted, wherein as the distal end 260 pushes against the sinus membrane 906 and gently and directly lifts mechanically the sinus membrane 906 from the maxillary sinus floor 907, the suitable bone graft material is concurrently introduced into the space 905 being created by distal displacement of the sinus membrane 906. Another difference is that monitoring of the sinus membrane during insertion of the implant, and subsequent thereto, is via the transparent distal end 260. In an alternative variation of the embodiment of FIG. 4, in which distal end 260 also comprises one or more distal openings, the bone graft material can also be provided via these openings, and/or monitoring can also be accomplished via these openings in addition to the transparent distal end itself.

Figure 14A:
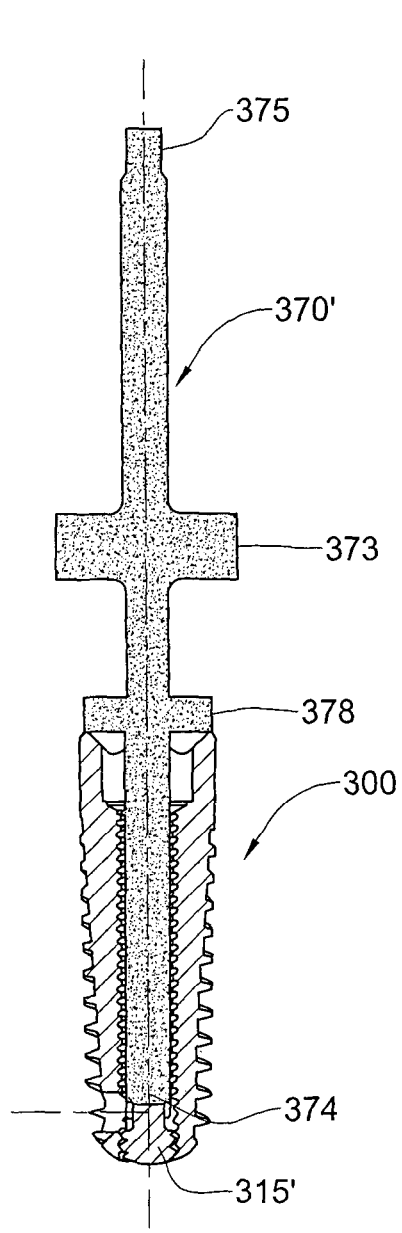
FIGS. 14(a) and 14(b) illustrate in side view the embodiment of the tool of FIG. 13, in use with the variation of the embodiment of FIG. 7 incorporating the embodiment of FIG. 12.

The implant installation procedure of FIGS. 5(a) to 5(f) can also be applied to the third implant embodiments of FIGS. 7 to 10 and 12 (or alternative variations thereof) in substantially the same manner as disclosed above for implant 100 and FIGS. 5(a) to 5(f), mutatis mutandis, with the main difference as follows. For the third implant embodiment of FIGS. 7 to 10, sealing of the passageway 330 can be accomplished by screwing in the distal plug 315 using end 374 of plug insertion tool 370, and this is followed by screwing in the proximal plug 314 using end 375 of plug insertion tool 370. For the variation of the third implant embodiment referenced to FIG. 12, sealing of the passageway 330 can be accomplished by screwing in the distal plug 315' using end 374' of plug insertion tool 370' (FIG. 14(a)), and this is followed by screwing in the proximal plug 314 using end 375 of plug insertion tool 370 (FIG. 14(b)).

Alternatively, the implant installation procedure of FIGS. 5(a) to 5(f) can be modified when applied to the third implant embodiment of FIGS. 7 to 10 and 12 (or alternative variations thereof), for example as follows.

In a first variation of the implant installation procedure of FIGS. 5(a) to 5(f), the distal end 360 of the implant 300 is closed by distal plug 315 using end 374 of plug insertion tool 370, or by distal plug 315' using end 374' of plug insertion tool 370', prior to insertion and installation of the implant 300 in the maxilla 900 via the channel 965. This may prevent direct visualization distal of the distal end 360 during installation in variations of these embodiments where the distal plug 315 or 315' is not transparent or does not comprised a transparent window. However, in at least some cases, having a closed distal end 360 can be advantageous in minimizing risk of damage to the sinus membrane during the installation procedure. Nevertheless, progress of the implant with respect to lifting of the sinus membrane can be visually inspected at intervals whenever desired by removing the respective distal plug 315 or 315' and looking distally along passageway 330, either directly, or via suitable imaging systems, for example an endoscope. After visual inspection, the distal plug 315 or 315' is screwed back into its distal position at the distal end of the implant 300, and the implant 300 can be advanced further another increment. Thus, the cycle of incremental distal advance, followed by visual inspection, followed by another incremental distal advance, followed by another visual inspection, and so on can be continued until the desired final (fully installed) position of the implant is reached.

Figure 14B:
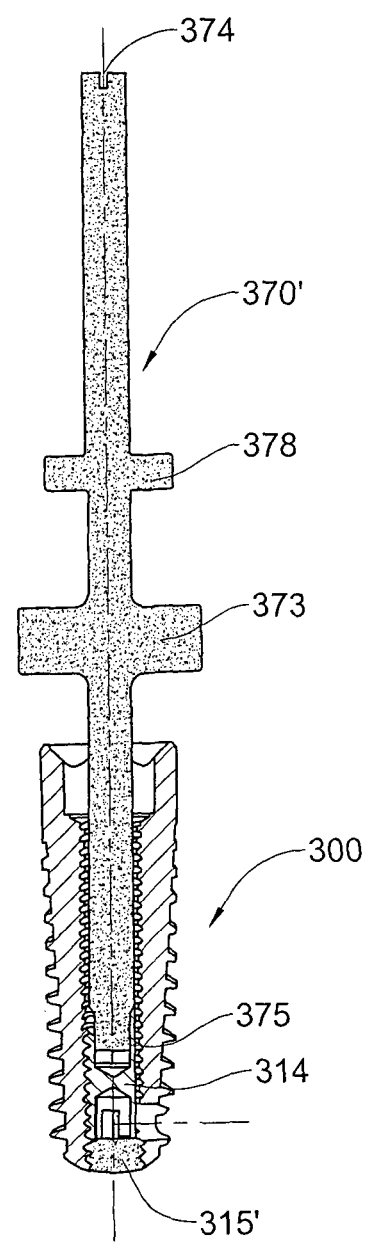

Once the implant 300 is fully installed, bone graft material can be provided via lateral distal openings 358 only, and the passageway 330, in particular the lateral distal openings 358 can be sealed by screwing in the proximal plug 314 using end 375 of plug insertion tool 370 (FIG. 14(b)).

Alternatively, once the implant is fully installed, the distal end 360 of the implant 300 is opened in respective embodiments by removing distal plug 315 using end 374 of plug insertion tool 370, or by removing distal plug 315' using end 374' of plug insertion tool 370'. Bone graft material is provided for the sinus augmentation via lateral distal openings 358 and axial distal opening 339, and on completion the passageway 330, in particular the axial distal opening 339 and the lateral distal openings 358 can be sealed by screwing in respective distal plug 315 or 315', and/or by screwing in the proximal plug 314 using end 375 of plug insertion tool 370.

Alternatively, bone graft material can be provided via the lateral distal openings 358 incrementally, as the implant 300 is being inserted, wherein as the closed distal end 360 pushes against the sinus membrane 906 and gently and directly lifts mechanically the sinus membrane 906 from the maxillary sinus floor 907, the suitable bone graft material is concurrently introduced into the space 905 being created by distal displacement of the sinus membrane 906. Once the implant 300 is fully installed, bone graft material can continue to be provided via lateral distal openings 358 only, and the passageway 330, in particular the lateral distal openings 358 can then be sealed by screwing in the proximal plug 314. Additionally or alternatively, once the implant 300 is fully installed, the respective distal plug 315 or 315' can be removed from the passageway 330 and bone graft material can continue to be provided via the axial distal opening 339, and thereafter the passageway 330, in particular the axial distal opening 339 and the lateral distal openings 358 can then be sealed by screwing in the respective distal plug 315 or 315' and/or the proximal plug 314.

The implant installation procedure of FIGS. 5(a) to 5(f) can also be applied to the fourth implant embodiment of FIGS. 17 to 21 (or alternative variations thereof) in substantially the same manner as disclosed above, in particular regarding implant 100 or implant 300, and FIGS. 5(a) to 5(f), mutatis mutandis, with the main difference as follows. For the fourth implant embodiment of FIGS. 17 to 21, sealing of the passageway 430 can be accomplished by screwing in the plug 416 using end 477 of tool 470. Alternatively, the implant installation procedure of FIGS. 5(a) to 5(f) can be modified when applied to the fourth implant embodiment of FIGS. 17 to 21 (or alternative variations thereof), for example as follows.

Figure 37:
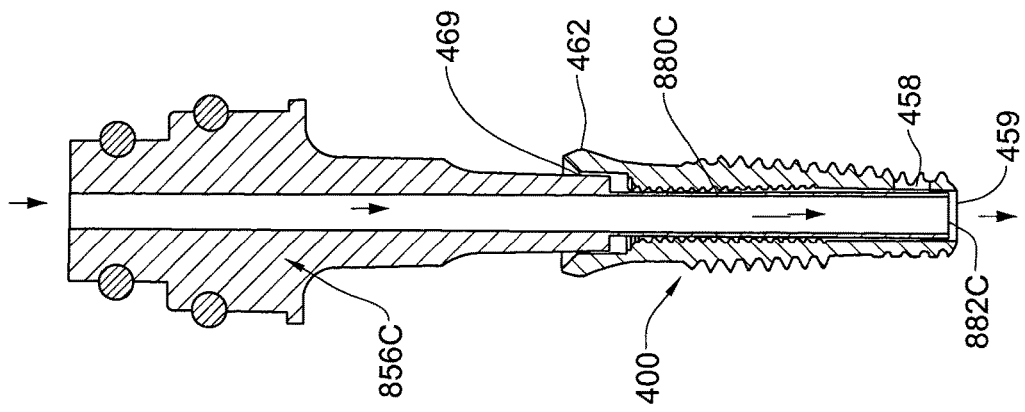
FIG. 37 illustrates in cross-sectional side view the dental implant driving head embodiment of FIG. 33 engaged with the embodiment of FIG. 17.
Figure 36:
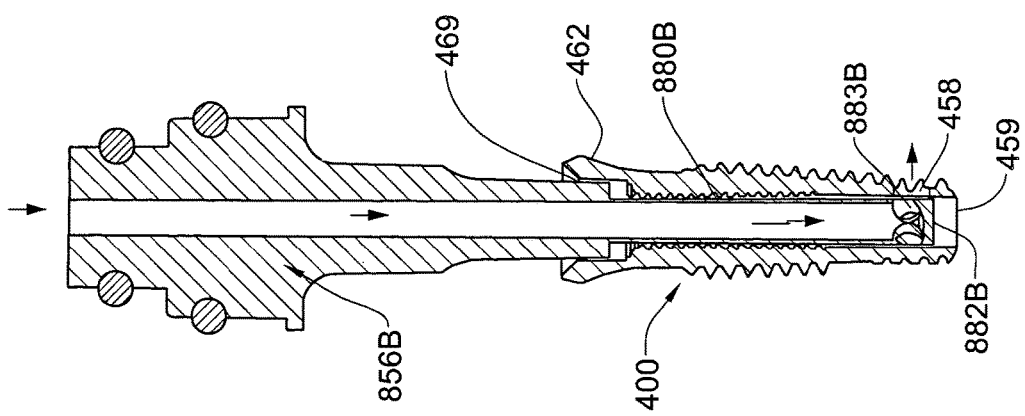
FIG. 36 illustrates in cross-sectional side view the dental implant driving head embodiment of FIG. 32 engaged with the embodiment of FIG. 17.
Figure 38:
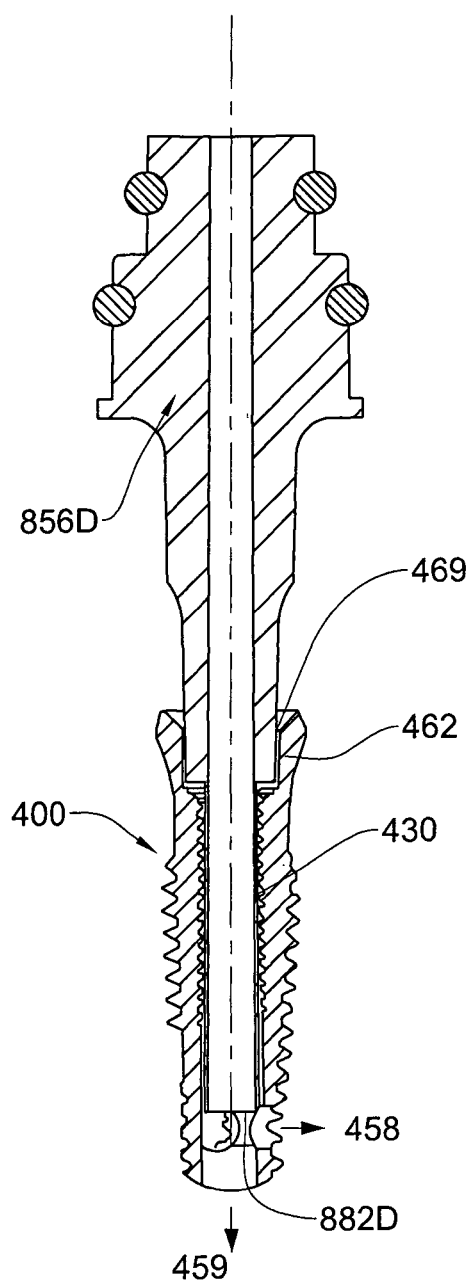
FIG. 38 illustrates in cross-sectional side view the dental implant driving head embodiment of FIG. 34 engaged with the embodiment of FIG. 17.

In a third variation of the implant installation procedure of FIGS. 5(a) to 5(f), the distal end 460 of the implant 300 is closed by plug 416, prior to insertion and installation of the implant 400 in the maxilla 900 via the channel 965. This can prevent direct visualization distal of the distal end 360 during installation in variations of these embodiments where the plug 416 is not transparent or does not comprise a transparent window. However, in at least some cases, having a closed distal end 460 can be advantageous in minimizing risk of damage to the sinus membrane during the installation procedure. Nevertheless, progress of the implant with respect to lifting of the sinus membrane can be visually inspected at intervals whenever desired by removing the plug 416 and looking distally along passageway 430, either directly, or via suitable imaging systems, for example an endoscope. After visual inspection, the plug 416 is screwed back into its distal position at the distal end of the implant 400, and the implant 400 can be advanced further another increment. Thus, the cycles of incremental distal advance, followed by visual inspection, followed by another incremental distal advance, followed by another visual inspection, and so on, can be continued until the desired final (fully installed) position of the implant is reached. Once the implant 400 is fully installed, the plug 416 can be removed and bone graft material can be provided: only via lateral distal openings 458 (for example using modified driving head 856B—see below and FIGS. 32 and 36); or only via axial distal opening 459 (for example using modified driving head 856C—see below and FIGS. 33 and 37); or via lateral distal openings 458 and axial distal opening 459 (for example: using driving head 856—see below and FIG. 30; or using modified driving head 856A—see below and FIGS. 31 and 35; or using modified driving head 856D—see below and FIGS. 34 and 38). The passageway 430, in particular the lateral distal openings 458 and axial distal opening 459, can be sealed by screwing in the plug 416 using tool 470, for example.

Optionally, also with the fourth embodiment, bone graft material can be provided only via the lateral distal openings 458 incrementally, as the implant 400 is being inserted, wherein as the distal end 460 pushes against the sinus membrane 906 and gently and directly lifts mechanically the sinus membrane 906 from the maxillary sinus floor 907, the suitable bone graft material is concurrently introduced into the space 905 being created by distal displacement of the sinus membrane 906. For example, modified driving head 856B (see below and FIGS. 32 and 36) can be used for this purpose. Once the implant 400 is fully installed, bone graft material can continue to be provided via lateral distal openings 458 only, and the passageway 430, in particular the lateral distal openings 458 and the axial distal opening 459 can then be sealed by screwing in the plug 416. Additionally or alternatively, once the implant 400 is fully installed, modified driving head 856C (see below and FIGS. 33 and 37) can instead be used and bone graft material can continue to be provided only via the axial distal opening 439, or via the axial distal opening 439 and the lateral distal openings 458 using any one of driving head 856 (see below and FIG. 30), modified driving head 856A (see below and FIGS. 31 and 35), or modified driving head 856D (see below and FIGS. 34 and 38). Thereafter the passageway 430, in particular the lateral distal openings 458 and the axial distal opening 459 can then be sealed by screwing in the plug 416. Alternatively, modified driving heads 856A, 856B, 856C, 856D can be used in any desired sequence to provide bone graft material as desired via the lateral distal openings 458 and/or the axial distal opening 459.

The implant installation procedure of FIGS. 5(a) to 5(f) can also be applied to the fifth implant embodiment of FIGS. 24 to 28 (or alternative variations thereof) in substantially the same manner as disclosed above for implant 100 or 300 or 400, and FIGS. 5(a) to 5(f), mutatis mutandis, with the main difference as follows. For the fifth implant embodiment of FIGS. 24 to 28, sealing of the passageway 530 can be accomplished by screwing in the plug 516 using tool 470. While the closed distal end 560 prevents direct visualization distal of the distal end 560 during installation, having a closed distal end 560 can be advantageous in minimizing risk of damage to the sinus membrane during the installation procedure. Nevertheless, it is possible to first gauge the maximum depth that the implant can be distally inserted, for example by use of a probe prior to implantation of the implant, as disclosed above for the first embodiment, mutatis mutandis, for example.

Once the implant 500 is fully installed, bone graft material can be provided via lateral distal openings 558, and the passageway 530, in particular the lateral distal openings 558 can be sealed by screwing in the plug 516 using tool 470, for example.

Alternatively, bone graft material can be provided via the lateral distal openings 558 incrementally, as the implant 500 is being inserted, wherein as the closed distal end 560 pushes against the sinus membrane 906 and gently and directly lifts mechanically the sinus membrane 906 from the maxillary sinus floor 907, the suitable bone graft material is concurrently introduced into the space 905 being created by distal displacement of the sinus membrane 906. Once the implant 500 is fully installed, bone graft material can continue to be provided via lateral distal openings 558 only, and the passageway 530, in particular the lateral distal openings 558 can then be sealed by screwing in the plug 516.

In the above examples, the bone graft material is provided for the sinus augmentation via syringe 650 or via a syringe coupled to device 600. Alternatively, bone graft material can be provided for the sinus augmentation via the respective first, second, third, fourth or fifth embodiments of the implant (or alternative variations thereof), in a number of alternative ways.

Figure 15:
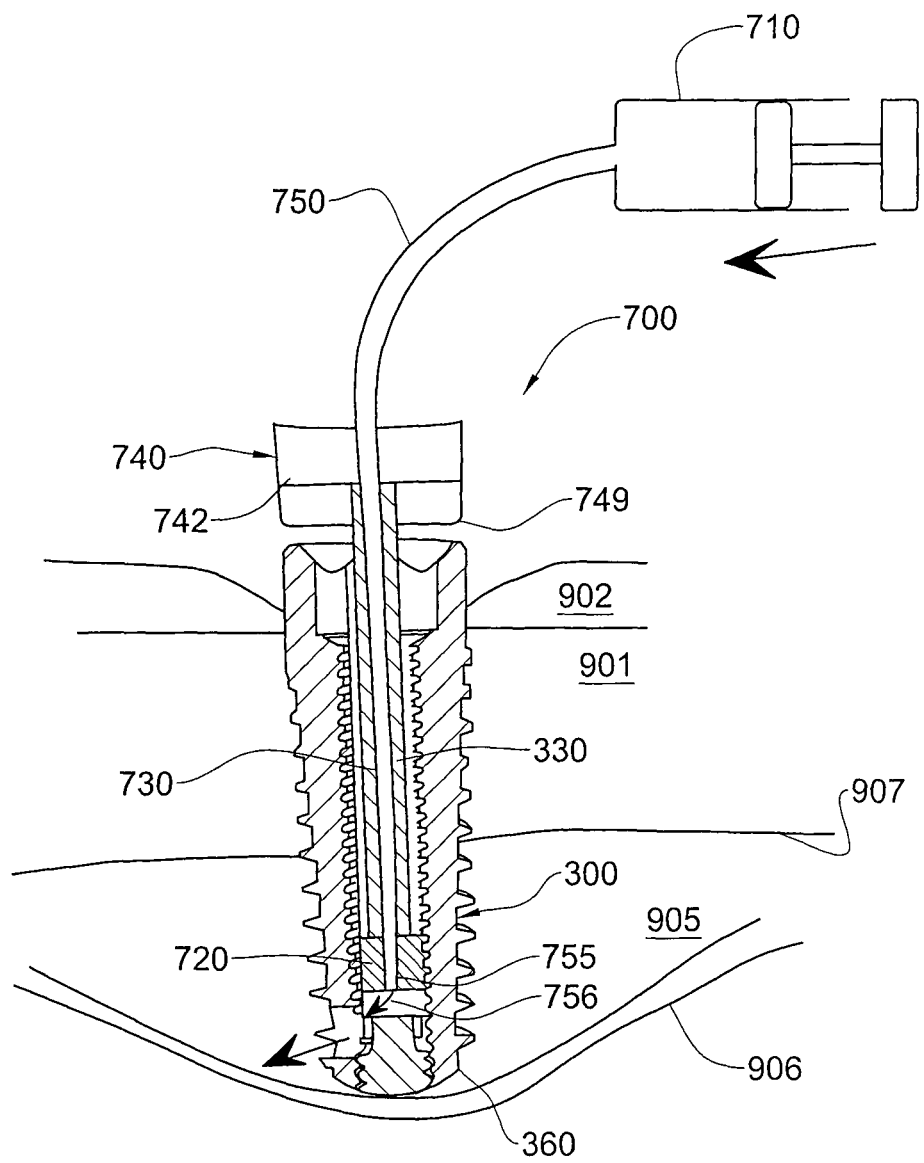
FIG. 15 illustrates a system and method for providing bone graft material for sinus augmentation via the dental implant embodiment of FIG. 7 and/or FIG. 12.

For example, and referring to FIG. 15, a first bone graft injection system 700 is illustrated in conjunction with an implant 300 according to the third embodiment (or alternative variations thereof). The injection system 700 is configured for injecting bone graft material in close proximity to the respective distal end 360 and at least lateral distal openings 358 thereof, and to minimize backflow of bone graft material in the proximal direction along the passageway 330 and possibly out of the proximal end of the implant 300. The injection system 700 comprises an injectable supply of bone graft material, in the form of syringe 710 accommodating bone graft material and having delivery tubing 750. The delivery end 755 of the tubing 750 is sealingly fixed to a sealing plug 720, so that the outlet 756 of the delivery end 755 is on the distal side of the sealing plug 720. The sealing plug 720 is externally threaded with threads that are complementary to, and effectively form a seal with, the internal threads of internally threaded passageway 330. The sealing plug 720 thus can be inserted distally into and removed from the passageway 330 via the proximal opening 362, thereby carrying therewith the outlet 756 of the delivery end 755. Insertion of the sealing plug 720 can be facilitated by driving portion 740, which comprises a finger actuating portion 742, that is rigidly (or at least semi-rigidly) connected to the sealing plug 720 via hollow drive shaft 730. Thus, the tubing 750 passes through an opening in the finger actuating portion 742 and through the hollow drive shaft 730. By rotating the finger actuating portion 742, the sealing plug 720 can be moved into or out of the passageway 330, taking with it the outlet 756 of the delivery end 755. In operation, the sealing plug 720 is inserted in a distal direction to a position near and proximal to the lateral distal openings 358, and bone graft material in the form of BMP or other liquid bone substitute material is injected directly into the space 905 by syringe 710, via outlet 756. Optionally, the injection of bone graft material can be done when the implant 300 is fully installed, or alternatively as often as desired while the implant 300 is being inserted: for example, the implant 300 can be advanced distally by a small increment (after the lateral distal openings 358 are distal of the sinus floor), then the sealing plug 720 is inserted into the passageway and bone graft material delivered to space 905, and thereafter the sealing plug 720 is removed to allow another incremental movement of the implant 300, further injection of bone graft material, and so on.

Optionally, the graft injection system 700 can be configured for facilitating positioning of the sealing plug 720 near and proximal to the lateral distal openings 358. For example, the finger actuating portion 742 can be positioned on the drive shaft 730 at a position such that when the distal face 749 of the finger actuating portion 742 abuts the proximal end of the implant 300, the sealing plug 720 near and proximal to the lateral distal openings 358. The distal face 749 of the finger actuating portion 742 acts as a stop, and prevents further distal ingress of the sealing plug 720, which could otherwise partially or fully obstruct the lateral distal openings 358 and/or press against the respective distal plug 315 or 315'.

The first bone graft injection system 700 can be used for injecting bone graft material also via the axial distal opening 359, and for this purpose the distal plug 315 or 315' is first removed.

The first bone graft injection system 700 can be used for injecting bone graft material only via the axial distal opening 359, and for this purpose the distal plug 315 or 315' is first removed, and the sealing plug 720 is inserted distally until it blocks the lateral distal openings 358, thereby enabling bone graft material to exit the implant 300 only via the axial distal opening 359. For such use, the graft injection system 700 is not configured for facilitating positioning of the sealing plug 720 near and proximal to the lateral distal openings 358, as described above, and therefore, the distal face 749 of the finger actuating portion 742 does not abut the proximal end of the implant 300 when the sealing plug 720 near and proximal to the lateral distal openings 358.

The first bone graft injection system 700 can also be used in conjunction with the first, second, fourth or fifth embodiments of the implant (or alternative variations thereof) in a similar manner to that described above for the third embodiment of the implant, mutatis mutandis.

Figure 16:
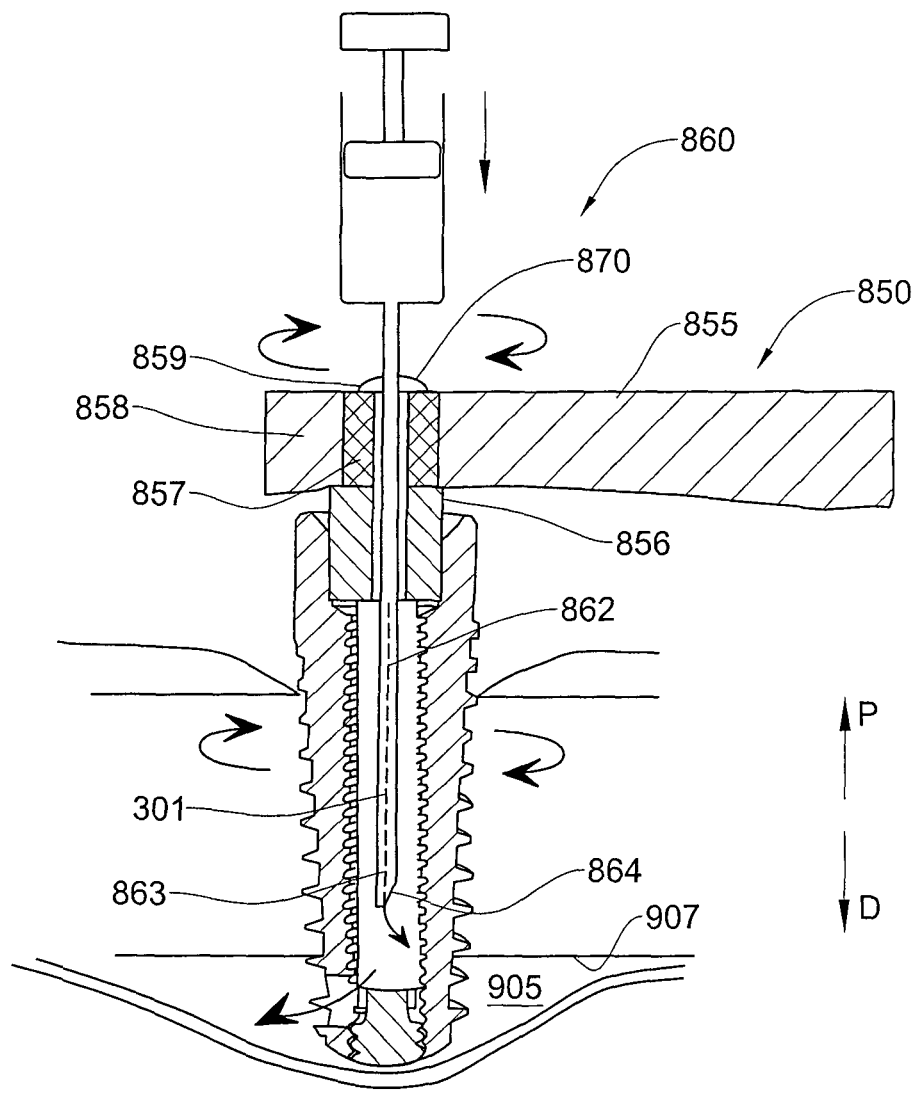
FIG. 16 illustrates another system and method for providing bone graft material for sinus augmentation via the dental implant embodiment of FIG. 7 and/or FIG. 12.
Figure 17:
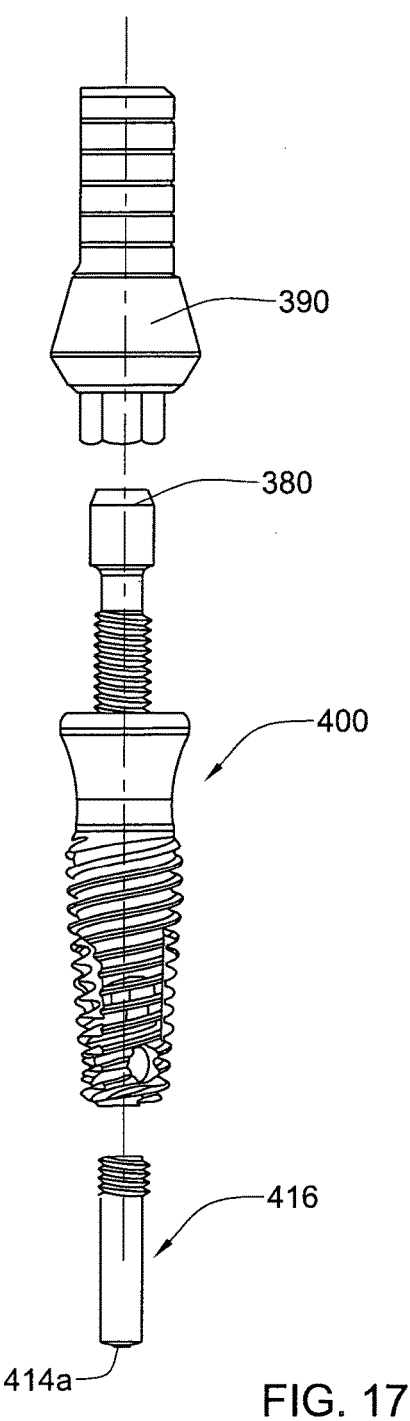
FIG. 17 illustrates in exploded side view, a dental implant according to a fourth embodiment of the invention.
Figure 18:
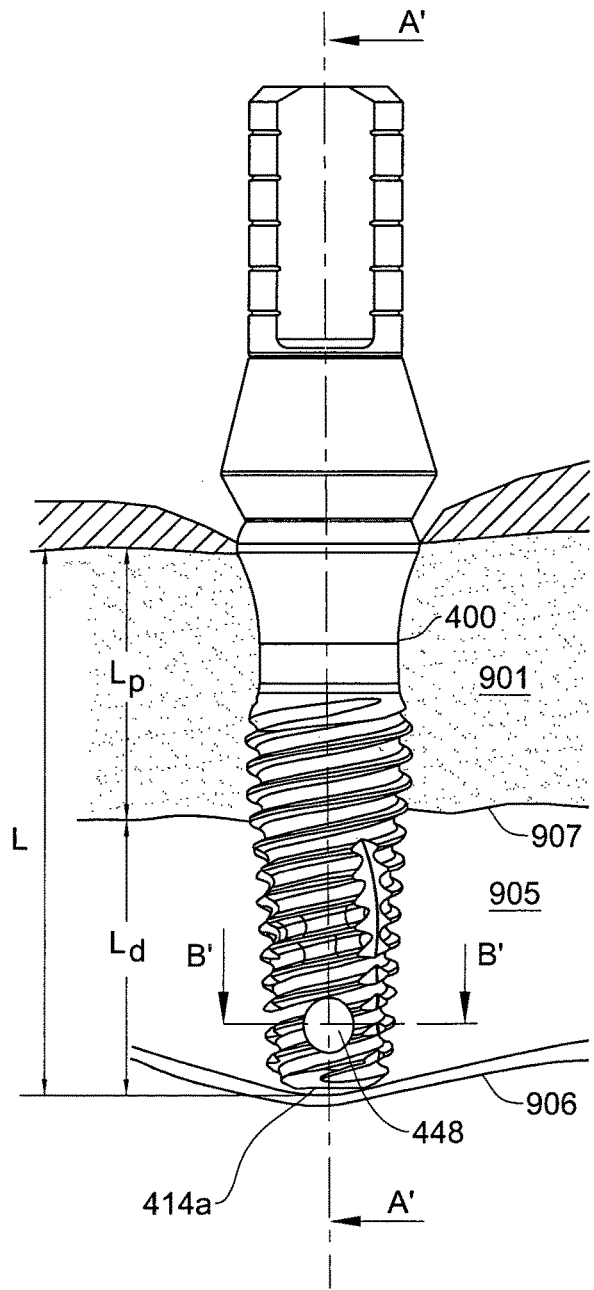
FIG. 18 illustrates, in side view, a dental implant according to the embodiment of FIG. 17.
Figure 21:
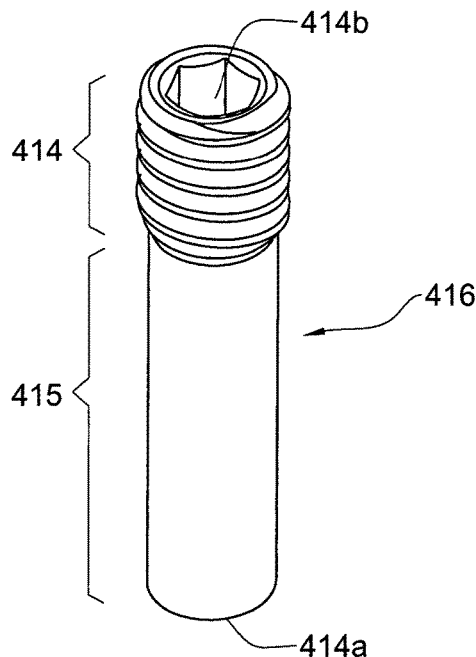
FIG. 21 illustrates in isometric view an alternative embodiment of the plug of the embodiment of FIG. 17.
Figure 20:
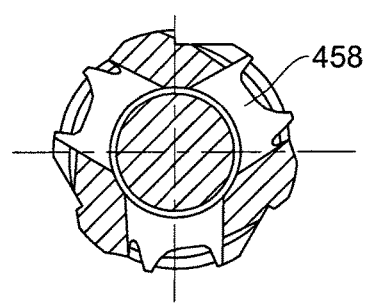
FIG. 20 illustrates, in cross-sectional view, a dental implant according to the embodiment of FIG. 18 along section B'-B'.
Figure 19:
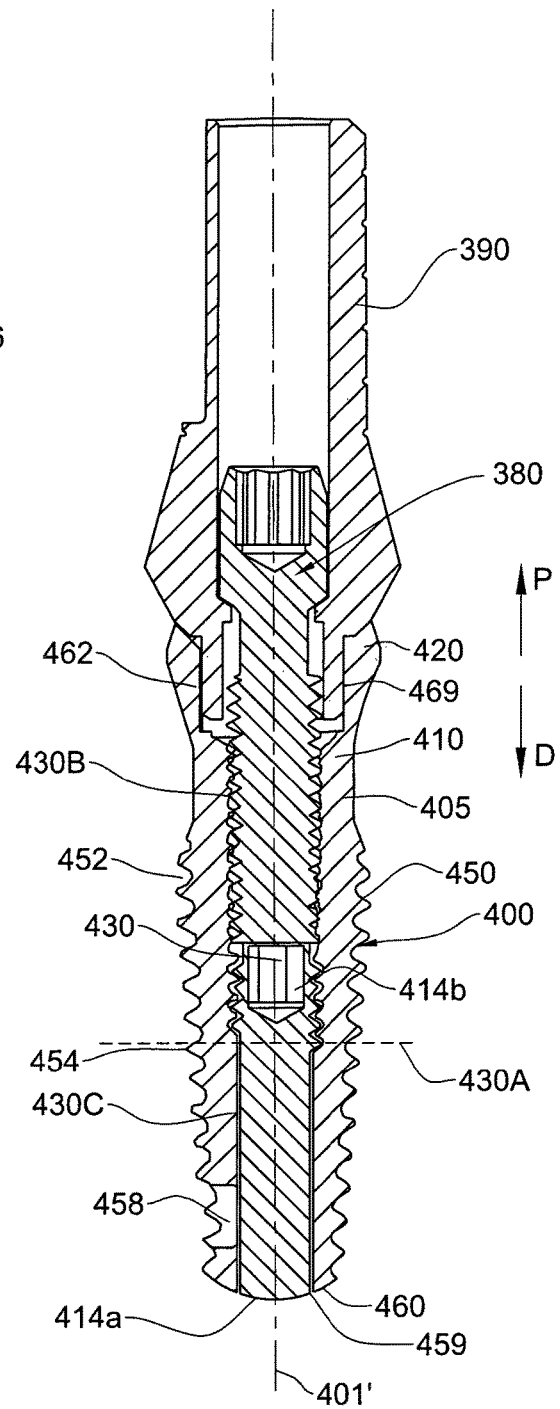
FIG. 19 illustrates, in transverse cross-sectional view, a dental implant according to the embodiment of FIG. 18 along section A'-A'.

In another example, and referring to FIG. 16, a second bone graft injection system 850 is illustrated in conjunction with an implant 300 according to the third embodiment (or alternative variations thereof). The second bone graft injection system 850 is also configured for injecting bone graft material in close proximity to the respective distal end 360 and at least lateral distal openings 358 thereof, particularly so that the bone graft material can be provided to the space 905 in a variety of radial directions as the implant 300 is being rotatably inserted into its installed position. In addition, the second bone graft injection system 850 is also configured for minimizing backflow of bone graft material in the proximal direction along the passageway 330 and possibly out of the proximal end of the implant 300.

The second bone graft injection system 850 comprises a dental implant torque wrench device 840 and a implant driving head 856, and an injectable supply of bone graft material, in the form of syringe 860 having delivery tubing 862 comprising a delivery end 863 and outlet 864.

The torque wrench device 840 comprises a gripping handle 855 that is reversibly engagable to implant driving head 856 via engagement ring 858, and is rotatable about implant driving head 856 via torque mechanism (not shown), and thus can be similar to conventional dental implant torque wrench devices per se, for example.

Figure 30:
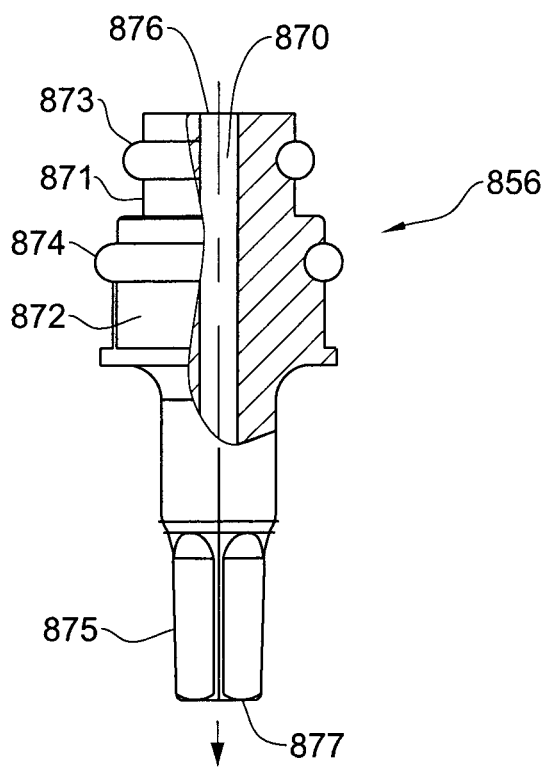
FIG. 30 illustrates in partially sectioned side view an embodiment of a dental implant driving head, that is drivable via a torque wrench device, and is particularly useful for use with the embodiment of FIG. 17 or 24.

Referring also to FIG. 30, driving head 856 comprises a proximal first wrench engaging portion 871 and a second wrench engaging portion 872, each in the form of different-sized hexagonal prismatic elements, each being alternately engageable with a corresponding, different-sized configuration of engagement ring 858. In other words, driving head 856 can be used with any one of two different torque wrench devices 840, each comprising an engagement ring 858 having a hexagonal engagement portion substantially complementary to one or another of said first wrench engaging portion 871 and said second wrench engaging portion 872. Respective resilient O-rings 873 and 874 assist in maintaining the torque wrench device 840 engaged with the respective said proximal first wrench engaging portion 871 or said second wrench engaging portion 872, during operation of the torque wrench device 840. In alternative variations of this embodiment, the driving head can comprise only one of said first wrench engaging portion 871 and said second wrench engaging portion 872.

The driving head 856 further comprises a distal implant engaging portion 875, in the form of a distally projecting hexagonal prismatic element that is substantially complementary with, and engages on, the hexagonally shaped well 369 at the proximal end 362 (or the hexagonally shaped well 469 at the proximal end 462. of the fourth embodiment, or hexagonally shaped well 569 at the proximal end 562 of the fifth embodiment, mutatis mutandis).

The driving head 856 further comprises a central throughbore or lumen 870 that is generally aligned with the longitudinal axis 301 of the implant 300 when the implant driving head 856 is in its actuating position engaged with the proximal end 362. The lumen 870 extends from a proximal inlet port 876 to a distal exit port 877 at the distal end of the implant engaging portion 875.

In the conventional manner, as the torque wrench device 840 is pivoted back and forth in one setting of the torque mechanism of the torque wrench device 840, the implant 300 is rotated about axis 301 in one direction and is thereby advanced distally into its installed position. On the other hand, while as the torque wrench device 840 is pivoted back and forth in a reverse setting of the torque mechanism of the torque wrench device 840, the implant 300 is rotated in the opposite direction and is advanced proximally away from the installed position.

The central lumen 870 allows the delivery end 863 and outlet 864 of the syringe 860 to be inserted into close proximity to the lateral distal openings 358, and optionally also to the axial distal opening 359 (when the respective distal plug 315 or 315' has been previously removed), and enables bone graft material to be injected into space 905 while the dental implant 300 is being screwed distally into the patient, thereby spreading the bone graft material in a plurality of radial directions from the axis 301. A sealer 859 can be provided at the proximal inlet port 876 of the lumen 870 to seal against the outside of the delivery tubing 860, and thus prevents escape of bone graft material via the lumen 870. For example, the sealer 859 can comprise a disc made from a memory rubber that can be pierced by a sharp needle (wherein the delivery end 863 is in the form of a sharp needle) and reseals when the needle is removed. Alternatively, the sealer 859 can comprise an O-ring that seals against the delivery end 863. Alternatively, a supply of bone graft can be connected to the inlet port 876 using suitable tubing.

The second bone graft injection system 850 can also be used in conjunction with the first, second, fourth or fifth embodiments of the implant (or alternative variations thereof) in a similar manner to that described above for the third embodiment of the implant, mutatis mutandis.

Referring to FIGS. 31 to 33, three alternative optional modifications of driving head 856 are illustrated.

A first modified driving head, designated with the reference numeral 856A is illustrated in FIG. 31 and is particularly configured for use with the implant 400 according to the fourth embodiment, although can be modified for use with other embodiments of the implant, mutatis mutandis. First modified driving head 856A comprises, in addition to the basic structure of the driving head 856, a hollow tube 880A distally extending from the respective distal port 877, and is configured for being accommodated in the central passageway 430 of the implant 400 according to the fourth embodiment, when the implant engaging portion 875, is engaged on, the respective hexagonally shaped well 469 at the proximal end 462 of the implant 400 (see FIG. 35). The hollow tube 880A has an open distal end 882A and a plurality of lateral openings 883A, which respectively face the axial distal opening 459 and lateral distal openings 458 when the modified driving head 856A is engaged with the implant 400. In use, bone graft material is injected into the lumen 870, and out of the axial distal opening 459 and lateral distal openings 458 via open distal end 882A and lateral openings 883A, and out of the implant 400. As the implant 400 is rotated by the torque wrench device 840, bone graft material can be concurrently provided to the implantation site both axially and radially (though the radial direction moves as the implant is rotated) via the axial distal opening 459 and lateral distal openings 458, respectively.

A second modified driving head, designated with the reference numeral 856B is illustrated in FIG. 32 and is particularly configured for use with the implant 400 according to the fourth embodiment, although can be modified for use with other embodiments of the implant, mutatis mutandis. Second modified driving head 856B comprises, in addition to the basic structure of the driving head 856, a hollow tube 880B distally extending from the respective distal port 877, and is configured for being accommodated in the central passageway 430 of the implant 400 according to the fourth embodiment, when the implant engaging portion 875, is engaged on, the respective hexagonally shaped well 469 at the proximal end 462 of the implant 400 (see FIG. 36). The hollow tube 880B has a closed distal end 882B and a plurality of lateral openings 883B, which face the lateral distal openings 458 when the modified driving head 856B is engaged with the implant 400. In use, bone graft material is injected into the lumen 870, and out of lateral distal openings 458 only via lateral openings 883, and out of the implant 400. The closed end 882B prevents bone graft material passing therethrough and out of axial distal opening 459. As the implant 400 is rotated by the torque wrench device 840, bone graft material can be concurrently provided to the implantation site only radially (though the radial direction moves as the implant is rotated) via the axial lateral distal openings 458.

A third modified driving head, designated with the reference numeral 856C is illustrated in FIG. 33 and is particularly configured for use with the implant 400 according to the fourth embodiment, although can be modified for use with other embodiments of the implant, mutatis mutandis. Third modified driving head 856C comprises, in addition to the basic structure of the driving head 856, a hollow tube 880C distally extending from the respective distal port 877, and is configured for being accommodated in the central passageway 430 of the implant 400 according to the fourth embodiment, when the implant engaging portion 875, is engaged on, the respective hexagonally shaped well 469 at the proximal end 462 of the implant 400 (see FIG. 37). The hollow tube 880C has an open distal end 882C and which faces the axial distal opening 459, and lateral distal openings 458 are blocked by a distal part of the tube 880C when the modified driving head 856C is engaged with the implant 400. In use, bone graft material is injected into the lumen 870, and out of the axial distal opening 459 only via open distal end 882A, and out of the implant 400. As the implant 400 is rotated by the torque wrench device 840, bone graft material can be concurrently provided to the implantation site only axially via the axial distal opening 459.

Figure 34:
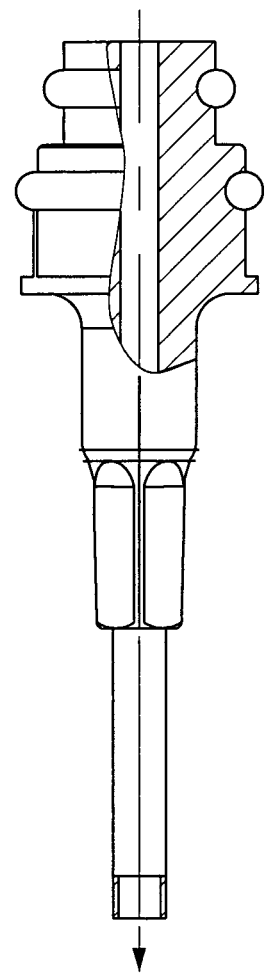
FIG. 34 illustrates in partially sectioned side view another modification of the embodiment of FIG. 30.
Figure 35:
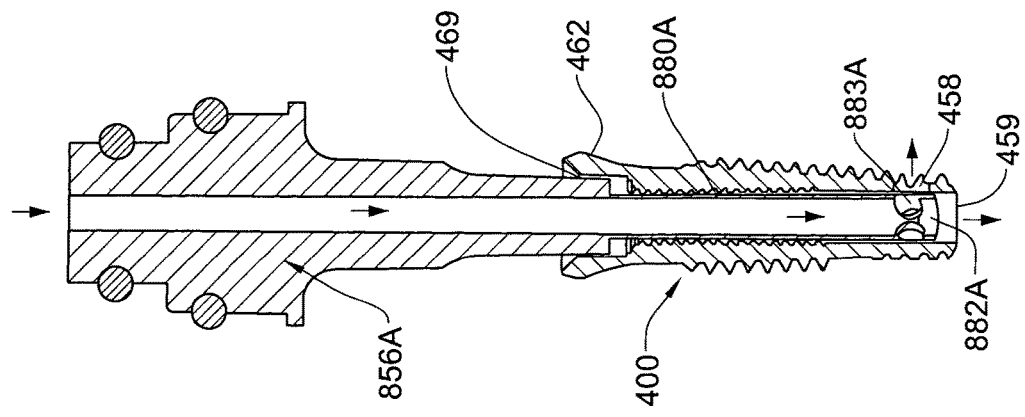
FIG. 35 illustrates in cross-sectional side view the dental implant driving head embodiment of FIG. 31 engaged with the embodiment of FIG. 17.
Figure 39:
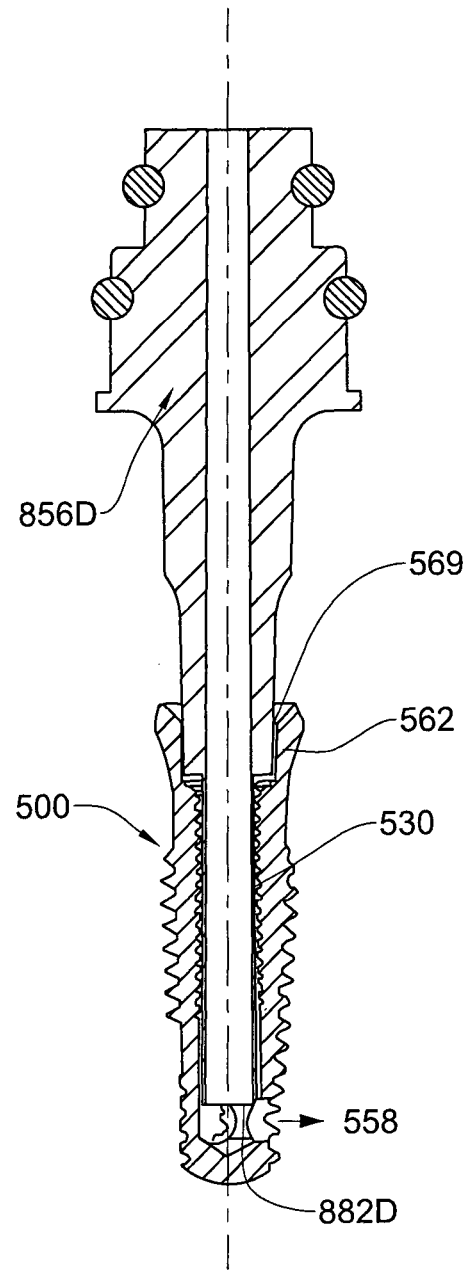
FIG. 39 illustrates in cross-sectional side view the dental implant driving head embodiment of FIG. 34 engaged with the embodiment of FIG. 24.

A fourth modified driving head, designated with the reference numeral 856D is illustrated in FIG. 34 and is particularly configured for use with the implant 400 or implant 500 according to the fourth or fifth embodiments, respectively, although can be modified for use with other embodiments of the implant, mutatis mutandis. Fourth modified driving head 856D comprises, in addition to the basic structure of the driving head 856, a hollow tube 880D distally extending from the respective distal port 877, and is configured for being accommodated in the central passageway 430 of the implant 400 according to the fourth embodiment, when the implant engaging portion 875, is engaged on, the respective hexagonally shaped well 469 at the proximal end 462 of the implant 400 (see FIG. 38). The hollow tube 880D has an open distal end 882D which face the axial distal opening 459 and is proximal of the lateral distal openings 458 when the modified driving head 856D is engaged with the implant 400. In use, bone graft material is injected into the lumen 870, and out of the axial distal opening 459 and lateral distal openings 458 via open distal end 882D, and out of the implant 400. As the implant 400 is rotated by the torque wrench device 840, bone graft material can be concurrently provided to the implantation site both axially and radially (though the radial direction moves as the implant is rotated) via the axial distal opening 459 and lateral distal openings 458, respectively. As may be seen, the tube 880D is similar to tube 880C, but shorter. Similarly, hollow tube 880D is also configured for being accommodated in the central passageway 530 of the implant 500 according to the fifth embodiment, when the implant engaging portion 875, is engaged on, the respective hexagonally shaped well 569 at the proximal end 562 of the implant 500 (see FIG. 39). The open distal end 882D which faces the closed axial distal end 560 and is proximal of the lateral distal openings 558 when the fourth modified driving head 856D is engaged with the implant 500. In use, bone graft material is injected into the lumen 870, and out of the lateral distal openings 558 via open distal end 882D, and out of the implant 500. As the implant 500 is rotated by the torque wrench device 840, bone graft material can be provided to the implantation site radially (though the radial direction moves as the implant is rotated) via the lateral distal openings 558, respectively.

While the implant installation procedure according to the second aspect of the invention has been described above with respect to the sinus cavity, it also applies, mutatis mutandis, to installing a dental implant with a corresponding "nasal elevation" or "nasal augmentation" in the nasal cavity (nasal fossa), for example for replacing missing upper incisors and/or canines.

A second embodiment of the dental implant installation procedure according to the second aspect of the invention is illustrated in FIGS. 6(a) to 6(d) and comprises all the elements and features of the first embodiment of FIGS. 5(a) to 5(f) and at least some alternative variations thereof, including the variations thereof disclosed above, for example in conjunction with the implant according to the first or second or third embodiments thereof or alternative variations thereof, though with some differences as will become clearer herein.

Figure 6A:
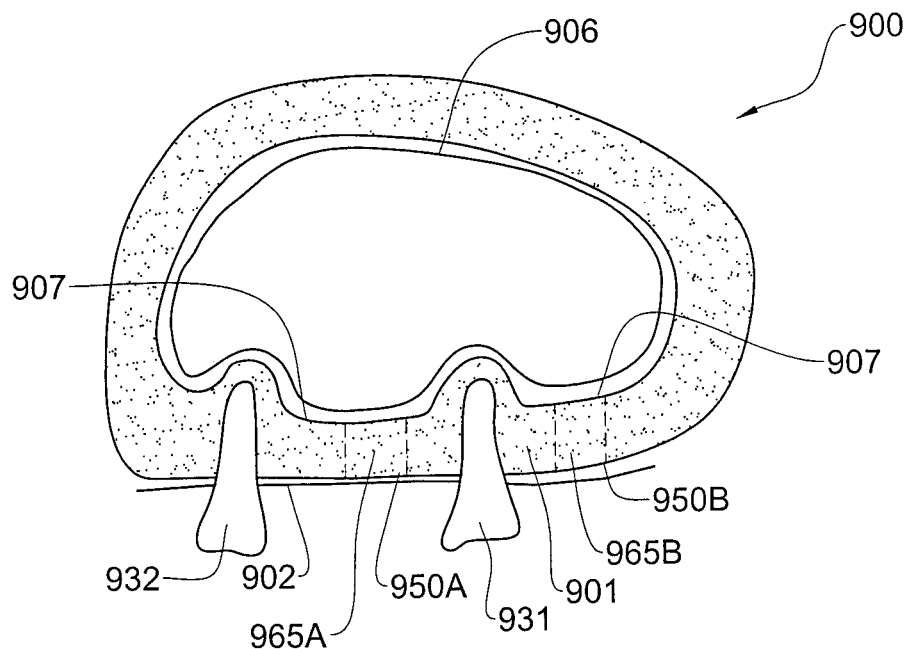
FIGS. 6(a) to 6(d) illustrate a dental implant installation procedure according to a second embodiment of the invention.
Figure 6B:
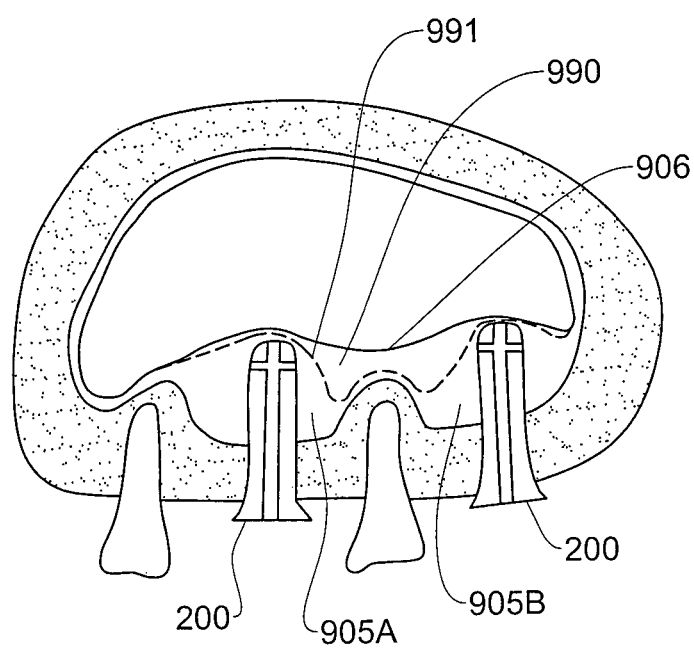
Figure 6C:
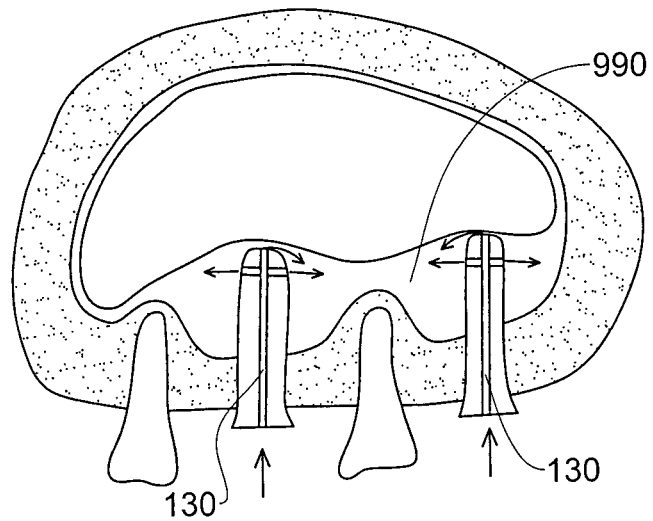
Figure 6D:
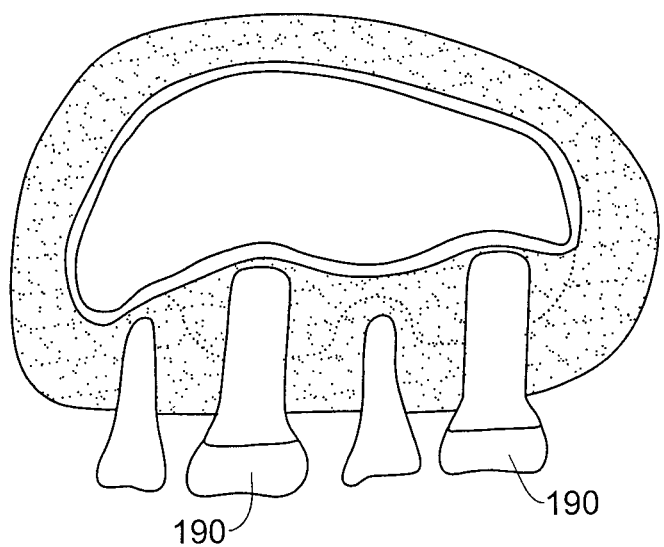

In the procedure illustrated in FIGS. 6(a) to 6(d), the two dental implants are installed in the maxilla, and a contiguous sinus augmentation is provided for both implants. Referring first to FIG. 6(a), two implantation sites, 950A, 950b are identified in the maxilla 900, the first site 950A is in-between existing teeth 931, 932, while the second site 950B is on the other side of tooth 931. Of course, in other particular applications of the implant installation procedure according to the second embodiment of the invention, one or both such adjacent teeth may be missing, and/or the procedure can be extended to additional implantation sites in proximity to one another.

Then, at each site 950A, 950B, a respective channel 965A, 965B is created, in a similar manner to that disclosed above for channel 965 of the first embodiment of the dental implant installation procedure, mutatis mutandis, for example in conjunction with FIG. 5(*b*). This is then followed by installation of a respective implant 100, 200 or 300 at each of the sites 950A, 950B, in a similar manner to that disclosed above with respect to channel 965, for example with reference to FIGS. 5(*c*) and 5(*d*), mutatis mutandis, though the dimension L or $L_d$ for each respective implant 100, 200, 300, 400 or 500 can be different. The implants can be installed in succession, or concurrently, in the latter case, each implant being alternately projected incrementally in direction towards the sinus cavity. However, since the two implants are in abutment with the sinus membrane 906 and directly raising the same from two spaced positions with respect to the sinus floor, a relatively larger cavity or space 990 is created than would be the case of the simple sum of the spaces 905A, 905B that could be created by each individual implant in the absence of the other, as indicated by the phantom line 991 in FIG. 6(*b*).

In the next step, illustrated in FIG. 6(*c*), a suitable bone graft material is injected into the cavity or space 990 via the respective passageway of each respective implant 100, 200, 300, 400 or 500, each in a similar manner to that disclosed above, for example, for the first embodiment, mutatis mutandis, for example with reference to FIG. 5(*e*), and optionally, the respective passageways can be sealed, for example as disclosed above with respect to FIGS. 2(*a*) to 2(*c*), or FIGS. 7 to 10 and 12, mutatis mutandis. This creates a contiguous sinus augmentation including both implants anchoring the implants. The sinus augmentation is allowed to heal and to become fully integrated with the boney tissues of the maxilla. After the healing process, the abutment can be removed if one was mounted to the implant, and a suitable prosthesis 190 is mounted to each implant, as illustrated in FIG. 6(*d*).

In a variation of the procedure illustrated in FIGS. 6(*a*) to 6(*d*), one of the two implants can be a conventional implant, i.e., in which said passageway is not present, but which comprises a non-cutting distal end, and in which a significant distal portion of the implant projects distally from the sinus floor, thereby displacing the corresponding part of the sinus membrane. In such an embodiment the injection of the bone graft material is via only the other implant, which thereby fills the whole space created by the displacement of the membrane.

It is also to be noted that the implant according to one or more of the first, second, third, fourth or fifth embodiments, or alternative variations thereof, is not necessarily limited to such implant or augmentation procedures as disclosed above, and can also be used for other implant procedures, for example such implant procedures which currently use conventional implants, in a similar manner thereto, mutatis mutandis.

Herein, alphanumeric characters and Roman numerals used to designate method steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A dental implant, comprising
an implant body having a proximal portion having at least one proximal opening and being configured to enable a prosthesis to be fixed to said implant body, and a distal portion having at least one axial distal opening at a distal end thereof,
the implant body further comprising
at least one internal passageway providing fluid communication between said at least one proximal opening and at least a first portion of an outside of said distal end via said at least one distal opening and said at least one internal passageway, and
a sealing arrangement configured for being removably accommodated within said passageway at a distal position therein such that said axial distal opening is closed thereby to prevent fluid communication between said proximal opening and said outside via said axial distal opening,
wherein said sealing arrangement is further configured when being disposed in said distal position to complementarily integrate with the implant body for rendering said distal end thereof devoid of any sharp surfaces or edges, wherein an overall contour line of said distal end extending between opposite lateral boundaries of said implant body, and being composed of contour lines' portions of said sealing arrangement and implant body which are congruent and forming together when so integrated the said overall contour line, such that said overall contour line thus formed is smooth without angular corners.

2. The dental implant according to claim 1, wherein said sealing arrangement comprises
a plug member having a plug distal portion and a plug proximal portion, said plug member being configured to be removably internally accommodated within said at least one internal passageway in a sealing position to form a seal therewith and to thereby close fluid communication between a distal portion of said at least one internal passageway including said at least one distal opening, and a proximal portion of said at least one internal passageway including said proximal opening.

3. The dental implant according to claim 2, wherein at least part of said at least one internal passageway distal portion is unthreaded and faces a corresponding unthreaded part of said plug distal portion when said plug member is in said sealing position.

4. The dental implant according to claim 2, wherein at least part of said at least one internal passageway proximal portion is threaded and cooperates with a correspondingly threaded part of said plug proximal portion at least when said plug member is in said sealing position, and wherein optionally said part of said passageway proximal portion extends up to said proximal opening.

5. The dental implant according to claim 2, wherein said implant is further configured for preventing said plug member from being removed distally from said at least one internal passageway, and wherein optionally said at least one internal passageway comprises a mechanical stop axially cooperating with said plug member for preventing removal of said plug member distally via said distal end.

6. The dental implant according to claim 2, wherein said plug member is further configured for being removably accommodated within said at least one internal passageway at a distal position therein such that said at least one distal opening is closed thereby from said proximal opening to thereby prevent fluid communication between said proximal opening and said outside via said distal openings.

7. The dental implant according to claim 2, wherein said plug member is transparent or comprises a transparent window.

8. The dental implant according to claim 2, wherein at least one said distal opening is an axial distal opening provided at said distal end, wherein said plug member is configured for being removably accommodated within said passageway at a first distal position therein such that said axial distal opening is closed thereby to prevent fluid communication between said proximal opening and said outside via said axial distal opening, and wherein said sealing arrangement further comprises an auxiliary plug member, different from said plug member, and configured to be removably accommodated within said at least one internal passageway at a second distal position therein such that said lateral distal openings are closed thereby to prevent fluid communication between said proximal opening and said outside via said lateral distal openings.

9. The dental implant according to claim 1, wherein said sealing arrangement is configured for selectively and reversibly closing said fluid communication independently of said proximal opening being open or closed.

10. The dental implant according to claim 1, wherein said distal portion comprises an external screw thread arrangement for directly engaging with tissues of one of the maxilla and mandible for enabling the dental implant to be directly implanted with respect thereto.

11. The dental implant according to claim 1, wherein said distal end comprises a blunt abutment portion.

12. The dental implant according to claim 1, wherein said sealing arrangement is proximally removable via said proximal opening.

13. The dental implant according to claim 1, wherein said sealing arrangement is configured for selectively and reversibly closing said at least one distal opening by sealing off a passageway distal portion of said at least one internal passageway including said at least one said distal opening, from a passageway proximal portion of said passageway.

14. The dental implant according to claim 1, wherein said distal end is configured to directly displace at least a portion of a corresponding sinus membrane during installation of the dental implant.

15. The dental implant according to claim 1, wherein said sealing arrangement is configured for maintaining fluid communication between an outside of said implant and said passageway distal portion via said at least one distal opening while concurrently sealing off said passageway distal portion from said at least one internal passageway proximal portion.

16. The dental implant according to claim 1, wherein said at least one internal passageway proximal portion is configured for anchoring therein the dental prosthesis when fixed to said implant.

17. The dental implant according to claim 1, wherein at least one said distal opening is an axial distal opening provided at said distal end, and wherein said axial distal opening, said proximal opening and said at least one internal passageway are aligned with a longitudinal axis of the dental implant to provide a direct line-of sight (LOS) between said axial distal opening and said proximal opening.

18. The dental implant according to claim 1, wherein the implant body further comprises a head configured to enable the prosthesis to be fixed to the proximal portion of the implant body.

19. The dental implant according to claim 1, wherein the sealing arrangement is configured to close said fluid communication independent of whether the prosthesis is fixed or unfixed with respect to the dental implant.

20. The dental implant according to claim 1, wherein said sealing arrangement is configured to allow accommodation of a prosthesis mounting arrangement in said at least one internal passageway proximal portion.

21. A dental implant, comprising
an implant body having a proximal portion having at least one proximal opening and being configured to enable a prosthesis to be fixed to said implant body, a distal portion having a distal end, and at least one distal opening at or near said distal end,
the implant body further comprising
at least one internal passageway providing fluid communication between said at least one proximal opening and at least a first portion of an outside of said distal end via said at least one distal opening and said at least one internal passageway, said at least one distal opening comprising an axial distal opening provided at said distal end and at least one lateral distal opening proximally displaced from said distal end on the implant body and laterally disposed with respect to said at least one internal passageway, and
a sealing arrangement configured for selectively and reversibly preventing fluid passage via said at least one distal opening,
wherein said sealing arrangement comprises a distal plug and a proximal plug, wherein said proximal plug is configured for preventing fluid passage via said at least one lateral distal opening when being positioned adjacent thereto, wherein said distal plug is configured for being positioned in either one of a distal sealing position and a proximal sealing position adjacent said at least one lateral distal opening, wherein said distal plug is configured for preventing fluid passage via said axial distal opening when being positioned in said distal sealing position, wherein said distal plug is further configured in the absence of said proximal plug for allowing fluid passage via said at least one lateral distal opening when being positioned in said distal sealing position, and preventing fluid passage via said at least one lateral distal opening from said outside into said at least one internal passageway when being positioned in said proximal sealing position.

22. The dental implant according to claim 21, wherein said distal is devoid of sharp surfaces or edges.

* * * * *